US005308863A

United States Patent [19]

Baldwin et al.

[11] Patent Number: 5,308,863

[45] Date of Patent: May 3, 1994

[54] SUBSTITUTED AROMATIC SULFONAMIDES AS ANTIGLAUCOMA AGENTS

[75] Inventors: John J. Baldwin, Gwynedd Valley; Gerald S. Ponticello; Charles N. Habecker, both of Lansdale; Harold G. Selnick, Ambler, all of Pa.

[73] Assignee: Merck & Co., Inc., Rahway, N.J.

[21] Appl. No.: 899,413

[22] Filed: Jun. 16, 1992

Related U.S. Application Data

[63] Continuation-in-part of Ser. No. 678,138, Apr. 4, 1991, abandoned, which is a continuation-in-part of Ser. No. 507,805, Apr. 12, 1990, abandoned.

[51] Int. Cl.[5] .................... A61K 31/38; C07D 333/00

[52] U.S. Cl. .................................. 514/431; 514/432; 514/913; 549/9; 549/23

[58] Field of Search ..................... 549/23, 9; 514/432, 514/913, 431

[56] References Cited

U.S. PATENT DOCUMENTS

| | | | |
|---|---|---|---|
| 4,619,939 | 10/1986 | Maren | 514/363 |
| 4,677,115 | 6/1987 | Baldwin et al. | 514/432 |
| 4,797,413 | 1/1989 | Baldwin et al. | 514/432 |
| 4,863,922 | 9/1989 | Baldwin et al. | 514/432 |
| 5,045,561 | 9/1991 | Baldwin et al. | 514/432 |
| 5,120,757 | 6/1992 | Baldwin et al. | 514/432 |

FOREIGN PATENT DOCUMENTS

| | | |
|---|---|---|
| 0193132 | 3/1987 | European Pat. Off. . |
| 0411704 | 3/1990 | European Pat. Off. . |
| 0452151 | 4/1990 | European Pat. Off. . |

*Primary Examiner*—Marianne M. Cintins
*Assistant Examiner*—Catherine S. Kilby Scalzo
*Attorney, Agent, or Firm*—Sylvia A. Ayler; Mark R. Daniel; Joseph F. DiPrima

[57] ABSTRACT

Thieno[2,3-b]thiopyran-2-sulfonamides and ring homologs with a hydrophilic substituted-alkyl group adjacent to the thiopyran sulfur are carbonic anhydrase inhibitors topically effective in lowering intraocular pressure.

15 Claims, No Drawings

SUBSTITUTED AROMATIC SULFONAMIDES AS ANTIGLAUCOMA AGENTS

This is a continuation-in-part of copending application U.S. Ser. No. 07/678/138, filed Apr. 4, 1991, now abandoned which in turn is a continuation-in-part of copending application U.S. Ser. No. 07/507,805, filed Apr. 12, 1990, now abandoned.

SUMMARY OF THE INVENTION

This invention relates to novel aromatic sulfonamides useful in the treatment of elevated intraocular pressure. More particularly this invention relates to compounds having the structural formula:

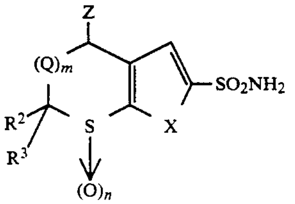

as well as the pharmaceutically and ophthalmologically acceptable salts thereof. This invention also relates to pharmaceutical compositions and the use thereof for systemic and ophthalmic use employing a novel compound of this invention as active ingredient for the treatment of elevated intraocular pressure, especially when accompanied by pathological damage such as in the disease known as glaucoma.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure. While many of these agents are effective in reducing intraocular pressure, they also have other characteristics, e.g. membrane stabilizing activity, that are not acceptable for chronic ocular use. (S)-1-tert-Butylamino--[(4-morpholino-1,2,5-thiadiazol-3-yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Although pilocarpine, physostigmine and the β-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof.

More recently, U.S. Pat. Nos. 4,677,115 and 4,797,413 describe topically effective carbonic anhydrase inhibitors which are thienothiopyran-2 sulfonamides differing from the compounds of the present application in the nature of the substituent on the thiopyran moiety adjacent to the sulfur atom.

DETAILED DESCRIPTION OF THE INVENTION

The novel compounds of this invention are those with structural formula:

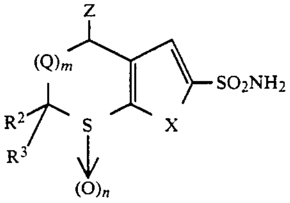

or a pharmaceutically acceptable salt thereof wherein:

X is —S—, or —O—;

m is I or 2;

n is 0, 1 or 2;

Z is 1) hydrogen,

2) $—OR^4$ wherein $R^4$ is a) hydrogen, or b) $C_{1-5}$ alkyl, either unsubstituted or substituted with i) —OH, or ii) $—NR^6R^7$ wherein $R^6$ and $R^7$ are independently hydrogen, $C_{1-3}$alkyl, —CO—$C_{1-3}$alkyl, or $R^6$ and $R^7$ taken together with the nitrogen to which they are attached represent a saturated heterocycle of 5–7 members which may include a second hetero group selected from O, S, SO, or $SO_2$ such as pyrrol-1-yl, piperidin-1-yl, morpholin-4-yl, thiomorpholin-1-yl and its oxide and dioxide, ═O, or

—NRR;

R is hydrogen or $R^1$;

$R^1$ is

1) $C_{2-7}$alkenyl,

2) $C_{2-7}$alkynyl,
3) $C_{1-6}$alkyl, straight, branched or cyclic, either unsubstituted or substituted with 1, 2 or 3 substituents wherein the substituents are independently:
a) halogen, such as fluoro, chloro or bromo;
b) hydroxy;
C) $C_{1-3}$alkoxy
d) $—NR^6R^7$
e) —S—$C_{1-3}$alkyl, or $(O)_n$
f) —CN; or R and $R^1$ taken together with the nitrogen to which they are attached represent a saturated heterocycle of 5–7 members which may include a second hetero group selected from O, S, SO, or $SO_2$ such as pyrrol-1-yl, piperidin-1-yl, morpholin-4-yl, thiomorpholin-1-yl and its oxide and dioxide;

$R^2$ is hydrogen or $C_{1-5}$alkyl;

$R^3$ is
1) —$C_{1-5}$ alkyl substituted with one or more of
a) hydroxy,
b) $—NR^8R^9$, wherein $R^8$ is
i) hydrogen, or
ii) $C_{1-3}$alkyl; and
$R^9$ is
i) $C_{1-3}$alkoxy-$C_{1-3}$alkyl,
ii) hydroxy-$C_{1-3}$alkyl,
iii) benzyl either unsubstituted or substituted on the phenyl group with up to three of halo, hydroxy, $C_{1-3}$alkyl, $C_{1-3}$alkoxy, $—CH_2NR^{10}R^{11}$ or $—NR^{10}R^{11}$ wherein $R^{10}$ and $R^{11}$ are independently hydrogen, $C_{1-3}$alkyl, or $C_{1-3}$alkoxy-$C_{1-3}$alkyl,
iv) —CO—$C_{1-6}$alkyl,
v) $—(CH_2)n$-heterocycle, wherein the heterocycle is of 5–6 members comprising one hetero atom selected from N, S and O, especially furan, and wherein the heterocycle can be unsubstituted or substituted with $—CH_2NR^{10}R^{11}$, or $R^8$ and $R^9$ taken together with the nitrogen to which they are attached represent a saturated or unsaturated heterocycle of 5–7 members which may include a second hetero group selected from O, N, S, SO, or $SO_2$,
c) $C_{1-5}$alkoxy, either unsubstituted or substituted with one or more of:
i) hydroxy,
ii) $C_{1-3}$ alkoxy,
iii) $NR^{10}R^{11}$,
iv) —CN,
v) phenyl, either unsubstituted or substituted with one or more of
A) hydroxy,
B) $C_{1-3}$alkoxy,
C) $C_{1-5}$alkyl—$NR^{10}R^{11}$
D) halo, such as chloro, fluoro or bromo,
vi) 5–6 membered heterocycle, saturated or unsaturated, comprising one hetero atom selected from O, N and S, especially furan, either unsubstituted or substituted with $—CH_2NR^{10}R^{11}$ vii) $—\underset{(O)_n}{S}—C_{1-3}$alkyl, viii) —SH d) $—\underset{(O)_n}{S}—C_{1-5}$alkyl, either unsubstituted or substituted with a 5–6 member heterocycle comprising one hetero atom selected from N, S and O,
e) —SH,
f) —CN, g) $—\underset{(O)_n}{S}—C_{2-4}$alkyl-OH, h) phenyl, either unsubstituted or substituted with up to three of
i) hydroxy,
ii) $C_{1-3}$alkoxy,
iii) $C_{1-5}$alkyl—$NR^{10}R^{11}$,
a 5–7 membered saturated heterocycle which may include a second hetero group selected from O, S, SO, or $SO_2$,
j) $COR^{14}$ wherein $R^{14}$ is
i) hydroxy
ii) $—NH_2$
iii) $C_{1-5}$ alkoxy, or
iv) $—NR^{12}R13$, or
k) $C_{2-5}$alkenyloxy; or $R^2$ and $R^3$ can be joined together to form a spiroheterocycle of 5–7 members wherein the heteroatom is a nitrogen, oxygen or sulfur, such as piperidine, tetrahydropyran, tetrahydrothiopyran, pyrrolidine, tetrahydrofuran, hexahydroazepine, thiepane or oxepane and when the heteroatom is nitrogen, the heteroatom can be substituted with
i) —$C_{1-3}$alkyl, or
ii) —$C_{1-3}$alkoxy-$C_{1-3}$alkyl; and

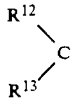
wherein $R^{12}$ and $R^{13}$ independently are hydrogen or $C_{1-4}$alkyl.

The presence of substituents on the dihydrothiopyran ring results in compounds with asymmetric carbons. This invention contemplates all of the enantiomers and diastereomers and mixtures thereof.

In the following specification and claims where the absolute configuration of a compound is expressed as cis(S,R)—, the (S) refers to the configuration at the 4-position, and the (R) refers to the configuration at the carbon adjacent to the $—S(O)_n—$ Of the thiopyran ring, which is the 6-position.

In a preferred embodiment of the novel compounds, X is S, m is 1, n is 2, Z is $—NRR^1$ and $R^{12}$ and $R^{13}$ are hydrogen.

It is preferred that R be hydrogen and that $R^1$ be $C_{1-6}$alkyl, especially $C_{2-4}$alkyl. It is further preferred that $R^2$ be hydrogen or $C_{1-3}$alkyl, and that $R^3$ be (i) $C_{1-5}$alkoxy-$C_{1-5}$alkyl especially ethoxyethyl or methoxypropyl, or (ii) hydroxy-$C_{1-5}$alkoxy-$C_{1-5}$alkyl, especially hydroxyethoxyethyl, or (iii) $C_{2-5}$alkenyloxy-$C_{1-5}$alkyl especially allyloxymethyl or allyloxypropyl, or (iv) $C_{1-3}$alkoxy-$C_{1-5}$alkoxy-$C_{1-5}$alkyl especially methoxyethoxypropyl, ethoxyethoxypropyl or methoxypropoxypropyl. The ophthalmologicaliy acceptable salts coming within the purview of this invention include the ophthalmologically acceptable acid addition salts. Acids useful for preparing these acid addition salts include, inter alia, inorganic acids, such as the hydrohalic acids (e.g., hydrochloric and hydrobromic acid), sulfuric acid, nitric acid, and phosphoric acids, and organic acids such as maleic, fumaric, tartaric, citric, acetic, benzoic, 2-acetoxybenzoic, salicylic, succinic, p-aminobenzoic, isethionic, lactic, p-acetmidobenzoic, methanesulfonic, or ethanedisulfonic acid.

The novel processes for preparing the novel compounds of this invention generally comprise as last step, formation of the —$NRR^1$ substituent.

Reduction of the N-acyl group with borane-dimethylsulfide complex in an ethereal solvent such as THF, diethylether, or 1,2-dimethoxyethane provides an alkylamino as exemplified below by reduction of acetamido to ethylamino. The amide starting materials can be prepared by acylation of the 4-amino compounds.

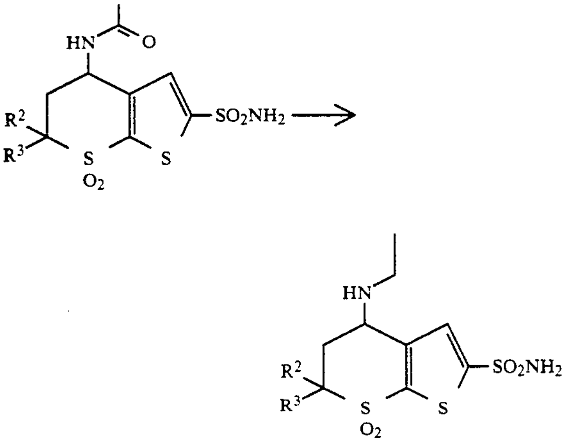

Alkylamino groups are also available from the corresponding 4-hydroxy compounds by treatment of the 4-hydroxy with toluenesulfonyl chloride in pyridine at about −20° C. to 5° C. for about 3 to 10 hours followed by the addition of an alkylamine at a temperature below about 15° C. followed by warming to about 30°–60° C. for about 5 to 16 hours as shown below:

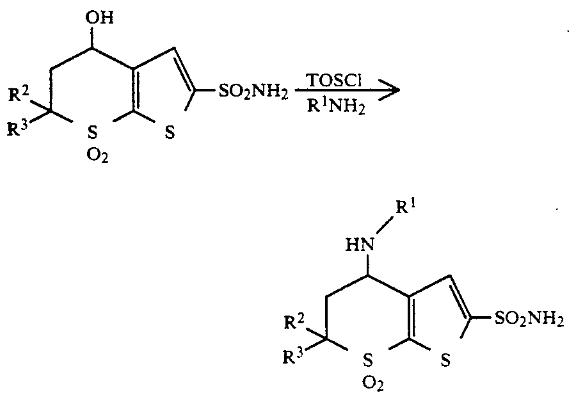

4-Alkylamines are also prepared from the 4-oxo compounds by the following scheme:

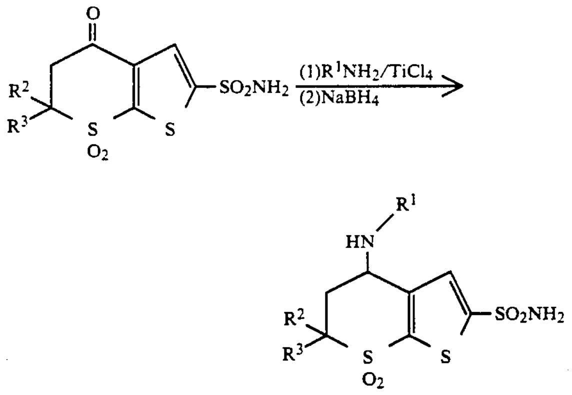

In this process a solution of the keto compound in a solvent such as diethylether, THF, 1,2-dimethoxyethane, benzene, toluene or mixtures thereof at about −20° C. to 0° C. is treated quickly with about a one molar excess of an amine of formula $R^1NH_2$ followed by titanium tetrachloride dropwise. After about 1 to 5 hours the mixture is filtered and evaporated. The residue is treated with a complex metal hydride such as sodium borohydride, in excess in a $C_{1-3}$alkanol, preferably methanol, at about room temperature for up to 24 hours. Excess hydride is destroyed with aqueous acid and the product is isolated by standard techniques.

This invention is particularly concerned with formulations adapted for topical ocular administration in the form of solutions, ointments, solid water-soluble inserts or gels for the treatment of glaucoma and other stages of elevated intraocular pressure and contain about 0.1% to 15% by weight of medicament, especially about 0.5% to 2% by weight of medicament, the remainder being comprised of carriers and other excipients well known in the art. The compounds of this invention are also useful for treating psoriasis, and therefore, this invention is also concerned with the topical use of the above formulations for the treatment of psoriasis.

The medicament in the novel topical ocular formulations for use in treating glaucoma and other stages of elevated intraocular pressure comprises one of the novel compounds of this invention either alone or in combination with a J3-adrenergic blocking agent such as timolol maleate, a para-sympathomimetic agent such as pilocarpine, or an angiotensin converting enzyme (ACE) inhibitor such as enalapril. The medicament combination may also contain other agents that reduce intraocular pressure, e.g., a potassium channel agonist such as cromokalin, an agonist at the cannabinoid receptor such as tetrahydrocannabinoid or WIN 55212-2, 2-ethyl-2,3-dihydro-5-methylpyrrolo[1,2,3-de]-1,4-benzoxazine-6-ethanamine, a dopamine agonist, ANF or a prostoglandin. In such combinations the two active agents are present in approximately equal amounts.

The medicament in the novel topical formulations for use in treating psoriasis comprises one of the novel compounds of this invention in free-base form. The compounds of this invention can also be orally administered to patients in need of treatment for psoriasis in typical pharmaceutical formulations such as tablets, capsules and elixirs. Although the dose will vary from patient to patient depending upon the nature and severity of disease, the patient's weight, and other factors which those skilled in the art will recognize, the dosage range will generally be about 1 to 500 mg. per patient per day, which can be administered in doses from once to three times a day. Preferably, the dosage range will be about 2 to 100 mg. per patient per day.

One novel method of treatment of this invention comprises the treatment of elevated intraocular pressure by the administration of a novel compound of this invention or pharmaceutical formulation thereof. Of primary concern is the treatment by topical ocular administration of about 0.1 to 25 mg and especially 0.1 to 10 mg of such compound per day, either by single dose or on a 2 to 4 dose per day regimen.

Another novel method of treatment of this invention comprises the treatment of psoriasis by the oral or topical administration of a novel compound of this invention or pharmaceutical formulation thereof.

As used herein, the α designation refers to the trans configuration and the β designation refers to the cis configuration, except for in Example 42 where the α designation refers to the first compound to elute from the chromatography column.

EXAMPLE 1

5,6-Dihydro-4-N-ethylamino-spiro[tetrahydropyran-4',6(6'H)-thieno[2,3-b]thiopyran]-2-sulfonamide-7,7-dioxide hydrochloride.

Step A:

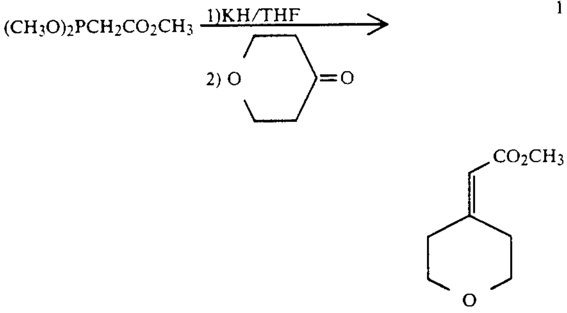

1

Under $N_2$, 25% KH in mineral oil (5.4 g, 0.14 mol) was added to THF (150 ml). The suspension was cooled in an ice bath (0.4° C.) and a solution of trimethyl phosphonacetate (25.2 g, 0.14 mol) in THF (45 ml) was added dropwise with mechanical stirring. After 15 minutes, tetrahydropyran-4-one (4.5 g, .045 mol) in THF (50 ml) was added dropwise to the thick suspension. The reaction mixture was then stirred at room temperature. After stirring overnight, water was added and the mixture was extracted with ethyl acetate (2×). The organic extract was washed with $H_2O$ (2×), saturated NaCl, dried, filtered and concentrated to dryness to yield a quantitative yield of ester 1.

Step B:

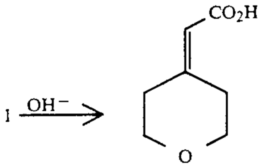

2

A solution of 1 (19.8 g, 0.13 mol) in abs. ethanol (150 ml) and 30% NaOH (70 ml) was heated at reflux for 2 hours. After stirring at room temperature overnight, the solution was acidified with 6N HCl and the aqueous phase extracted with ethyl acetate (3×). The organic extracts were backwashed with saturated NaCl, dried, filtered, and concentrated to dryness. The residue was triturated with hexane to yield 2 (18 g, 100%). An analylical sample was prepared by crystallization from $CH_2Cl_2$-hexane to yield material which analyzed for $C_7H_{10}O_3$; mp 95°-97° C.

Calc'd, C, 59.14; H, 7.09; Obs. C, 59.32; H, 6.81.

Step C:

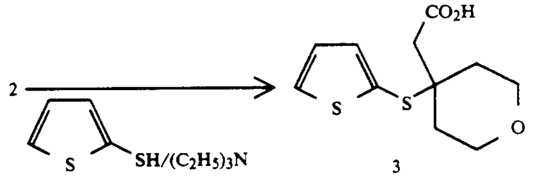

3

A mixture of 2 (18 g, 0.13 mol) in THF (200 ml), 2-mercaptothiophene (15.0 g, 0.13 mol) and $(C_2H_5)_3$ N (8 ml) was heated at reflux. After 20 hours, the reaction was cooled to room temperature and acidified. The aqueous layer was extracted with ethyl acetate (3×). The organic extract was dried, filtered and concentrated to dryness to yield a quantitative yield of 3.

Step D:

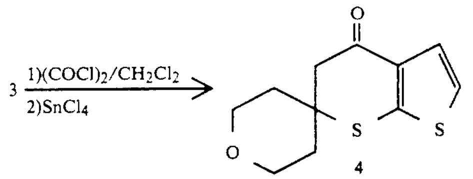

4

To a mixture of 3 (32.7 g, 0.13 mol), $CH_2Cl_2$ (200 ml), and DMF (I ml) was added dropwise under $N_2$ oxalyl chloride (12 ml, 17.4 g, 0.14 mol) in $CH_2Cl_2$ (20 ml). After stirring for 1 hour at room temperature, the solution was cooled to −25° C. and a solution of $SnCl_4$ (7.5 ml, 12.9 g, 0.068 mol) in $CH_2Cl_2$ (25 ml) was added dropwise. The solution was allowed to stir at room temperature and after 2.5 hours water was added and separated. The aqueous phase was washed with $CH_2Cl_2$ (2×). The organic extracts were washed with $H_2O$, saturated $NaHCO_3$, dried, filtered and concentrated to dryness. The residue was chromtographed on silica gel on a Still column and the product was eluted with 15% ethyl acetate/hexane to yield 11.6 g (38%) of 4.

Step E:

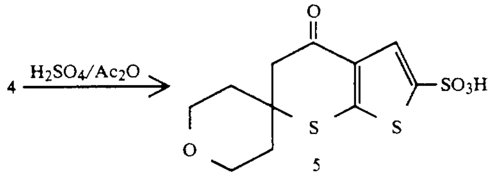

5

A mixture of 4 (2.4 g, 0.01 mol), $CH_2Cl_2$(20 ml) and acetic anhydride (2.8 ml, 3.0 g, 0.03 mol) was cooled in an ice bath and $H_2SO_4$(0.6 ml, 1.1 g, 0.01 mol) was added dropwise. After 0.5 hours at 0°-4° C., the mixture was stirred at room temperature. After 2 hours, the solid was filtered off to yield 2.79 g (85%) of 5.

Step F:

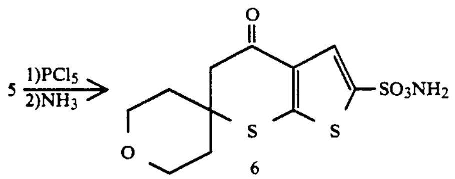

6

To a cooled solution (−20° C.) of (13.5 g, 0.042 mol) in $CH_2Cl_2$ (55 ml.) was added dropwise under $N_2$ a solution of $PCl_5$ (13.8 g, 0.66 mol) in $CH_2Cl_2$ (275 ml). After 0.5 hours at −20° C., the mixture was stirred at room temperature for 1 hour. The reaction was then poured into $H_2O$ (0°–4° C.), separated and the aqueous layer further extracted with $CH_2Cl_2$ (2×). The organic extracts were dried, filtered and concentrated to dryness. The residue was dissolved in acetone and added to a concentrated aqueous ammonia solution. After 1 hour, acetone was removed under reduced pressure, the remaining aqueous phase was acidified and extracted with ethyl acetate (5×). The organic extract was dried, filtered and concentrated to dyrness. The residue was chromotographed on silica gel on a Still column and the product eluted with 50% ethyl acetate/hexane to yield 5.6 g (42%) of 6.

Step G:

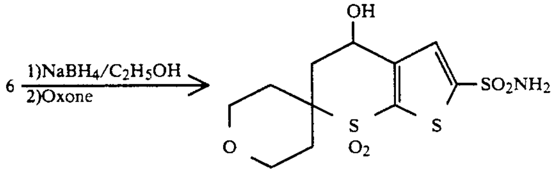

7

A mixture of b (5.6 g, 0.018 mol) and $NaBH_4$ (1 g, 0.026 mol) in absolute ethanol (200 ml) was heated at reflux for 1 hour. After stirring overnight at room temperature, the ethanol was removed under reduced pressure. The residue was trated with $H_2O$ and the pH of the solution adjusted to 8.5. The aqueous phase was extracted with ethyl acetate (3×) and the organic extracts here dried, filtered and concentrated to dryness. The residue was treated with $CH_3OH$ (100 ml) and a solution of Oxone (19 g, 0.031 mol) in $H_2O$ (100 ml) was added dropwise. After stirring at room temperature overnight, the $CH_3OH$ was removed under reduced pressure. The resulting aqueous phase was extracted with ethylacetate (4×) and the orgnaic extracts were dried, filtered and concentrated to dryness. The residue was crystallized from n-$C_4H_9Cl$-$CHCl_3$ to yield 4.8 g, (78%) of 7, mp 180°–2° C.

Analysis calculated for $C_{11}H_{15}NO_6S_3$ Calc'd, N, 3.96; C, 37.38; H, 4.28; Obs, N, 3.94; C, 37.60; H, 4.61.

Step H:

-continued

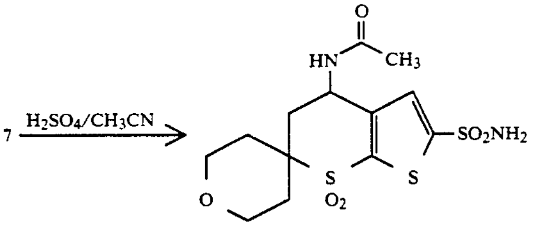

8

Under $N_2$, a solution of 7 (4.5 g, 0.013 mol) in $CH_3CN$ (50 ml) was cooled to −20° C. while concentrated $H_2SO_4$ (7.7 ml, 14.2 g, 0.19 mol) was added dropwise. After addition, the solution was allowed to stir to room temperature. After 18 hours, the reaction was poured onto ice and after 15 minutes, the pH was adjusted to 8.5. The aqueous phase was extracted with ethyl acetate (4×) and the organic extracts were dried, filtered and concentrated to dropwise to yield 1.2 g (25%) of 8.

Step I:

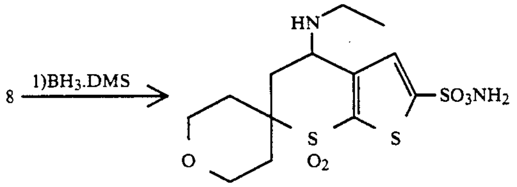

9

Under $N_2$, a suspension of 8 (1.2 g, 0.003 mol) in THF (50 ml) was treated dropwise with borane dimethyl sulfide (10M, 105 ml, 0.015 mol). After addition, the mixture was heated at 60° C. with a short path distillation head to collect dimethylsulfide. After 1.5 hours, the mixture was concentrated to dryness. The residue was treated carefully with 12N HCl (40 ml) and then heated at reflux. After 1.5 hours, the solution was stirred at room temperature overnight and then concentrated to dryness. The residue was chromatographed on silica gel on a Still column (60 mm) and the product eluted with 10% $CH_3OH$-$CHCl_3$-1% aq. $NH_3$ to yield 0.9 g, of crude product. The material was crystallized as the hydrochloride salt from $CH_3OH$-i-$C_3H_7OH$ to yield 0.7 g (56%) of 9; mp 280°–282° C.

Analysis calculated for $C_{13}H_{12}N_2O_5S_3$.HCl. Calc'd, N, 6.72; C, 37.44; R, 5.08; Obs, N, 6.42; C, 37.80; H, 4.91.

EXAMPLE 2

5,6-Dihydro-6-(2-ethoxyethyl)-4-ethylamino-4H-thieno-[2,3-b]thiopyran-2-sulfonamide-7,7-dioxide Step A: Preparation of 3-(2-thienylthio)glutaric acid.

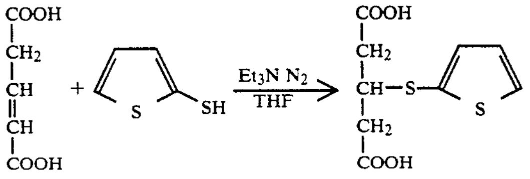

10

To a stirred solution of glutaconic acid (50.0 g, 0.43 mol) in dry tetrahydrofuran (500 ml) under nitrogen was added triethylamine (130 ml, 0.90 mol) followed by 2-thiophenethiol (50.0 g, 0.43 mol). The mixture was stirred at room temperature over the weekend. The mixture was concentrated in vacuo and the residual oil was poured into cold 6N HCl (600 ml). This was extracted with ethyl acetate (200 and 4×100 ml). The combined extracts were washed free of strong acid using saturated sodium chloride, dried, filtered and concentrated in vacuo. The product, 10, was a beige solid (103.4 g), m.p. 119°-123° C. Yield was 98%.

Step B: Preparation of 5, 6-dihydro-4H-4-oxothieno-[2, 3-b]thiopyran-6-acetic acid hydrochloride

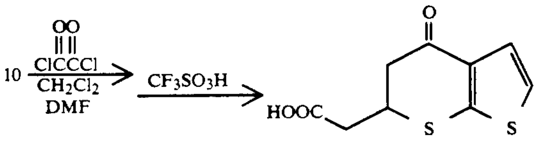

11

To a stirred suspension of 3-(2-thienylthio) glutaric acid (103.4 g, 0.42 mol) in dry methylene chloride (400 ml) was added dimethylformamide (3 ml) followed by the dropwise addition of oxalyl chloride (87 ml, 1.0 mol) added over 1¼ hours. The resulting solution was stirred for 2½ hours at room temperature and then was concentrated in vacuo. The residual oil was taken up in dry methylene chloride (350 ml) and the solution was cooled to −78° C. Trifluoromethanesulfonic acid (74.3 ml, 0.84 mol) was added dropwise over ½ hour and stirring was continued for ¼ hour at −78° C. Then the temperature was allowed to rise to 15° C. over 1¼ hours and the mixture was poured into ice and water (1500 ml). This mixture was stirred overnight under nitrogen in an open beaker. The semi-solid which had formed was separated by decanting the aqueous solution. The solid remaining was stirred in ether (800 ml) and a tan solid formed. The solid was dissolved in ethyl acetate and the combined ether-ethyl acetate solutions were washed free of strong acid with saturated sodium chloride, dried, filtered and concentrated in vacuo. The product 11 was a tan solid (93.8 9), mp 112°-117° C. Yield was Step C: Preparation of Ethyl 5, 6-dihydro-4-oxo-4H-thieno[2, 3-b]thiopyran-6-acetate

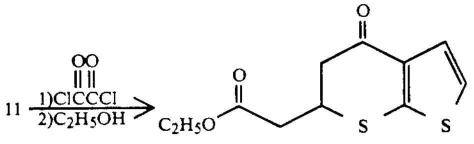

12

5,6-Dihydro-4-oxo-4H-thieno[2,3-b]thiopyran-6-acetic acid (78.0 g, 0.34 mol) was stirred in dry methylene chloride (450 ml) containing dimethylformamide (½ ml) and oxalyl chloride (45 ml, 0.51 mol) was added dropwise over 20 minutes. The mixture was stirred at room temperature for 3 hours and then was concentrated in y&M. The residual oil was taken up in ice cold ethanol (200 ml). The solution was stirred at room temperature for 2 hours and was concentrated in vacuo. The residual oilwas taken up in ethyl acetate and was washed with saturated sodium bicarbonate, saturated sodium chloride and was dried, filtered and concentrated in v to give 72.2 g, of the liquid ester. Crude yield was 83%.

Step D: Preparation of Ethyl 5, 6-dihydro-4-hydroxy-4H-thieno[2, 3-b]thiopyran-6-acetate

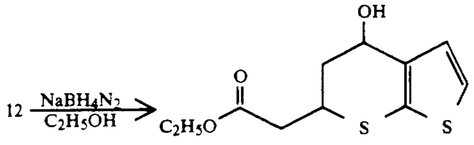

13

To a stirred solution of ethyl 5,6-dihydro-4-oxo-4H-thieno[2,3-b]thiopyran-6-acetate (72.2 g, 0.28 mol) in ethnaol (300 ml) under nitrogen and cooled to 0° C. was added sodium borohydride (2.65 g, 0.07 mol). The mixture was stirred for 1½ hours at 0° C. and then additional sodium borohydride (1.32 g, 0.035 mol) was added. Stirring was continued for 2 hours at room temperature. Acetone (25 ml) was added and the mixture was concentrated in vacuo. The residual oil was dissolved in ethyl acetate (350 ml), washed with saturated sodium chloride, dried, filtered and concentrated in vacuo. The residual oil was purified by chromatography on silica gel (300 g) using 70:30 hexane:ethyl acetate. The alcohol was recovered as a yellow solid (48 g). Yield was 66%.

Step E: Preparation of Ethyl 5,6-dihydro-4-methoxyethoxymethoxy-4H-thieno[2,3-b]thiopyran-6-acetate

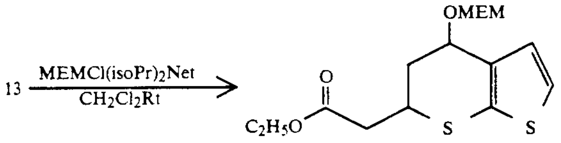

14

Ethyl 5,6-dihyro-4-hydroxy-4H-thieno[2,3-b]-thiopyran-6-acetate (38.6 g, 0.15 mol) was dissolved in dry methylene chloride (200 ml) and diisopropylethylamine (21.3 g, 0.165 mol) was added with cooling followed by MEM chloride (20.6 g, 0.165 mol). The mixture was stirred at room temperature overnight. Then water (300 ml) was added. The aqueous layer was extracted with methylene chloride. The methylene chloride solutions were combined, washed with saturated sodium bicarbonate and water, dried, filtered and concentrated in vacuo. The MEM ether was obtained as a liquid (48.6 g). Yield was 93%.

Step F: Preparation of 5,6-dihydro-6-(2-hydroxyethyl)-4-methoxyethoxymethoxy-4H-thieno-[2,3-b]thiopyran

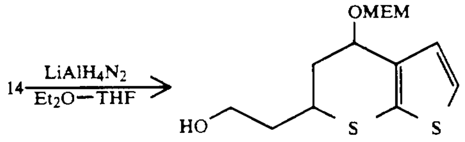

15

To a stirred suspension of lithium aluminum hydride (7.9 g, 0.21 mol) under nitrogen in anhydrous ether (300 ml) cooled to 0° C. was added dropwise over ¾ hours ethyl 5,6-dihydro-4-methoxyethoxymethoxy-4H-thieno[2,3-b]thiopyran-6-acetate (48.6 g, 0.14 mol) in dry tetrahydrofuran (150 ml). The mixture was stirred at 0° C. for 1 hour and at room temperature for 2 hours. Then it was cooled to 0° C. and was decomposed by adding carefully dropwise water (6 ml), 10% sodium hydroxide (8 ml) and water (16 ml). The mixture was filtered and the solids were washed with ether and tetrahydrofuran. The filtrate and washings were combined, dried, filtered and concentrated in vacuo. The product was a yellow liquid (40.3 g). Yield was 95%.

Step G: Preparation of 5,6-dihydro-6-(2-ethoxyethyl)-4-methoxyethoxymethoxy)-4H-thieno[2,3-b]thiopyran

15

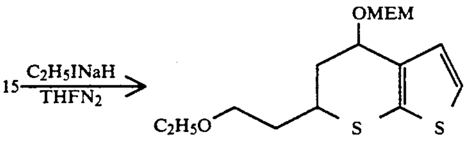

16

Sodium hydride (7.8 g, 0.163 mol of 50% dispersion in mineral oil) was washed free of mineral oil using petroleum ether under nitrogen and was suspended in dry tetrahydrofuran (50 ml). The suspension was coolded to 0° C. and was stirred as 5,6-dihydro-6-(2-hdyroxyethyl)-4-methoxyethoxymethoxy-4H-thieno[2,3-b]thiopyran,(40.0 g, 0.13 mol) dissolved in dry tetrahydrofuran (150 ml) was added over ½ hour. The mixture was stirred at 0° C. for an additional ½ hour and then at 35° C. for ¾ hours. Ethyl iodide (20.8 ml, 0.26 mol) was added and the mixture was stirred overnight at 65° C. Additional ethyl iodide (20 ml and 10 ml) was added over a 12 hour reflux period to complete the reaction. The mixture was concentrated in vacuo. The oil-solid residue was taken up in ether (200 ml) and was washed with water, dried, filtered and concentrated in vacuo to obtain an amber oil (40.0g). Crude yield 93%.

Step H: Preparation of 5,6-dihydro-6-(2-ethoxyethyl)-4-methoxyethoxymethoxy-4H-thieno[2,3-b]thiopyran-2-sulfonamide

16

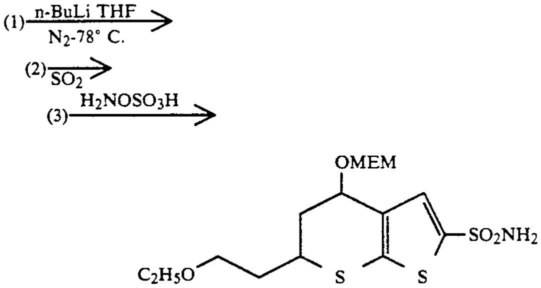

17

5,6-Dihydro-6-(2-ethoxyethyl)-4-methoxyethoxymethoxy-4H-thieno[2,3-b]thiopyran (13.9 g, 0.042 mol) was dissolved in dry tetrahydrofuran (100 ml) and the solution was cooled to −78° C. under nitrogen. Then n-butyl lithium (20 ml, 0.05 mol of 2.5M in hexane) was added dropwise over ½ hour. The solution was stirred at −78° C. for an additional hour. Then anhydrous $SO_2$ was passed over the surface at −78° C. to −40° C. until the mixture became acidic. Stirring at −40° to −78° C. was continued for 2¼ hours and then to room temperature over ½ hour. The solution was then concentrated in vacuo. The residual lithio salt was dissolved in water (75 ml) containing sodium acetate (9.8 g, 0.12 mol) and the solution was cooled to 0° C. Hydroxylamine-O-sulfonic acid (11.3 g, 0.10 mol) was added and the mixture was stirred at room temperature overnight. The reaction mixture was diluted with saturated sodium bicarbonate (100 ml) and ethyl acetate (200 ml). The aqueous layer was separated and extracted with ethyl acetate. The ethyl acetate solutions were combined, washed with water, dried, filtered and concentrated in vacuo to a pale tan solid (15.8 g). Yield 91%. Recrystallization from ethanol gave material with mp 99°-101° C.

Step I: Preparation of 5,6-dihydro-6-(2-ethoxyethyl)-4-methoxyethoxymethoxy-4H-thieno[2,3-b]thiopyran-2-sulfonamide-7,7-dioxide

17

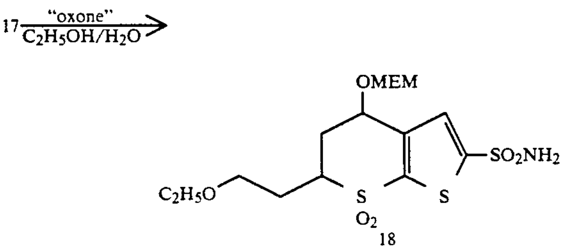

18

5,6-Dihydro-6-(2-ethoxyethyl)-4-methoxyethoxymethoxy-4H-thieno[2,3-b]thiopyran-2-sulfonamide (28.3 g, 0.069 mol) was dissolved in ethanol (300 ml) with warming and water (150 ml) was added. "Oxone"® (6.79 g, 0.11 mol) was added and the mixture was stirred at room temperature for 4¾ hours. Then the mixture was cooled in ice and sodium bicarbonate was added portionwise until the mixture became basic. The mixture was filtered and the solids were washed with ethanol and ethyl acetate. The combined filtrate and washings were concentrated in vacuo. Ethyl acetate (400 ml) was added to the residue with a minimum amount of water to dissolve the remaining salts. The ethyl acetate was separated, dried, filtered and concentrated in vacuo to a pale yellow oil (28.5 g). Yield was 93%.

Step J: Preparation of 5,6-dihydro-6-(2-ethoxyethyl)-4-hydroxy-4H-thieno[2,3-b]thiopyran-2-sulfonamide-7,7-dioxide

18

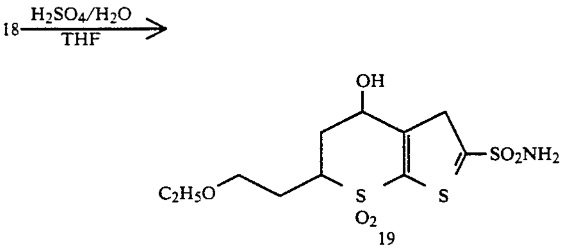

19

5,6-Dihydro-6-(2-ethoxyethyl)-4-methoxyethoxymethoxy-4H-thieno[2,3-b]thiopyran-2-sulfonamide-7,7-dioxide (28.4 g, 0.064 mol) was dissolved in tetrahydrofuran (50 ml) and a 50/50 (volume/volume) solution of sulfuric acid/water (100 ml) was added. The solution was stirred at room temperature for 2½ hours. Then the solution was carefully poured into sodium bicarbonate (200 g), ice, and water (100 ml). Then ethyl acetate (300 ml) was added and the mixture was filtered. The solids were washed with ethyl acetate. The aqueous layer was separated and was extracted with ethyl acetate. The ethyl acetate solutions were combined, washed with saturated sodium chloride, dried, filtered and concentrated in vacuo to an amber oil (23.0 g). This material was not pure but was used without further purification.

Step K: Preparation of 4-acetamido-5,6-dihydro-6-(2-ethoxyethyl)-4H-thieno[2,3-b]thiopyran-2-sulfonamide-7,7-dioxide 19
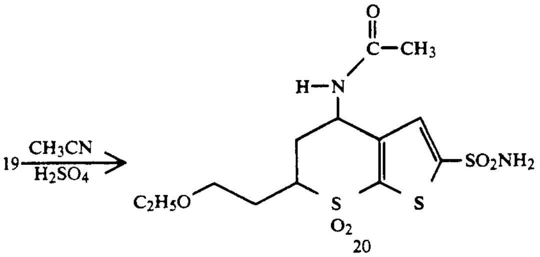

20

To a stirred solution of 5,6-dihydro-6-(2-ethoxyethyl)-4-hydroxy-4H-thieno[2,3-b]thiopyran-7,7-dioxide (12.3 g, 0.035 mol) in dry acetonitrile (100 ml) under nitrogen and cooled to −10° C. was added dropwise over ½ hour concentrated sulfuric acid (9.3 ml, 0.175 mol). The solution was stirred for 3 hrs at −10° C. and then from −10° C. to room temperature overnight. The mixture was cooled to −10° C. and another 9.3 ml of sulfuric acid was added and stirring at room temperature was continued overnight to complete the reaction. Then the solution was poured into ice and water (200 ml) and was extracted with ethyl acetate (150 and 2×50 ml). The combined ethyl acetate extracts were washed with saturated sodium chloride, saturated sodium bicarbonate and again with saturated sodium chloride, dried, filtered and concentrated in vacuo to a tan foam (6.8 g). Yield was 49%.

Step L: Preparation of 5,6-dihydro-6-(2-ethoxyethyl)-4-ethylamino-4H-thieno[2,3-b]thiopyran-2-sulfonamide-7,7-dioxide 20
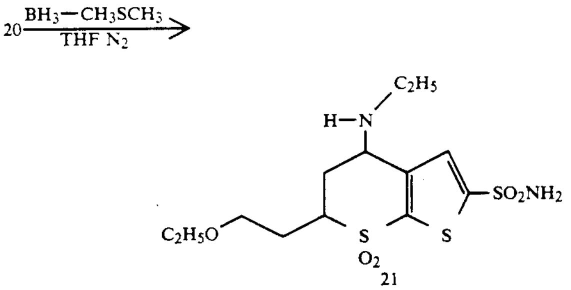

21

To a stirred solution of 4-acetamido-5,6-dihydro-6-(2-ethoxyethyl)-4H-thieno[2,3-b]thiopyran-2-sulfonamide-7,7-dioxide (6.8 g, 0.017 mol) in tetrahydrofuran (20 ml) heated under nitrogen to reflux was added borane-methyl sulfide (17 ml, 0.170 mol) dropwise over ½ hr. The reaction was heated at reflux for 2 hr. while allowing the methyl sulfide to distill off. Then the mixture was concentrated in vacuo to a yellow gum. Then 6N HCl (30 ml) was added followed by water (30 ml) and the mixture was heated on the steam bath for ½ hour. The solution was basified with excess sodium bicarbonate and was extracted with ethyl acetate (300 ml). The aqueous solution was again extracted with ethyl acetate. The combined extracts were washed with saturated sodium chloride, dried, filtered and concentrated in vacuo to obtain a white foam (5.3 g) mixture of cis and trans isomers. Chromatography on silica gel gave 2.28 g of the a-isomer and 0.17 g of the β-isomer.

a-isomer (trans)

The hydrochloride of the a-isomer was prepared by dissolving 0.19 g of the a-isomer in ethanol (3 ml) and adding 6N ethanolic HCl (0.1 ml). The white HCl salt (0.21 g), mp. 135°-138° C. was collected by filtration.

β-isomer (cis)

The hydrochloride of the β-isomer was prepared by dissolving 2.44 g of the β-isomer in ethanol (15 ml) and adding 6N ethanolic HCl (1.2 ml). The white solid (2.0 g), mp dec. >128° C. was collected by filtration.

EXAMPLE 3

Enantiomers of 5,6-dihydro-6-(2-ethoxyethyl)-4-ethylamino-4H-thieno-[2,3-b]thiopyran-2-sulfonamide-7,7-dioxide Step A: Preparation of the trans, (−) rotatory enantiomer 21(trans-isomer)
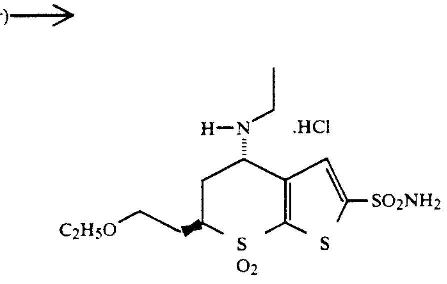

21 (trans-isomer)
(−) rotatory enantiomer

The trans-isomer racemate (3.37 g, 0.009 mol) was dissolved in acetonitrile (50 ml) at reflux and di-p-toluoyl-D-tartaric acid monohydrate (0.88 g, 0.002 mol) was added. The solution was left overnight. Then it was cooled and filtered to obtain 1.4 g. This material was recrystallized from acetonitrile and 1.16 g of the pure salt was recovered, mp 179°-181° C. dec. $[a]_D^{25}=(+)$ 34.8 ($CH_3OH$).

The free base was prepared by shaking the salt with ethyl acetate (25 ml) and saturated sodium bicarbonate (10 ml). The ethyl acetate solution was washed with saturated sodium chloride, dried, filtered and concentrated in vacuo to obtain 0.78 g of colorless oil which solidlied to a white solid, mp 123°-125° C. $[a]_D^{25}=(-)$ 23.4 ($CH_3OH$).

The hydrochloride salt was prepared by dissolving 0.74 g of the free base in warm ethanol (10 ml) and adding 0.33 ml of 6N ethanolic HCl. Then the solution was diluted with an equal volume of ether. After cooling the mixture was filtered to yield 0.74 g of white solid, mp 185°-187.5° C. dec. a]D $]_D^{25}=(-)$ 5.5 ($CH_3OH$)

Step B: Prepaaration of the trans, (+) rotatory enantiomer 21 (trans-isomer)

-continued

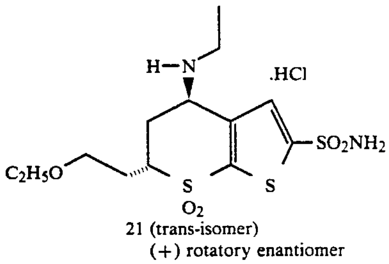

21 (trans-isomer)
(+) rotatory enantiomer

The trans-isomer enriched in the (+) rotatory enantiomer (1.0 g, 0.0026 mol) was dissolved in hot acetonitrile (10 ml) and di-p-toluoyl-L-tartaric acid monohydrate (0.48 g, 0.0012 mol) was added. The solution was left at room temperature overnight. Then the mixture was cooled and filtered to obtain 0.8 g, of salt, mp 175°-177° C. which upon recrystallization from acetonitrile gave 0.57 g, mp 178°-1800C.

$[a]_D^{25}=(-)$ 34.8 ($CH_3OH$).

The free base was prepared by shaking this material with ethyl acetate (25 ml) and saturated sodium bicarbonate. The ethyl acetate extract was washed with saturated sodium chloride, dried, filtered and concentrated in to a viscous oil which solidified to a white solid (0.42 g), mp 123°-1250C. $[a]_D^{25}=(+)$ 23.4 ($CH_3OH$).

The hydrochloride salt -Was prepared by dissolving 0.35 g of the free base in ethanol (7 ml) and adding 6N ethanolic HCl (0.16 ml). Dilution with an equal volume of ether and refrigeration yielded a white solid (0.39 g), mp. 185°-188° C. dec.

$[a]_D^{25}=(+)$ 5.2 ($CH_3OH$).

Step C: Preparation of the cis (+) rotatory enantiomer.

21 (cis-isomer)

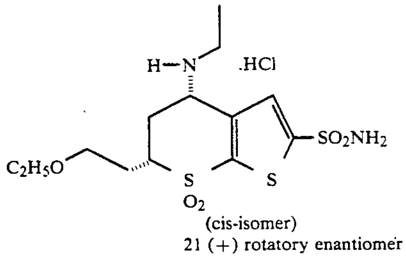

(cis-isomer)
21 (+) rotatory enantiomer

The cis-isomer racemate (1.3g, 0.0034 mol) was dissolved in acetonitrile (10 ml) and di-p-toluoyl-D-tartaric acid (0.34g, 0.00084 mol) was ac ded. Solid precipitated immediately. The salt was redissolved by refluxing with 40 ml of acetonitrile and 10 ml of ethanol and was left to crystallize slowly overnight. Filtration gave 0.6 g. of the salt. Recrystallization from acetonitrile gave 0.46 g of the pure salt, mp 209°-209-5° C., with decomposition.

The free base was prepared by shaking 0.87 g (0.667 mmol) of the salt with 10 ml of saturated sodium bicarbonate and extracting with 25 and 2×15 ml of ethyl acetate. The combined ethyl acetate extracts were washed with saturated NaCl solution, dried, filtered and concentrated in vacuo at room temperature. There was recovered 0.52 g of the free base as a colorless oil.

The hydrochloride salt was prepared using ethanolic hydrogen chloride in ethanol (7 ml) and there was obtained 0.44 g of white solid, mp 198°-202° C.

$[a]_D^{25}=(+)$ 57.64 ($CH_3OH$)

Step D: Preparation of the cis (−) rotatory enantiomer.

21 (cis-isomer)

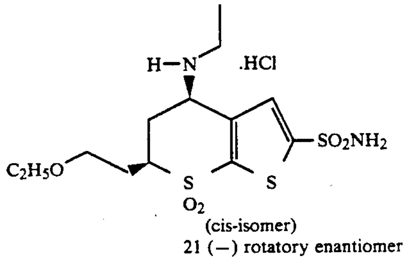

(cis-isomer)
21 (−) rotatory enantiomer

The cis-isomer enriched in the (−) rotatory enantiomer (0.82 g and containing 0.0017 mol of the (−) rotatory enantiomer) was dissolved in acetonitrile (10 ml) and di-p-toluoyl-L-tartaric acid (0.34 g, 0.00085 mol) was added. An immediate precipitation occurred. The mixture was heated with 40 ml of acetonitrile and 15 ml of methanol and the solution was left to crystallize slowly overnight. The mixture was filtered and 0.47 g of white solid was recovered, mp 214°-215.5° C., with decomposition. A second crop of 0.38 g was obtained which was recrystallized from 10 ml of acetonitrile —$H_2O$ (1:) to give 0.24 g, mp 212°-213° C.

The free base was prepared by dissolving 0.71 g of the diastereomeric salt in 15 ml of saturated sodium bicarbonate and 15 ml of ethyl acetate. The ethyl acetate was separated and the aqueous phase was reextracted with 2×15 ml of ethyl acetate. The ethyl acetate extracts were combined and washed with saturated NaCl, dried, filtered and concentrated in vacuo at room temperature. The free base was obtained as a white solid, 0.45 g.

The hydrochloride salt was prepared by dissolving 0.45 g of the free base in 7 ml of hot ethanol and adding a slight excess of ethanolic hydrogen chloride/ether (10 ml) was added and the white solid was collected: 0.39 g, mp 198°-202° C.

$[a]_D^{25}=(-)$ 58.3 ($CH_3OH$)

EXAMPLE 4

Trans and cis 5,6-dihydro-6-ethoxymethyl-4-ethylamino-4H-thieno-[2,3-b]thiopyran-2-sulfonamide-7,7-dioxide Step A: Preparation of 2-(2-thienylthio)succinic acid

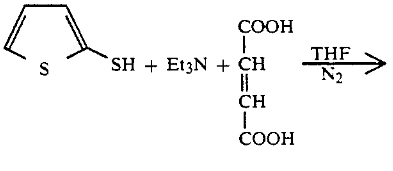

-continued

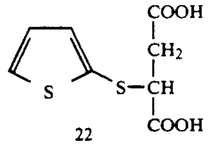

22

To a stirred solution of maleic acid (6.38 g, 0.055 mol) in tetrahydrofuran (50 ml) under a nitrogen atmosphere was added 2-thiophenethiol (5.0 ml, 0.055 mol) and triethylamine (14.2 g, 0.14 mol). The mixture was stirred at gentle reflux for 16 hours overnight. The solvent was removed in vacuo and the residual oil was poured into 3N HCl (200 ml). The product was extracted into ethyl acetate (125 ml) in three portions, washed with saturated NaCl solution and dried over $Na_2SO_4$. The solution was filtered and concentrated in vacuo to give the product as a light beige solid, 11.9 g, mp 136°-138.5° C. of 95% purity by HPLC. Yield was 93%.

Step B: Preparation of 5,6-dihydro-4-oxo-4H-thieno [2,3-b]thiophene-6-carboxylic acid

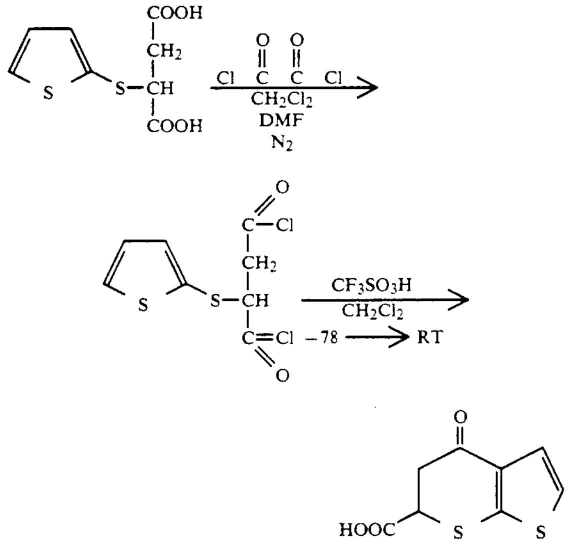

23

To a stirred suspension of 2-(2-thienylthio) succinic acid (75.5 g, 0.325 mol) in methylene chloride (500 ml) under nitrogen atmosphere was added dimethylformamide (3 ml) followed by the dropwise addition of oxalyl chloride (70.7 ml, 0.81 mol) over a ½ hour period. The mixture was stirred at ambient temperature for 2½ hours and the resulting solution was concentrated in to a brown oil. Then ½ of this oil was dissolved in methylene chloride (200 ml), cooled to about −78° C. and stirred as trifluoromethanesulfonic acid (50 g, 0.33 mol) was added dropwise over 5 minutes. After ¼ hour at −78° C., the cooling bath was removed and the temperature was allowed to rise to room temperature. After 4¾ hours, the mixture was poured into ice and water. Methylene chloride (400 ml) was added and filtered to obtain product as a pale gray solid (4.1 g). The methylene chloride layer was separated, washed with $H_2O$, dried over $Na_2SO_4$, filtered and concentrated in vacuo to a black gum. The gum was dissolved in ethyl acetate (150 ml). This solution was extracted with 10×50 ml of 0.25N KOH. The individual extracts were acidified and solids were filtered and dried. Total product obtained was 19 g or 55% yield. Pure product melted at 182.5°-184° C.

Step C: Preparation of N,N-dimethyl-4-oxo-4H-thieno[2,3-b]thiopyran-6-carboxamide

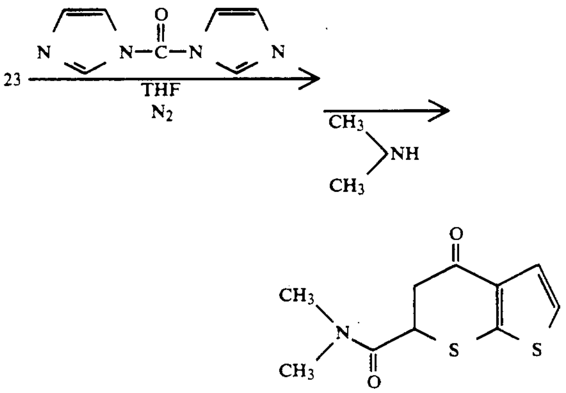

24

The reaction was run under a nitrogen atmosphere. To a stirred solution of 4-oxo-4H-thieno[2,3-b]thiopyran-6-carboxylic acid (10.7 g, 0.05 mol) in tetrahydrofuran (50 ml) was added carbonyldiimidazole (8.9 g., 0.055 mol). The mixture was stirred at ambient temperature for ¾ hours. Anhydrous dimethylamine was bubbled into the thick suspension at 0° C. until an excess was present. The resulting solution was stirred at 0° C. for ¾ hours and the solvent was removed in vacuo. The residual oil was diluted with $H_2O$ (50 ml) and the solid which separated was filtered and dried to give 7.14 g of product, mp 126.5°-128°, of 97% purity by HPLC. The aqueous filtrate was concentrated in and the residual gum was chromatographed on silica gel (200 g) using 10% methanol in chloroform. An additional 3.15 g of impure product was recovered. Yield was about 80%.

Step D: Preparation of 5,6-dihydro-N,N-dimethyl-4-hydroxy-4H-thieno[2,3-b]thiopyran-6-carbox-amide

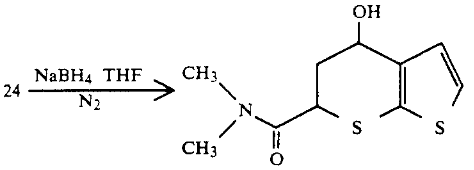

25

5,6-Dihydro-N,N-dimethyl-4-oxo-4H-thieno-[2,3-b]thiopyran-6-carboxamide (26.2 g, 0.109 mol) was stirred in tetrahydrofuran (250 ml) at room temperature under nitrogen and sodium borohydride (8.25 g, 0.218 mol) was added. The mixture was stirred at ambient temperature for 4 hours. Then it was cooled in ice and ethyl acetate (100 ml) was added followed by the dropwise addition of 3N HCl (100 ml). The aqueous layer was separated and extracted with ethyl acetate (50 ml). The combined organic solutions were washed with saturated sodium chloride and saturated sodium bicarbonate, dried over $NaSO_4$, filtered and concentrated in at room temperature. The product, 25, was essentially pure by TLC. Yield was quantitative.

Step E: Preparation of 5,6-dihydro-N,N-dimethyl-4-methoxyethoxymethoxy-4H-thieno[2,3-b]thiopyran-6-carboxamide

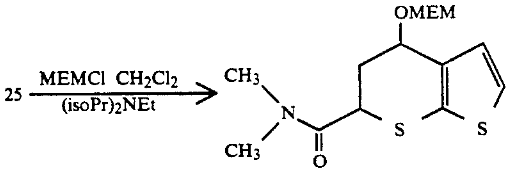

26

To a stirred solution of 5,6-dihydro-N,N-dimethyl-4-hydroxy-4H-thieno[2,3-b]thiopyran-5-carboxamide, 25, (63.4 g, 0.26 mol) in methylene chloride 500 ml) was added dissopropylethylamine (40.3 g, 0.312 mol) followed by MEM chloride (38.9 g, 0.312 mol). The mixture was stirred at ambient temperature overnight. The dark solution was poured into ice and water (500 ml). The aqueous layer was separated and was extracted with methylene chloride (100 ml). The methylene chloride solutions were combined, washed with cold 1.5N $HC_1$, saturated $NaHCO_3$, and water, dried, filtered and concentrated in at room temperature. A dark amber oil was obtained which solidified to a brown solid upon standing. Crude yield of 26 was 79.7 g (92%).

Step F: Preparation of 5,6-dihydro-6-dimethylamino-methyl-4-methoxyethoxymethoxy-4H-thieno-[2,3-b]thiopyran

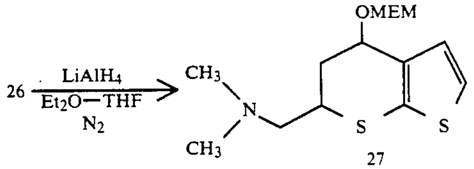

27

To a stirred suspension of lithium aluminum hydride (11.4 g, 0.20 mol) in anhydrous ether (200 ml) under nitrogen and cooled in ice was added a solution of 5,6-dihydro-N,N-dimethyl-4-methoxyethoxymethoxy-4H-thieno[2,3-b]thiopyran-6-carboxamide (80 g, 0.28 mol), 26, in dry tetrahydrofuran (150 ml) dropwise over 1½ hours. Stirring was continued at ice bath temperature overnight. The suspension was cooled in ice and quenched under nitrogen by adding dropwise water (12 ml), 20% sodium hydroxide (9 ml) and water (42 ml). Then additional ether (100 ml) was added and the mixture was filtered. The solids were washed with ether and ethyl acetate. The filtrate and washing were washed with saturated sodium chloride (3×50 ml), dried over $Na_2SO_4$, filtered and concentrated in vacuo at room temperature. A viscous oil was obtained (66.9 g). Crude yield of 27 was 88%.

Step G: Preparation of 5,6-dihydro-6-dimethylamino-methyl-4-methoxyethoxymethoxy-4H-thieno-[2,3-b]thiopyran-2-sulfonamide

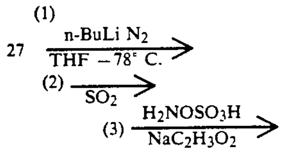

-continued

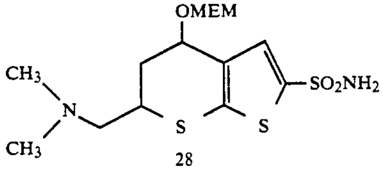

28

5,6-Dihydro-6-dimethylaminomethyl-4-methoxyethoxymethoxy-4H-thieno[2,3-b]thiopyran, 27 (66.9 g, 0.21 mol) was dissolved in dry tetrahydrofuran (400 ml) under nitrogen and the solution was cooled to −78° C. Then n-butyl lithium (100.8 ml), 0.252 mol of 2.5 M in hexane) was added dropwise with stirring over 1½ hours. Stirring was continued for another 1½ hours at −78° C. and then anhydrous $SO_2$ was bubbled over the surface of the solution until the mixture became acidic (about 1 hour). The mixture was stirred at −78° C. for 2 hours and then warmed to room temperature over ½ hour. The resulting solution was concentrated in vacuo to remove excess $SO_2$ and tetrahydrofuran. The residual lithio salt was taken up in water (300 ml) containing sodium acetate (58.4 g, 0.59 mol). Hydoxylamine-O-sulfonic acid (59.4 g, 0.525 mol) was added followed by additional sodium acetate (16 g, 0.2 mol) to adjust to pH 5.0. The mixture was stirred at room temperature overnight and then was cooled in ice, basified with sodium bicarbonate and filtered. The filtrate was extracted with 20% methanol-chloroform (500 and 2×200 ml) and the solids were washed free of product with 20% methanol-chloroform. These solutions were combined, washed with saturated sodium chloride, dried, filtered and concentrated in vacuo. The product was obtained as an oil (70.9 g). Yield of 28 was 85%. Recrystallization from ethanol gave material with mp 132°-134° C.

Step H: Preparation of 5,6-dihydro-6-methylene-4-methoxyethoxymethoxy-4H-thieno[2,3-b]thiopyran-2-sulfonamide-7,7-dioxide

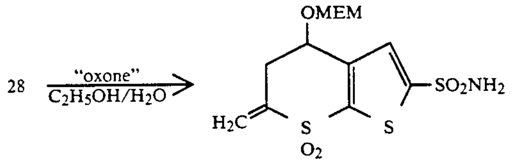

30

5,6-Dihydro-6-dimethylaminomethyl-4-methoxyethoxymethoxy-4H-thieno[2,3-b]thiopyran-2-sulfonamide (39.7 g, 0.10 mol) was dissolved in ethanol (300 ml) with warming. The solution was diluted with water (150 ml), cooled to 20° C. and Oxone® (92.2 g, 0.15 mol) was added. The mixture was stirred at ambient temperature for 3 hours. Additional Oxone® (25 g, 0.04 mol) was added and stirring was continued for 1½ hours. Then the mixture was neutralized by pouring into ethyl acetate (300 ml) and sodium bicarbonate (82 g, 1.0 mol). The mixture was filtered and the solids were washed with ethyl acetate. The filtrate and washing were concentrated in vacuo at room temperature. The oily residue was taken up in ethyl acetate and the solution was washed with saturated sodium bicarbonate and saturated sodium chloride, dried, filtered and concentrated in vacuo at room temperature. The product was a viscous amber oil (31.4 g). Yield of 30 was 82%

Step I: Preparation of 5,6-dihydro-6-ethoxymethyl-4-methoxyethoxymethoxy-4H-thieno[2,3-b]thiopyran-2-sulfonamide-7,7-dioxide 30
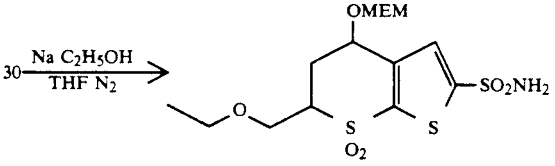

31

Sodium spheres (2.0 g, 0.088 mol) were added to dry ethanol (100 ml) under nitrogen. The mixture was stirred until the sodium had reacted completely (½ hr). This sodium ethoxide solution was added over several minutes to a cold solution of 5,6-dihydro-6-methylene-4-methoxyethoxymethoxy-4H-thieno[2,3-b]thiopyran-2-sulfonamide 30, (15.3 g, 0.04 mol) in tetrahydrofuran (50 ml). The resulting solution was stirred at ambient temperature for 1 hour. Then the mixture was acidified with 6N HCl (15 ml, 0.09 mol) and saturated sodium bicarbonate (25 ml) was carefully added. The basic solution was concentrated in vacuo and the oily residue was taken up in chloroform (150 ml) and water (50 ml). The aqueous layer was separated and extracted with chloroform (2×40 ml). The combined chloroform solutions were washed with water, dried, filtered and concentrated in vacuo. An amber gum was obtained (15.5 g). Yield of was 89%.

Step J: Preparation of 5,6-dihydro-6-ethoxymethyl-4-hydroxy-4H-thieno[2,3-b]thiopyran-2-sulfonamide-7,7-dioxide 31
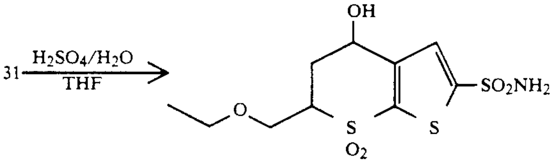

32

5,6-Dihydro-6-ethoxymethyl-4-methoxyethoxymethoxy-4H-thieno[2,3-b]thiopyran-2-sulfonamide-7,7-dioxide, 31, (15.5 g, 0.036 mol) was dissolved in tetrahydrofuran (100 ml) and the solution was stirred at 0° C. as sulfuric acid-water (200 ml of 1/1 volume/volume) was added dropwise over ¾ hour. The mixture was stirred at ambient temperture for 2¾ hours. Then it was poured into ethyl acetate (300 ml), ice and sodium bicarbonate (336 g, 4.0 mol) with stirring. The neutralized mixture was filtered and the solids were washed with ethyl acetate (500 ml). The aqueous layer was separated and was extracted with ethyl acetate (2×75 ml). The combined ethyl acetate solutions were washed with saturated sodium chloride, dried, filtered and concentrated in The product was a pale tan solid foam (10.9 g). Yield of 32 was 89%.

Step K: Preparation of 5,6-dihydro-6-ethoxymethyl-4-ethylamino-4H-thieno[2,3-b]thiopyran-2-sulfonamide-7,7-dioxide (cis and trans isomers)

-continued

32
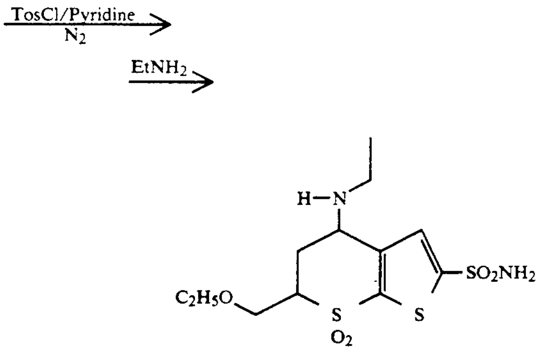

33

5,6-Dihydro-6-ethoxymethyl-4-hydroxy-4H-thieno[2,3-b]thiopyran-2-sulfonamide-7,7-dioxide (4.25 g, 0.0123 mol) was dissolved in dry pyridine (25 ml) and the solution was cooled to −10° C. p-Toluenesulfonyl chloride (5.14 g, 0.027 mol) was added and the mixture was stirred at −10° C. for 5 hours. Anhydrous ethylamine (26 ml, 0.4 mol) was added and the mixture was stirred for 2 hours at room temperature. Finally, 70% ethylamine (32 ml. 0.40 mol) was added and the mixture was heated at 50° C. overnight. The dark mixture was concentrated in vacuo and the residual oil was taken up in ethyl acetate (100 ml) and saturated sodium bicarbonate (100 ml). The aqueous layer was separated and extracted with ethyl acetate. The combined ethyl, acetate solutions were washed with saturated sodium chloride, dried, filtered and concentrated in vacuo. The oil obtained was a 2:1 mixture of cis and trans isomers which were separated by silica gel chromatography using 7.5% methanol-chloroform. Total recovery was 2.43 g. Yield of 33 was 54%.

α-isomer

The less polar trans isomer was a waxy solid. The HCl salt melted at 145°-148° C., dec.

β-isomer

The more polar cis isomer was a white solid, mp. 154°-157° C. The HCl salt melted at 229°-231° C., dec.

EXAMPLE 5

Enantiomers of 5,6-dihydro-6-ethoxymethyl-4-ethylamino-4H-thieno[2,3-b]thiopyran-2-sulfonamide-7,7-dioxide Step A: Preparation of the trans, (−) rotatory enantiomer 33 (trans-isomer)
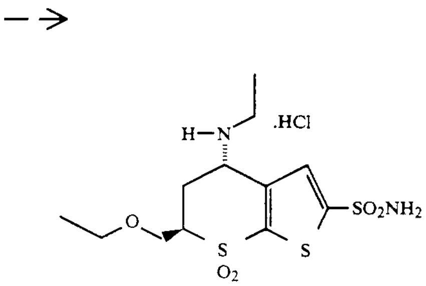

33 (trans-isomer) (−) rotatory enantiomer

Racemic n ((x-isomer)-5,6-dihydro-6-ethoxymethyl-4-ethylamino-4H-thieno[2,3-b]thiopyran-2-sulfonamide-7,7-dioxide (1.15 g, 3.12 mmol) was dissolved in hot acetonitrile (10 ml) and di-p-toluoyl-L-tartaric acid monohydrate (0.325 g, 0.78 mmol) was added. The solution was left at room temperature ovenight. Filtration gave a white solid salt (0.83 g). Three recrystallyzations from acetonitrile gave 0.32 g of pure salt, $[\alpha]_D^{25}=(-)$ 57.5 ($CH_3OH$).

The free base was prepared by shaking 0.76 g of the salt with ethyl acetate (25 ml) and saturated sodium bicarbonate (10 ml). The aqueous layer was separated and extracted with ethyl acetate. The combined ethyl acetate solutions were washed with saturated sodium chloride, dried, filtered and concentrated in vacuo to a colorless oil (0.5 g), $[\alpha]_D^{25}=(-)$ 25.2 ($CH_3OH$).

The oil was converted to the hydrochloride salt by dissolving in ethanol (5 ml) and adding 6N ethanolic HCl (0.22 ml). The mixture was cooled and filtered to obtain the hydrochloride salt as a white solid (0.43 g), mp. 202.5°-204° C., $[\alpha]_D^{25}=(-)$ 1.7 ($CH_3OH$).

Step B: Preparation of the trans, (+) rotatory enantiomer.

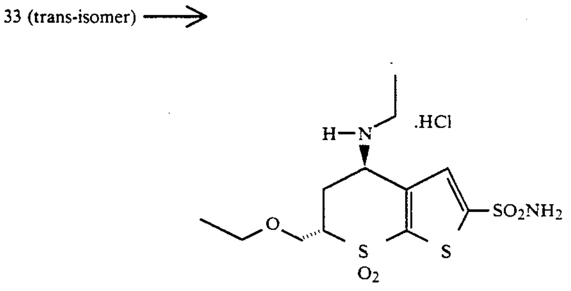

33 (trans-isomer) (+) rotatory enantiomer

The trans-isomer of 5,6-dihydro-6-ethoxy-methyl-4-ethylamino-4H-thieno[2,3-b]thiopyran-2-sulfonamide-7,7-dioxide enriched in the (+)-rotatory enantiomer (0.87 g, 24 mmol) was dissolved in hot acetonitrile (10 ml) and di-p-toluoyl-D-tatric acid (0.48 g, 1.2 mmol) was added. The solution was left at room temperature overnight. Filtration gave a white solid salt (0.65 g). Recrystallization from acetonitrile gave 0.56 g of pure salt;

$[\alpha]_D^{25}=(+)$ 58.5 ($CH_3OH$).

The free base was prepared by shaking the salt in ethyl acetate (25 ml) and saturated sodium bicarbonate (10 ml). The aqueous layer was separated and extracted with ethyl acetate. The combined ethyl acetate solutions were washed with saturated sodium chloride, dried, filtered and concentrated in vacuo to a colorless oil (0.42 g).

The oil was converted to the hydrochloride salt by dissolving in ethanol (7 ml) and adding 6N ethanolic HCl (0.20 ml). The mixture was cooled, diluted with ether (40 ml) and filtered to obtain the hydrochloride salt as a white solid (0.36 g, mp 202°-204° C.; $[a]_D^{25}=(+)$ 1.2 ($CH_3OH$).

EXAMPLE 6

5,6-Dihydro-6-methoxymethyl-4-(n-propylamino)-4H-thieno[2,3-b]thiopyran-2-sulfonamide-7,7-dioxide (trans-isomer, and cis-isomer)

Step A: Preparation of 5,6-dihydro-4-methoxyethoxy-methoxy-6-methoxymethyl-4H-thieno[2,3-b]thiopyran-2-sulfonamide-7,7-dioxide.

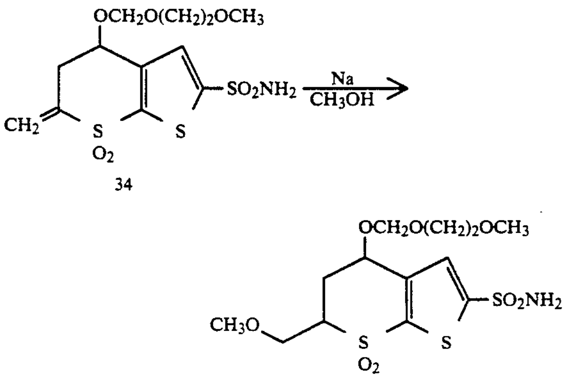

34

35

Sodium (1.7 g, 0.075 m) was added portionwise to absolute methanol (150 ml) under nitrogen with stirring. After solution was effected, the solution was added to 5,6-dihydro-4-methoxyethoxy-methoxy-6-methylene-4H-thieno[2,3-b]thiopyran-2-sulfon amide-7,7-dioxide (12.43 g, 0.032 m) dissolved in methanol (55 ml) with stirring under nitrogen. After 20 hours, the reaction mixture was cooled in ice, acidified with 6N hydrochloric acid (19 ml) and then basified with saturated sodium bicarbonate solution. The mixture was concentrated in vacuo to remove methanol and the aqueous oil suspension was extracted with ethyl acetate (2×150 ml). After washing with saturated sodium bicarbonate solution and with saturated sodium chloride solution and drying over sodium sulfate, the solvent was evaporated in vacuo to yield a viscous oily product weighing 12.40 g (93%) which was used in the next step without further purification.

Step B: Preparation of 5,6-dihydro-4-hydroxy-6-methoxymethyl-4H-thieno[2,3-b]thiopyran-2-sulfonamide-7,7-dioxide.

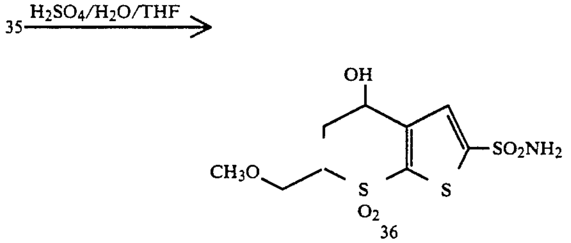

36

A solution of 5,6-dihydro-4-methoxyethoxymethoxy-6-methoxymethyl-4H-thieno[2,3-b]thiopyran-2-sulfonamide-7,7-dioxide (12.4 g, 0.030 m) in tetrahydrofuran (90 ml) was cooled to −5° C. &nd stirred while a solution of concentrated sulfuric acid (90 ml) in water (90 ml) was added dropwise over 45 minutes while maintaining the temperature below 5° C. After stirring at −5° C. for 1 hour and at ambient temperature for 3 hours, the mixture was added to a stirred suspension of sodium bicarbonate (300 g) in ethyl acetate (360 ml) and ice. After 30 minutes with periodic additions of saturated sodium bicarbonate solution to render the mixture basic, it was filtered and the solids were washed thrice with ethyl acetate. The combined filtrate and washings were washed with water, dried over sodium sulfate and evaporated in vacuo to yield 7.79 g, (79%) of amorphous product which was used in the succeeding step without further purification.

Step C: Preparation of trans and cis-5,6-dihydro-6-methoxymethyl-4-(n-propylamino)-4H-thieno[2,3-b]thiopyran-2-sulfoanmide-7,7-dioxide (α-Isomer, and β-Isomer)

36
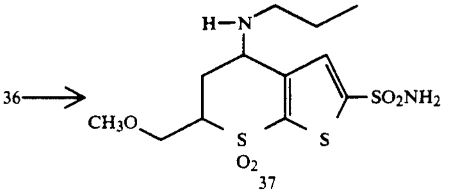
37

A stirred solution of 5,6-dihydro-4-hydroxy-6-methoxymethyl-4H-thieno[2,3-b]thiopyran-2-sulfonamide-7,7-dioxide (3.50 g, 0.011 m) in dry pyridine (25 ml) was cooled to −10° C. under nitrogen while p-toluenesulfonyl chloride (4.77 g, 0.025 m) was added in one portion. After stirring at −10° C. for 5 hours, the mixture was further cooled to −20° C. and n-propylamine (18.3 g, 0.31 m) was added dropwise while maintaining temperature below 0° C. The mixture was stirred at ambient temperature for 1.5 hours and then at 50° C. for 19 hours. The reaction mixture was concentrated in and the residue was distributed between ethyl acetate (200 ml) and saturated sodium bicarbonate solution (100 ml). The aqueous layer was separated and extracted with ethyl acetate (2×100 ml). The combined ethyl acetate extracts were washed twice with water and concentrated to approximately 75 ml in vacuo. The solution was extracted with 3N hydrochloric acid (2×50 ml) and washed with water (50 ml). The combined acid extracts and water wash were basified with sodium bicarbonate and extracted with ethyl acetate (3×250 ml). The combined extracts were washed thrice with water, dried over sodium sulfate and evaporated in to yield a tan solid residue of the mixture of isomers weighing 2.20 g (54%).

The residue was chromtographed on silica gel on a 100 mm diameter Still column, eluting initially with 2900 ml chloroform/methanol/ammonium hydroxide, 95:5:0.5, followed by chloroform/methanol/ammonium hydroxide, 90:10:1 to yield 0.39 g, of the α-isomer (trans-) and 1.00 g of the β-isomer (cis). The trans-isomer (0.39, 0.0011 m) was dissolved in absolute ethanol (10 ml), 4.8 N ethanolic hydrochloric acid (0.3 ml) was added and the solution was diluted to incipient turbidity with anhydrous ether to yield 0.26 g of the hydrochloride salt melting with decomposition at approximately 150° C.

Anal. Calcd. for $C_{12}H_{20}N_2O_5S_3$.HCl: C, 35.39; H, 5.23; N, 6.92; Found C, 35.70; H, 5.28; N, 6.64.

The cis-simmer (1.00 g, 0.0027 m) was dissolved in absolute ethanol (25 ml) and absolute methanol(10 ml) with warming, the solution was concentrated to approximately 15 ml. 4.8 N ethanolic hydrochloric acid (0.8 ml) was added and the solution was diluted to incipient cloudiness with anhdyrous ether to yield 0.81 g of the hydrochloride salt melting at 218°-221° C.

Anal. Calcd. for $C_{12}H_{20}N_2O_5S_3$.HCl: C, 35.39; H, 5.23; N, 6.92; Found C, 35.25; H, 5.26; N, 6.90.

PMR studies showed the α-isomer to have a trans configuration and the β-isomer to be cis

EXAMPLE 7

5,6-Dihydro-6-ethoxymethyl-4-(n-propylamino)-4N-thieno[2,3-b]thiopyran-2-sulfonamide-7,7-dioxide trans-isomer, and cis-isomer)

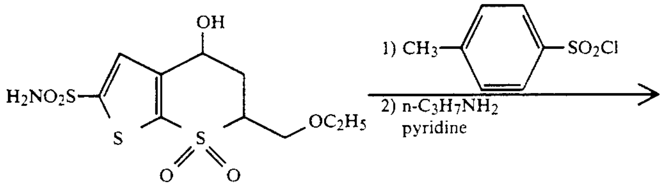

32

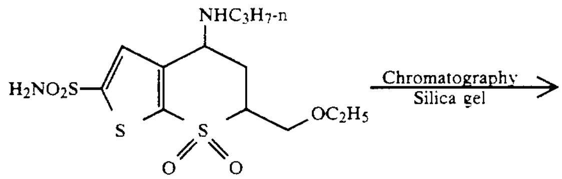

38

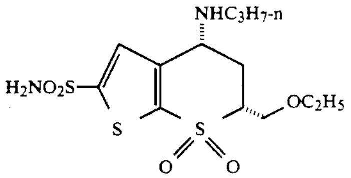
and
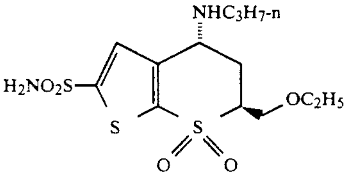
β-Isomer 38 α-Isomer

A stirred solution of 5,6-dihydro-6-ethoxymethyl-4-hydroxy-4H-thieno[2,3-b]thiopyran-2-fulonamide-7,7-dioxide prepared as described in Example 9 for preparation of the corresponding 6-methoxymethyl analog (4.00 g, 0.0017 m) in dry pyridine (25 ml) was cooled to −10° C. undernitrogen while p-toluenesulfonyl chloride (4.96 g, 0.026 m) was added in one portion. After stirring at −10° C. for 5 hours, the mixture was further cooled to −20° C. and n-propylamine (19.6 g, 0.33 m) was added dropwise while maintaining the temperature below 0° C. The mixture was stirred at ambient temperature for 1 hour and then at 50° C. for 18 hours. The reaction mixture was concentrated in vacuo and the residue was distributed between ethyl acetate (200 ml) and saturated sodium bicarbonate solution (100 ml). The aqueous layer was separated and extracted with ethyl acetate (2×100 ml). The combined ethyl acetate extracts were washed with water and concentrated to approximately 75 ml in vacuo. The solution was extracted with 3N hydrochloric acid (2×50 ml) and washed once with water. The combined acid extracts and water wash were basified with sodium bicarbonate and extracted with ethyl acetate (3×250 ml). After washing thrice with water and drying over sodium sulfate, the solvent was evaporated in vacuo to yield a red oily residue of the mixture of isomers weighing 3.18 g (71%).

The oily residue was chromatographed on silica gel on a 100 mm. diameter Still column, eluting initially with 2600 ml of chlorofrom/methanol/ammonium hydroxide, 95:560.5, followed by chloroform/methanol/ammonium hydroxide, 90:10;1. The fractions that contained a mixture of isomers were rechromatographed on an 80 mm, diameter Still column, eluting with chloroform/methanol/ammonium hydroxide, 95:5:0.5, to ultimately yield 0.69 g of the (x-isomer and 1.53 g of the β-isomer.

The α-isomer (0.69 g, 0.0018 m) was dissolved in absolute ethanol (5 ml), 4.8 N ethanolic hydrochloric acid (0.5 ml) was added and the solution was diluted to incipient turbidity with anhydrous ether to yield 0.32 g of the hydrochloride salt melting at 123° C. (d).

Anal. Calcd. for $C_{13}H_{22}N_2O_5S_3.HCl$: C, 37.27; H, 5.53; N, 6.69; Found C, 37.19; H, 5.68; N, 6.57.

The β-isomer (1.53 g, 0.0040 m) was dissolved in absolute ethanol (10 ml), 4.8 N ethanolic hydrochloric acid (1.3 ml) was added and the solution was diluted to incipient turbidity with anhydrous ether to yield 1.52 g of the hydrochloride salt melting at 110° C. (d).

Anal. Calcd. for $C_{13}H_{22}N_2O_5S_3.HCl$: C, 37.27; H, 5.53; N, 6.69; Found C, 36.95; H, 5.63; N, 6.59;

PMR studies showed the α-isomer to have a trans configruation and the β-isomer to be cis.

The following compounds in Table I were prepared by employing essentially the same procedures as described in the examples indicated in Table I.

TABLE I

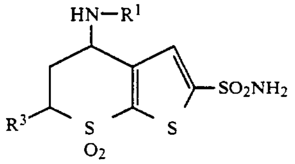

39

| Examples | $R^3$ | $R^1$ | Isomer | mp (°C.) |
|---|---|---|---|---|
| 6 | $HOCH_2CH_2NHCH_2-$ | $-CH_2CH_3$ | trans (+/−) | 190-192 |
| 6 | $HOCH_2CH_2NHCH_2-$ | $-CH_2CH_3$ | cis (+/−) | 145-155 |
| 2, 3 | $CH_3CH_2OCH_2CH_2-$ | $-CH_2CH_2CH_3$ | trans (−) | 244.5-247 |
| 2, 3 | $CH_3CH_2OCH_2CH_2-$ | $-CH_2CH_2CH_3$ | trans (+) | 244-247 |
| 10 | $CH_3CH_2OCH_2CH_2CH_2-$ | $-CH_2CH_3$ | trans (+/−) | 235-236 |
| 10 | $CH_3CH_2OCH_2CH_2CH_2-$ | $-CH_2CH_3$ | cis (+/−) | 226-227 |
| 3 | $CH_3OCH_2CH_2CH_2-$ | $-CH_2CH_3$ | cis (+) | 229-230 |
| 3 | $CH_3OCH_2CH_2CH_2-$ | $-CH_2CH_3$ | cis (−) | 229-230 |
| 10 | $CH_3OCH_2CH_2CH_2-$ | $-CH_3$ | trans (+/−) | 214-216 |
| 7 | $CH_3OCH_2CH_2CH_2-$ | $-CH_3$ | cis (+/−) | 149-151 |
| 10 | $CH_3CH_2OCH_2CH_2CH_2-$ | $-CH_2CH_3$ | trans (−) | 193-194 |
| 5 | $CH_3OCH_2CH_2OCH_2-$ | $-CH_2CH_3$ | cis (+/−) | 205-207 |
| 5 | $CH_3OCH_2CH_2OCH_2-$ | $-CH_2CH_3$ | trans (+/−) | 135-137 |
| 3 | $CH_3OCH_2CH_2OCH_2-$ | $-CH_2CH_3$ | trans (+) | 207-209 |
| 3 | $CH_3OCH_2CH_2OCH_2-$ | $-CH_2CH_3$ | trans (−) | 208-210 |
| 3 | $CH_3CH_2OCH_2CH_2CH_2-$ | $-CH_2CH_3$ | trans (+) | 194-195 |
| 13 | $HOCH_2CH_2-$ | $-CH_2CH_3$ | trans (+/−) | 241-243 |
| 5, 3 | $CH_3CH_2CH_2OCH_2-$ | $-CH_2CH_3$ | trans (−) | 217-218 |
| 5, 3 | $CH_3CH_2CH_2OCH_2-$ | $-CH_2CH_3$ | trans (+) | 217.5-218.5 |
| 5 | $CH_3OCH_2CH_2OCH_2-$ | $-CH_2CH_2CH_3$ | trans (+/−) | 240-242 |
| 5 | $CH_3OCH_2CH_2OCH_2-$ | $-CH_2CH_2CH_3$ | cis (+/−) | 215-217 |
| 3 | $CH_3OCH_2CH_2OCH_2-$ | $-CH_2CH_2CH_3$ | trans (S,S) | 201-203 |
| 6 | $CH_3OCH_2CH_2NHCH_2$ | $-CH_2CH_3$ | trans (+/−) | 218-220 (.2HCl) |
| 32 | $CH_3OCH_2CH_2NHCH_2$ | $-CH_2CH_3$ | trans (−) | 85 (.2HCl) |
| 6 | $CH_3OCH_2CH_2NHCH_2$ | $-CH_2CH_3$ | cis (+/−) | 195-198 (.2HCl) |
| 17 | $CH_3SCH_2CH_2-$ | $-CH_2CH_3$ | trans (+/−) | 242-243 |
| 22 | $CH_3SO_2CH_2CH_2-$ | $-CH_2CH_3$ | trans (+/−) | 213-216.5 |
| 21 | $CH_3SOCH_2CH_2-$ | $-CH_2CH_3$ | trans (+/−) | 231.5-234 |
| 2 | $CH_3OCH_2CH_2OCH_2CH_2-$ | $-CH_2CH_3$ | trans (+/−) | 138-140 (maleate) |
| 2, 3 | $CH_3OCH_2CH_2OCH_2CH_2$ | $-CH_2CH_2CH_3$ | trans (−) | 156-158 |
| 3 | $CH_3OCH_2CH_2OCH_2CH_2-$ | $-CH_2CH_3$ | trans (−) | 98-105 (maleate) |
| 2 | $CH_3OCH_2CH_2OCH_2CH_2-$ | $-CH_2CH_3$ | trans (+) | 70-80 (maleate) |
| 2 | $CH_3OCH_2CH_2OCH_2CH_2-$ | $-CH_2CH_3$ | cis (+/−) | 155-158 (maleate) |

TABLE I-continued

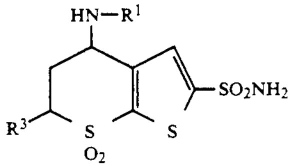

39

| Examples | $R^3$ | $R^1$ | Isomer | mp (°C.) |
|---|---|---|---|---|
| 5 | $CH_3CH_2CH_2OCH_2-$ | $-CH_2CH_2CH_3$ | trans (+/−) | ~140 |
| 3 | $CH_3CH_2CH_2OCH_2-$ | $-CH_2CH_2CH_3$ | trans (−) | 201-206 |
| 3 | $CH_3CH_2CH_2OCH_2-$ | $-CH_2CH_2CH_3$ | trans (+) | — |
| 20 | $CH_3CH_2OCH_2CH_2O-$ $CH_2CH_2CH_2-$ | $-CH_2CH_2CH_3$ | trans (−) | 184-186 |
| 10 | $CH_3OCH_2CH_2O-$ $CH_2CH_2CH_2-$ | $-CH_2CH_3$ | trans (+/−) | 184-182 |
| 10 | $CH_3OCH_2CH_2O-$ $CH_2CH_2CH_2-$ | $-CH_2CH_3$ | cis (+/−) | 200-202 |
| 20 | $CH_3OCH_2CH_2O-$ $CH_2CH_2CH_2-$ | $-CH_2CH_2CH_3$ | trans (−) | 180-182 |
| 20 | $CH_3OCH_2CH_2CH_2O-$ $CH_2CH_2CH_2-$ | $-CH_2CH_2CH_3$ | trans (−) | 160-162 |
| 30 | $CH_3O-C_6H_4-(CH_2)_2-$ | $-CH_2CH_3$ | trans (+/−) | >250 |
| 33 | $HO-C_6H_4-(CH_2)_2-$ | $-CH_2CH_3$ | trans (+/−) | 170-172 |
| 35 | 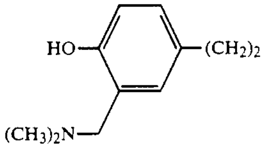 | $-CH_2CH_3$ | trans (+/−) | 189-191 |
| 19, 20 | $NC-CH_2CH_2CH_2-$ | $-CH_2CH_3$ | trans (S,S) | 213-5° |
| 17 (Step A) | $HOCH_2-$ | $-CH_2CH_3$ | trans (−) | 167-8° |
| 17 (Step A) | $HOCH_2-$ | $-CH_2CH_3$ | cis (+/−) | 195-6° |
| 20 | $CH_3CH_2CH_2S$ | $-CH_2CH_2CH_3$ | trans (S,S) | 122-6° |
| 20 | 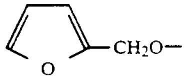 | $CH_2CH_2CH_3$ | trans (S,S) | 117-23° |
| 21 | $CH_3CH_2S(O)CH_2CH_2CH_2-$ | $CH_2CH_2CH_3$ | trans (S,S,) | >158° dec.) |
| 21 | $CH_3CH_2CH_2S(O)CH_2CH_2CH_2$ | $-CH_2CH_2CH_3$ | trans (S,S) | 131-5° |
| 41 | $CH_2=CHCH_2OCH_2-$ | H | trans/cis (1:1) | 167-8° |

Also preparable by the described procedure are the following compounds:

| $R^3$ | $R^1$ |
|---|---|
| $CH_3CH_2O(CH_2)_2-$ | $-(CH_2)_2-S-CH_2CH_3$ |
| $(CH_3)_2N(CH_2)_2-O-(CH_2)_2-$ | $-(CH_2)_2OCH_3$ |
| $C_6H_5-CH_2OCH_2-$ | $-(CH_2)_2-N(CH_3)_2$ |
| $(HO-C_6H_4)CH_2OCH_2-$ | $-(CH_2)_2-CN$ |
| $[3\text{-}(CH_3)_2NCH_2\text{-}4\text{-}OH-C_6H_3]CH_2OCH_2-$ | $-CH_2CH_3$ |
| $[3\text{-}(CH_3)_2NCH_2\text{-}4\text{-}OH-C_6H_3]CH_2O(CH_2)_2-$ | $-CH_2CH_3$ |
| $NC-(CH_2)_2O(CH_2)_2$ | $-(CH_2)_2OCH_3$ |
| $CH_3SCH_2$ | $-(CH_2)_2N(CH_3)_2$ |
| $F(CH_2)_2NHCH_2$ | $-(CH_2)_2OCH_3$ |
| $HO-C_6H_4CH_2NHCH_2$ | $-(CH_2)_3OCH_3$ |
| $NCCH_2-$ | $-(CH_2)_3OH$ |
| $HOC_6H_4-$ | $-(CH_2)_2OH$ |
| furyl- | $-(CH_2)_3OCH_3$ |
| $[3\text{-}(CH_3)_2NCH_2\text{-}4\text{-}OH-C_6H_3]CH_2-$ | $-(CH_2)_3OH$ |
| $CH_3O(CH_2)_4OCH_2-$ | $-(CH_2)_3F$ |
| $CH_3CH_2OCH_2-$ | $-(CH_2)_4OCH_3$ |
| $HO(CH_2)_2O(CH_2)_5$ | $-CH_2CH_2CH_3$ |
| $HOCH_2CH_2OCH_2-$ | $-CH_2CH_2CH_3$ |
| $CH_3CH_2CH_2NHCH_2-$ | $-CH_2CH_3$ |
| $CH_3OCH_2CH_2NHCH_2$ | $-CH_2CH_2CH_3$ |
| $CH_3S-CH_2-$(1) | $-CH_2CH_3$ |
| $HOCH_2CH_2S-CH_2-$ | $-CH_2CH_3$ |
| $CH_3OCH_2CH_2S-CH_2-$ | $-CH_2CH_2CH_3$ |
| $[4\text{-}HO\text{-}3\text{-}(CH_3)_2NCH_2-C_6H_3]-CH_2OCH_2-$ | $-CH_2CH_2CH_3$ |
| $[5\text{-}(CH_3)_2NCH_2\text{-}furyl\text{-}2]\text{-}CH_2-O-CH_2CH_2-$ | $-CH_2CH_2CH_3$ |

-continued

| $R^3$ | $R^1$ |
|---|---|
| $CH_3CH_2CH_2OCH_2CH_2$— | —$CH_2CH_3$ |
| $HOCH_2CH_2OCH_2CH_2$— | —$CH_2CH_2CH_3$ |
| [4-HO-3-($CH_3$)$_2$$NCH_2$—$C_6H_3$]—$CH_2OCH_2CH_2$— | —$CH_2CH_2CH_3$ |

(1) Oxidation of this compound with sodium metaperiodate and Oxone ® provides the corresponding sulfoxide and sulfone, respectively.

EXAMPLE 8

Enantiomers of cis-5,6-dihydro-6-ethoxymethyl-4-(N-propylamino)-4H-thieno[2,3-b]thiopyran-2-sulfonamide-7,7-dioxide.

Step A: Preparation of the cis(+) enantiomer

To a solution of 5,6-dihydro-6-ethoxymethyl-4-(n-propylamino)-4H-thieno[2,3-b)thiopyran-2-sulfonamide-7,7-dioxide (cis,β-isomer),(3.5 g, 0.0092 m), in acetonitrile (60 ml) was added di-p-toluoyl-D-tartaric acid monohydrate (0.93, 0.0023 m). After standing overnight at ambient temperature, the white solid product was collected, dried and recrystallized twice more from acetonitrile-methanol to yield 2.1 g of resolved salt. The product was converted to the free base by treatment with saturated bicarbonate solution and extraction four times with ethyl acetate. The combined ethyl acetate extracts were washed with saturated sodium chloride, dried over sodium sulfate and concentrated in vacuo to yield 1.8 g of the base. Conversion to the hydrochloride salt utilizing ethanolic hydrogen chloride yielded a crystalline analytical sample melting at 160°-161° C(d).

Anal. Calc'd for $C_{13}H_{22}N_2O_5S_3$, HCl; C, 37.27; H, 5.53; N, 6.69 Found C, 37.48; H, 5.60; N, 6.71

$[\alpha]_D^{25}$ = +59.241, for the hydrochloride salt in methanol

Step B: Preparation of the cis(−) enantiomer

The combined mother liquors from the separation of the dextrorotatory enantiomer were concentrated in . The residue was treated with saturated sodium bicarbonate solution and extracted five times with ethyl acetate. The combined extracts were washed with water, dried over sodium sulfate and evaporated in vacuo to yield 1.9g. of the free base. A solution of the base in acetonitrile (60 ml) was treated with di-p-toluoyl-L-tartaric acid (0.93g, 0.0024 m). After standing overnight at ambient temperature, the white solid product was collected, dried and recrystallized twice more from acetonitrile-methanol to yield 2.0 g of resolved salt. The salt was converted to the free base by treatment with saturated sodium bicarbonate solution and extraction four times with ethyl acetate. After washing with water and drying over sodium sulfate, the solvent was evaporated in vacuo to yield 1.2 g. of base. Conversion to the crystalline hydrochloride salt using ethanolic hydrogen chloride gave an analytical sample melting at 157°-90° C. (d). Anal. Calc'd for $Cl_3H_{22}N_2O_5S_3$. HCL: C, 37.27; H, 5.53; N, 6.69 Found C, 37.41; H, 5.86; N, 6.34

$[\alpha]_D^{25}$ = −65.23°, for the hydrochloride salt in methanol

EXAMPLE 9

5,6-Dihydro-4-ethylamino-6-(2-methoxyethyl)-4H-thieno[2,3-b]thiopyran-2-sulfonamide-7,7-dioxide Step A: Preparation of 5,6-Dihydro-4-(methoxyethoxymethoxy)-6-(2-methoxyethyl)-4H-thieno[2,3-b]thiopyran

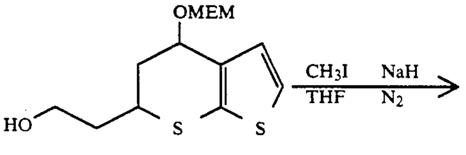

40

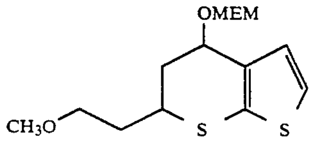

41

Sodium hydride (2.4g, 0.05 mol of 50% dispersion in mineral oil) was washed free of mineral oil using pet. ether under nitrogen and was suspended in dry tetrahydrofuran (25 ml). The suspension was cooled to 0° C. and stirred as 11.2 g (0.037 mol) of 5,6-dihydro-6-(2-hydroxyethyl)-4-(methoxyethoxymethoxy)-4H-thieno[2,3-b]thiopyran dissolved in dry tetrahydrofuran (25 ml) was added rapidly. Finally, 14.2 g (0.10 mol) of methyl iodide was added and the mixture was stirred at ambient temperature overnight. The resulting white suspension was concentrated in vacuo at room temperature to remove the tetrahydrofuran. The pale yellow residue was taken up in ethyl acetate (150 ml) and water (50 ml). The ethyl acetate solution was separated, washed with saturated NaCl, dried, filtered and concentrated in vacuo to give the product as a pale yellow oil (11.2g, 95% yield).

Step B: Preparation of 5,6-Dihydro-4-(methoxyethoxymethoxy-6-(2-methoxyethyl)-4H-thieno[2,3-b]-thiopyran-2-sulfonamide 41 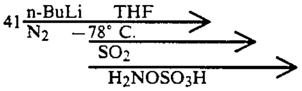

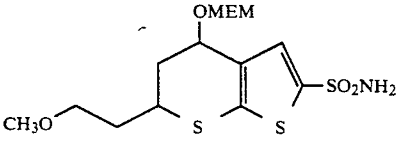

42

5,6-Dihydro-4-(methoxyethoxymethoxy)-6-(2-methoxyethyl)-4H-thieno[2,3-b]thiopyran (11.2 g, 0.035 mol) was dissolved in dry tetrahydrofuran (100 ml) and the solution was cooled to −78° C. under nitrogen. Then n-butyl lithium (16.8 mol, 0.042 mol of 2.5 m in hexane) was added dropwise over ½ hour. The solution was stirred at −78° C. for an additional hour. Anhydrous sulfur dioxide was bubbled over the surface of the solution at −78° C. to −40° C. until the mixture became acidic. Stirring at −40° to −78° C. was continued for 2¼ hours and then to room temperature over ½ hour. The solution was concentrated in vacuo. The residual lithio salt was dissolved in water (75 ml) containing sodium acetate (8.2g, 0.10 mol) and the solution was cooled to 0° C. Hydroxylamine-O-sulfonic acid (9.5 g, 0.084 mol) was added and the mixture was stirred at room temperature overnight. The reaction mixture was diluted with saturated sodium bicarbonate (100 ml) and ethyl acetate (200 ml). The aqueous layer was separated and extracted with ethyl acetate. The ethyl acetate solutions were combined, washed with water, dried, filtered and concentrated in to an amber liquid (13.1 g 94%).

Step C: 5,6-Dihydro-4-(methoxyethoxymethoxy)-6-(2-methoxyethyl)-4H-thieno[2,3-b]thiopyran-2-sulfonamide-7,7-dioxide 42
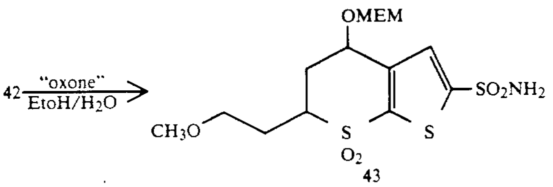

43

5,6-Dihydro-4-(methoxyethoxymethoxy)-6-(2-methoxyethyl)-4H-thieno[2,3-b]thiopyran-2-sulfonamide (13.1 g. 0.033 mol) was dissolved in ethanol (150 ml) and water (75 ml) was added. To this stirred cloudy solution was added Oxone® (30.7 g, 0.05 mol). After stirring at ambient temperature for 3 hours another 7.7 g of Oxone® was added. Stirring was continued for an additional 1½ hours and then the mixture was basified by adding excess sodium bicarbonate in small portions. The mixture was filtered and the solids were washed with ethyl acetate and ethanol. The filtrate and washings were concentrated in vacuo at room temperature. The residual yellow gum was taken up in ethyl acetate (250 ml) and water (50 ml). The ethyl acetate solution was separated and washed with saturated NaCl, dried, filtered and concentrated in vacuo at room temperature to give 12.3 g (86%) of pale yellow oil.

Step D: Preparation of 5,6-Dihydro-4-hydroxy-6-(2-methoxyethyl)-4H-thieno[2,3-b]thiopyran-2-sulfonamide-7,7-dioxide 43 + $H_2SO_4$
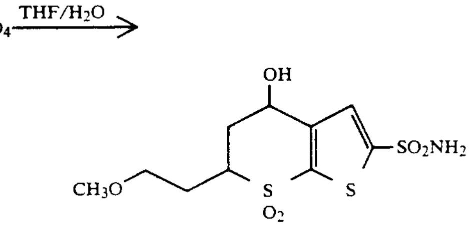

44

5,6-Dihydro-4-(methoxyethoxymethoxy)-6-(2-methoxyethyl)-4H-thieno[2,3-b]thiopyran-2-sulfonamide-7,7-dioxide (12.0 g, 0.028 mol) was dissolved in 25 ml of tetrahydrofuran and 50 ml of sulfuric acid-water (50-50, volume-volume) was added. The solution was stirred at ambient temperature for 4 hours. Then the solution was poured into a suspension of sodium bicarbonate (200 g) in ethyl acetate (300 ml). After the mixture was neutralized it was filtered. The solids were washed with ethyl acetate and tetrahydrofuran and the filtrate and washings were concentrated in vacuo at room temperature. The residual oil was taken up in ethyl acetate (150 ml), washed with saturated NaCl, dried, filtered and concentrated in vacuo at room temperature to give 9.16 g (95%) of white solid foam.

Step E: Preparation of 4-acetamido-5,6-dihydro- 6-(2-methoxyethyl)-4H-thieno[2,3-b]-thiopyran-2-sulfonamide-7,7-dioxide 44 + $CH_3CN$ + $H_2SO_4$
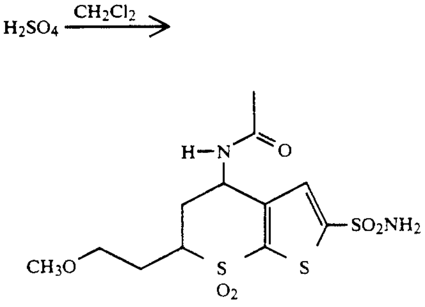

45

5,6-Dihydro-4-hydroxy-6-(2-methoxyethyl)-4H-thieno[2,3-b]thiopyran-2-sulfonamide-7,7-dioxide (8.86 g, 0.026 mol) was dissolved in dry acetonitrile (85 ml) and methylene chloride (40 ml). Concentrated sulfuric acid (24 ml, 0.45 mol) was added dropwise over 1 hour at −5° to −10° C. The solution was left stirring overnight as the ice melted in the cooling bath and the temperature rose to room temperature. After 24 hours the reaction solution was poured into 300 ml of ice and water. Solid sodium bicarbonate was then added until the mixture was slightly basic. Then 300 ml of water was added to dissolve the salts and the mixture was extracted with 150 and 3×100 ml of ethyl acetate. The combined extracts were washed with saturated NaCl solution, dried, filtered and concentrated in vacuo at room temperature to give 4.4 g (44%) of pale yellow solid.

Step F: 5,6-Dihydro-4-ethylamino-6-(2-methoxyethyl)-4H-thieno[2,3-b]thiopyran-2-sulfonamide-7,7-dioxide (cis and trans isomers)

46
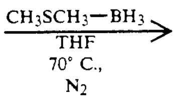

-continued

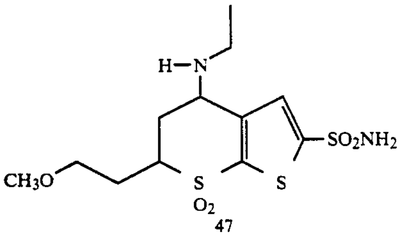

47

To a stirred solution of 4-acetamido-5,6-dihydro-6-(2-methoxyethyl)-4H-thieno[2,3-b]thiopyran-2-sulfonamide-7,7-dioxide (4.4 g, 0.0115 mol) in tetrahydrofuran (45 ml) under nitrogen and heated to reflux was added borane dimethylsulfide complex (5 ml, 0.05 mol of a 10 M complex) over about 20 minutes. Stirring was continued at reflux for 3 hours, then at room temperature overnight and another 5 hours and then concentrated in vacuo at room temperature. Methanol (50 ml) was carefully added to the white residue. The resulting solution was saturated with anhydrous HCl gas and then was stirred at reflux for 1 hour. The solution was concentrated in vacuo and the residue was taken up in ethyl acetate (50 ml) and saturated sodium bicarbonate (20 ml). The ethyl acetate solution was separated and washed with saturated NaCl, dried, filtered and concentrated in vacuo. The procedure gave a mixture of cis and trans isomers (3.2 g) as a white gummy foam which was chromatographed on silica gel (300 g) using 7.5% methanol-chloroform. Mixed fractions (0.87 g) were chromatographed again using 5% methanol-ether. There was obtained 1.62 g of the a-isomer, mp 132°-134° C. and 0.35 g of the β-isomer, mp 167°-169° C. The hydrochloride salts of the α (trans) and β-isomer (cis) racemates were prepared using ethanolic-HCl and diluting with ether. MP's were 173°-175° C. and 264.5°-266° C., respectively.

EXAMPLE 10

5,6-Dihydro-4-ethylamino-6-(3-methoxypropyl)-4H-thieno[2.3-b]thiopyran-2-sulfonamide-7.7-dioxide Step A: Preparation of 5-carbomethoxy-3-thienyl-thiopentanoic acid

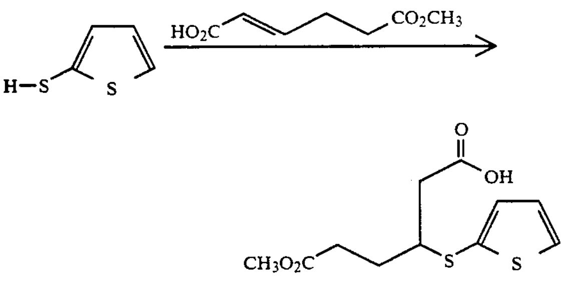

48

A solution of 2-mercaptothiophene (29 g, 0.25 mol), 5-carbomethoxypent-2-enoic acid (40 g, 0.25 mol) and triethylamine (18.6 ml, 0.134 mol) in dry THF (430 ml) was heated at reflux for 3 hours. The THF was evaporated at reduced pressure, the residue dissolved in ethyl acetate, washed with cold 2N HCl, $H_2O$, brine, dried over $Na_2SO_4$ and evaporated at reduced pressure to give 63 g of the title compound which was used in Step B without further purification.

Step B: Preparation of 6-(2-carbomethoxyethyl)-5,6-dihydro-4- oxo-4H-thieno[2,3-b]thiopyran

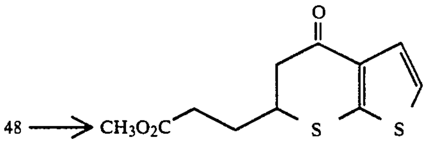

49

A solution of compound from Step A (63 g, 0.252 mol) in $CH_2Cl_2$ (600 ml) and dimethylformamide (1 ml) in a $N_2$ atmosphere was treated over a 20 minute period with oxalyl chloride (22.4 ml, 0.26 mol) in $CH_2Cl_2$ (50 ml). The reaction mixture was stirred at 25° C. for 2 hours, cooled to −10° C. and treated with $SnCl_4$ (14.5 ml, 0.125 mol) in $CH_2Cl_2$ (50 ml) over a 20 minute period. The reaction was stirred at 0° C. for 1 hour then poured into 300 ml of vigorously stirred ice and $H_2O$. The $CH_2Cl_2$ layer was washed with saturated $NaHCO_3$, brine then dried over $Na_2SO_4$ and evaporated at reduced pressure. Purification was effected by flash chromatography on $SiO_2$ eluting with ethyl acetate-hexane (1:3 v/v).

Step C: Preparation of 6-(2-carboethoxyethyl)-5,6-dihydro-4-hydroxy-4H-thieno[2,3-b]thiopyran

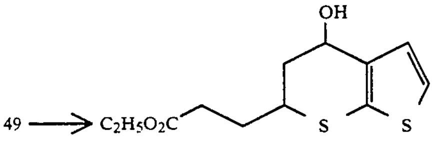

50

A solution of compound from Step B (40.0 g, 0.156 mol) in ethanol (460 ml) was cooled to 0° C. in a $N_2$ atmosphere, and treated with sodium borohydride (1.90 g, 0.05 mole). The reaction mixture was stirred at 25° C. for 18 hours then the ethanol was evaporated at reduced pressure. The residue was dissolved in ethyl acetate, washed with ice-$H_2O$, saturated NaHCO3, brine, then dried over $Na_2SO_4$. Evaporation of the ethyl acetate left 42 g of title compound as an oil.

Step D: Preparation of 6-(2-carboethoxyethyl)-5,6-dihydro-4-methoxyethoxymethoxy-4H-thieno-[2,3-b]thiopyran

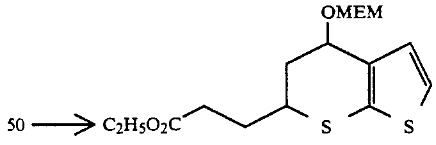

51

A stirred solution of product from Step C (46.8 g, 0.172 mol) in $CH_2Cl_2$ (350 ml) was cooled in an ice bath and treated with N,N-diisopropylethylamie (47.4 ml, 0.273 mol) and methoxyethoxymethyl chloride (31.2 ml, 0.273 mol). The reaction mixture was stirred at 25° C. for 18 hours washed with ice-$H_2O$, saturated $NaHCO_3$ and brine then dried over $Na_2SO_4$. Evaporation of the $CH_2Cl_2$ left 58.6 of title compound as a yellow oil.

Step E: Preparation of 5,6-Dihydro-6-(3-hydroxy-propyl)-4-methoxyethoxymethoxy-4H-thieno-[2,3-b]thiopyran

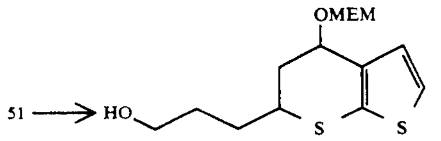

52

Diethyl ether (55 ml) was cooled in an ice bath in a $N_2$ atmosphere. Lithium aluminum hydride (3.93 g, 0.104 mol) was suspended with stirring and a solution of product from Step D (29.3 g, 0.0814 mol) in THF (78 ml) was added over a 1.5 hour period at 0°-3° C. The reaction mixture was stirred at 25° C. for 18 hours, cooled in ice then cautiously treated dropwise with $H_2O$ (4.15 ml) over ½ hour, then with 20% NaOH (3.1 ml) and finally with more $H_2O$ (14.5 ml). Stirring was continued for ½ hour, the precipitated salts filtered and rinsed with ether. The combined organic phase was dried over $Na_2SO_4$ and evaporated at reduced pressure to leave 25 g of product as a yellow oil.

Step F: Preparation of 5,6-Dihydro-4-methoxyethoxy-methoxy-6-(3-methoxypropyl)-4H-thieno-[2,3-b]thiopyran

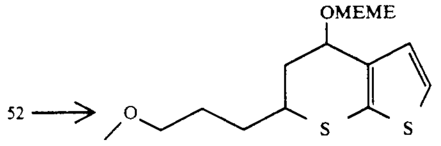

53

Sodium hydride (50% in mineral oil, 4.8 g, 0.10 mole) was rinsed with petroleum ether then transferred under $N_2$ to a 500 ml flask with THF. The suspension was cooled in ice with stirring and compound from Step E (25 g, 0.079 mol) in THF (80 ml) was added over 20 minutes. The reaction mixture was stirred for ½ hour then methyl iodide (30.2 g, 0.21 mol) was added and stirring was continued for 18 hours at 25° C. Most of the THF was evaporated. The residue was dissolved in ethyl acetate, washed with $H_2O$, brine, dried over $Na_2SO_4$ and the solvent evaporated at reduced pressure to leave 25 g of product as a yellow oil.

Step G: Preparation of 5,6-Dihydro-4-methoxyethoxy-methoxy-6-(3-methoxypropyl)-4H-thieno[2,3-b]-thiopyran-2-sulfonamide

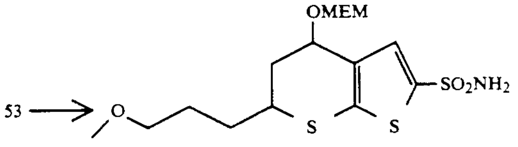

54

Under $N_2$ a solution of compound from Step F (25 g, 0.075 mol) in THF (220 ml) was cooled to −78° C. with stirring. A solution of butyl lithium (2.5 M in hexane, 39 ml, 0.098 mol) was added over 15 minutes then stirring was continued at −78° C. for 1 hour. The nitrogen inlet was replaced by an inlet for $SO_2$ gas which was introduced over the surface of the reaction for 15 minutes during which time the temperature rose to −55° C. then dropped back to −78° C. Stirring was continued at −78° C. for 2 hours then at 20° C. for ½ hour. The solvents were evaporated in and the residue was stirred in ice while a solution of sodium acetate (19.2 g, 0.234 mole) in water (175 ml) was added followed by hydroxylamine-O-sulfonic acid (22.2 g, 0.197 mol). The reaction was stirred at 25° C. for one hour then treated with saturated $NaHCO_3$ until slightly basic, extracted with ethyl acetate, washed with brine, dried over $Na_2SO_4$ and evaporated at reduced pressure to give 28 g of product which melted at 114° C. after crystallization from ethyl acetatehexane.

Anal. Cal'd for $C_{16}H_{25}NO_6S_3$: C, 43.78; H, 6.12; N, 3.40 Found: C, 43.35; H, 5.88; N, 3.45

Step H: Preparation of 4-Acetamido-5,6-dihydro-6-(3-methoxypropyl)-4H-thieno[2,3-b]thiopyran-2-sulfonamide

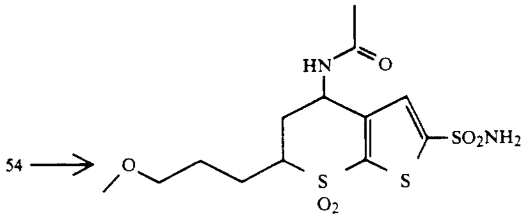

55

A stirred suspension of product from Step G (14.0 g, 0.034 mol) in acetonitrile (125 ml) was cooled to 15° C. and treated over 15 minutes with concentrated sulfuric acid (18.1 ml). The reaction mixture was stirred at 25° C. for 4 hours then poured into ice $H_2O$ (500 ml) and made basic by the addition of solid $NaHCO_3$. Ethyl acetate (700 ml) was added, the precipitated salt removed by filtration and the ethyl acetate solution was washed with brine, dried over $Na_2SO_4$ and evaporated at reduced pressure to give 13 g of product as a reddish-brown gum.

Step I: Preparation of 4-Acetamido-5,6-dihydro-6-(3-methoxypropyl)-4H-thieno[2,3-b]thiopyran-2-sulfonamide-7,7-dioxide

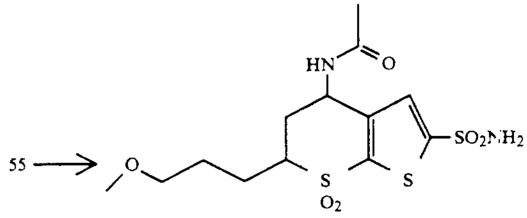

56

Water (66 ml) was added to a solution of product from Step H (13 g, 0.035 mole) in warm ethanol (130 ml). Oxone® (32.8 g, 0.053 mol) was added and the mixture stirred at 25° C. for 18 hours. Solid $NaHCO_3$ was added to neutrality, the salts filtered, rinsed with ethanol and the solvents evaporated at reduced pressure. The residue was dissolved in ethyl acetate (150 ml) washed with saturated $NaHCO_3$ and brine, dried over $Na_2SO_4$ and evaporated at reduced pressure. Chromatography on $SiO_2$ eluted with $CHCl_3$-$CH_3OH$ (10:1) gave 8.7 g of product.

Step J: Preparation of 5,6-Dihydro-4-ethylamino-6-(3-methoxypropyl)-4H-thieno[2,3-b]thiopyran-2-sulfonamide-7,7-dioxide 56
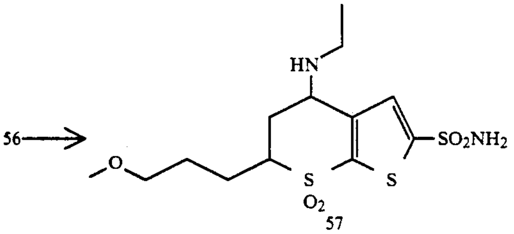
57

A stirred solution of product from Step I (8.7 g, 0.022 mole) in dry THF (45 ml) was heated to reflux in a $N_2$ atmosphere. Borane-methylsulfide complex (22 ml, 0.22 mol) was added over 15 minutes, the reaction refluxed 4 hours then cooled in an ice bath. Methanol (22 ml) was added dropwise over ½ hour then the solvents were evaporated at reduced pressure. The flask was again cooled in ice and 6N HCl (82 ml) was slowly added. The acidic solution was heated on a steam bath for ½ hour, evaporated to dryness, dissolved in ethyl acetate (700 ml) washed with brine, dried over $Na_2SO_4$ and evaporated at reduced pressure to give 8 g of a mixture of cis and trans products which were separated by chromatography eluting with $CHCl_3$—$CH_3OH$ (10:1). Each isomer was converted to its hydrochloride salt with ethanolic HCl.

mp (trans.HCl): 212°-214° C.

mp (cis.HCl): 251°-252° C.

Anal. Calc'd for $C_{13}H_{22}N_2O_5S_3.HCO$: C, 37.27; H, 5.53; N, 6.69 Found: (trans) C, 37.49; E, 5.63; N, 6.74 Found: (cis) C, 37.58; H, 5.45; N, 6.68.

Step K: Resolution of the trans diastereomer

To a warm stirred solution of the trans product from Step J (3.67 g, 9.6 Mm) in acetonitrile (40 ml) was added di-p-toluoyl-D-tartaric acid hydrate (960 mg, 2.4 Mm). The mixture was cooled, the salt filtered, slurried in fresh warm acetonitrile (40 ml) cooled and filtered. The salt thus obtained was treated with saturated $NaHCO_3$ and ethyl acetate. The ethyl acetate was washed with water and brine, dried over $Na_2SO_4$ and evaporated at reduced pressure. The residual base was dissolved in hot ethanol (50 ml) and treated with an excess of ethanolic HCl. The solution was cooled and filtered to give 1.3 g of trans (+) product hydrochloride which melted at 233°-235° C. as the hemi-hydrate.

Anal. Cal'd for $C_{13}H_{22}N_2O_5S_3.HCl.\frac{1}{2}H_2O$ C, 36.48; H, 5.65; N, 6.35 Found: C, 36.67; H, 5.56; 11, 6.56.

$[\alpha]_D^{25} = +12.1°$ ($CH_3OH$)

The cetonitrile filtrates from the resolution of the trans (-r) isomer were evaporated to dryness and distributed between ethyl acetate and saturated $NaHCO_3$. The ethyl acetate layer was washed with brine, dried over $Na_2SO_4$ and evaporated in to give 2.3 g (6 Mm) of free base. The base was dissolved in 50 ml of hot acetonitrile and treated with di-p-toluoyl-L-tartaric acid hydrate (1.21 g, 3 mMol) then refrigerated overnight. The salt was filtered, slurried in warn acetonitrile (30 ml) cooled, filtered and dried. The resulting salt was distributed between ethyl acetate and saturated $NaHCO_3$; the ethyl acetate was washed with brine, dried over $Na_2SO_4$ and evaporated in vacuo. The resultant base was dissolved in ethanol (50 ml) and treated with an excess of ethanolic hydrochloric acid and filtered to give 1.6 g of trans (−) enantiomer hydrochloride hemiethanolate.

Anal. Calc'd for $C_{13}H_{22}N_2O_5S_3.HCl.\frac{1}{2}EtOH$ C, 38.04; H, 5.93; N, 6.34 Found: C, 38.26; H, 6.11; N, 6.15.

$[\alpha]_D^{25} = -12.21$, ($CH_3OH$).

A 190 mg sample of trans (−) base was dissolved in ethanol (5 ml) to which was added a slight excess of isethionic acid. Treatment with ether gave the trans (−) enantiomer isethionate.

Anal. Calc'd for $C_{13}H_{22}N_2O_5S_3.C_2H_6O_4S$ C, 35.42; H, 5.55; N, 5.51 Found: C, 35.51; H, 5.47; N, 5.28.

EXAMPLE 11

5,6-Dihydro-6-(3-methoxypropyl)-4-propylamino-4H-thieno[2,3-b]sulfonamide-7,7-dioxide Step A: Preparation of 5,6-Dihydro-6-(3-methoxypropyl)-4-propronamido-4H-thieno[2,3-b]thiopyran-2-sulfonamide

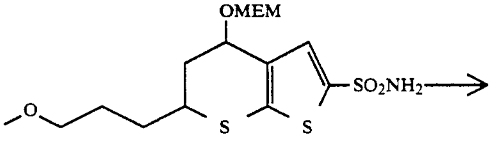
58

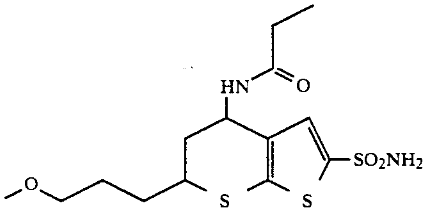
59

A stirred suspension of 5,6-Dihydro-4-methoxyethoxymethoxy)-6-(3-methoxypropyl)-4H-thieno[2,3-b]thiopyran-2-sulfonamide (12.6 g, 0.307 mol) in propionitrile (125 ml) was cooled to 15° C. and treated with concentrated $H_2SO_4$ (16.3 ml) over a 5 minute period. The reaction mixture was stirred at 25° C. for 3 hours, poured into ice $H_2O$, made basic with solid $NaHCO_3$ and extracted with ethyl acetate which was washed with brine, dried over $Na_2SO_4$ and evaporated in vacuo to give 12.4 g of product.

Step B: 5,6-Dihydro-6-(3-methoxypropyl)-4-propon-amido-4H-thieno[2,3-b]thiopyran-2-sulfonamide-7,7-dioxide 59
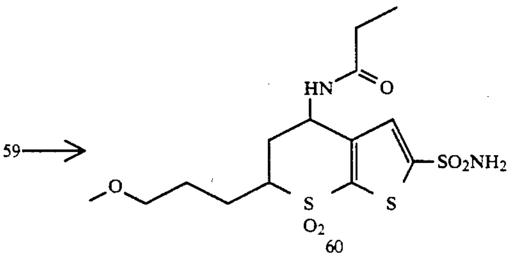
60

Water (60 ml) was added to a stirred solution of product from Step A in hot ethanol (120 ml) then Oxone ® (30 g, 0.049 mol) was added over 5 minutes. The reaction mixture was stirred at 25° C. for 3 hours and neutralized with solid $NaHCO_3$. The salts were filtered, rinsed with ethanol and ethyl acetate and the organic solvents were evaporated at reduced pressure. The residue was dissolved in ethyl acetate, washed with saturated $NaHCO_3$, brine and dried over $Na_2SO_4$. The ethyl acetate was evaporated in vacuo and the residue chromatographed on $SiO_2$ eluted with $CHCl_3$—$CH_3OH$ (10:1) to give 9 g of product.

Step C: Preparation of 5,6-Dihydro-6-(3-methoxypropyl)-4-propylamino-4H-thieno[2,3-b]-thiopyran-2-sulfonamide-7,7-dioxide

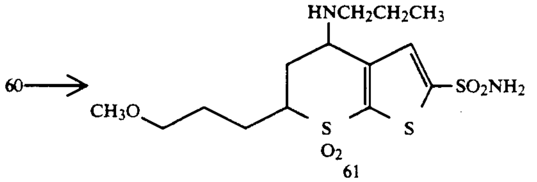

61

Under $N_2$ compound from Step B (9.0 9, 0.022 mole) was dissolved in THF (45 ml), heated to reflux and treated with borane-methyl sulfide complex (22 ml, 0.22 mol) over 15 minutes. The reaction mixture was heated at reflux for 4 hours, cooled in an ice bath and slowly treated with $CH_3OH$ (27 ml) over 50 minutes. After 1 hour the solvents were evaporated in vacuo, the residue cooled in ice and slowly treated with 6N HCl (82 ml). The HCl solution was heated on a steam bath for ½ hour then evaporated to dryness at reduced pressure. The residue was made basic with saturated $NaHCO_3$, extracted into ethyl acetate, washed with brine, dried over $Na_2SO_4$ and evaporated in vacuo. The cis and trans isomers were separated by chromatography on $SiO_2$ eluting with $CHCl_3$—$CH_3OH$ (10:1) then converted to their hydrochloride salts by treatment with ethanolic HCl and ether.

m.p. (trans)=231°-232° C. m.p. (cis)=274°-275° C.

Anal. Calc'd for $C_{14}H_{24}N_2O_5S_3$.HCl C, 38.83; H, 5.82; N , 6.47 Found: (trans) C, 38.73; H, 5.67; N, 6.38 (cis) C, 38.92; H, 5.79; N, 6.38.

Step D: Resolution of trans 5,6-Dihydro-6-(3-methoxypropyl)-4-propylamino-4H-thieno[2,3-b]-thiopyran-2-sulfonamide-7,7-dioxide To a warm solution of trans product from Step C (1.4 g, 3.54 mMol) in 2-propanol (20 ml) was added di-p-toluoyl-D-tartaric acid hydrate (0.71 g, 1.76 mmol). The solution was refrigerated and the salt thus obtained was thrice recrystallized from 2-propanol (3×30 ml). The resulting salt was treated with saturated $NaHCO_3$, extracted with ethyl acetate, washed with brine, dried over $Na_2SO_4$ and evaporated in The resulting base was treated with ethanolic HCl and ether to give 520 mg of trans (+) product hydrochloride, m.p.=215°-217° C.

Analysis Calc'd for $C_{14}H_{24}N_2O_5S$.HCl C, 38.83; H, 5.82; N, 6.47 Found: C, 38.99; H, 5.71; N, 6.44 $[\alpha]_D^{25}=+12.2°$ ($CH_3OH$).

The 2-propanol filtrates were combined and evaporated to dryness. The residue was distributed between saturated $NaRCO_3$ and ethyl acetate. The latter was washed with brine, dried over $Na_2SO_4$ and evaporated in vacuo. The base (3.8 g, 7.1 mmol) was dissolved in hot 2-propanol and treated with di-p-toluoyl-2-tartaric acid (1.43 g, 3.55 mMol) and cooled. The resulting salt was thrice recrystallized for 2-propanol (3×40 ml) converted to the base and then to the hydrochloride as previously described to give 320 mg of trans (−) enantiomer hydrochloride. mp=218°-220° C.

Analysis for $C_{14}H_{24}N_2O_5S_3$.HCl C, 38.83; H, 5.82; N, 6.47 Found: (trans (−)) C, 38.56; H, 5.71; N, 6.41 $[\alpha]_D^{25}=-12.3°$ ($CH_3OH$).

EXAMPLE 12

Enantiomers of trans-5,6-dihydro-4 ethylamino-6-[3-(2-methoxyethoxy)propyl]-4H-thieno[2,3-b]-thiopyran-2-sulfonamide-7,7-dioxide Step A: Preparation of the trans, (+) rotary enantiomer hydrochloride

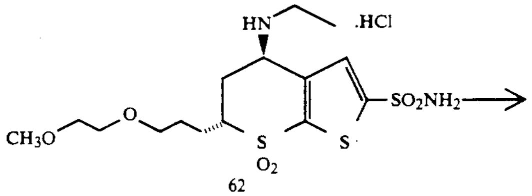

62
(trans-isomer)

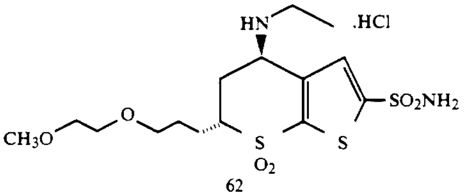

62
(trans-isomer)
(+) rotary enantiomer

A sample of the title compound (2.8 g, 6.6 mM) was dissolved in hot ethyl acetate (120 ml) along with di-p-toluoyl-D-tartaric acid (1.27 g, 3.3 mM). After standing for 7 days the white crystalline salt was filtered and recrystallized from ethyl acetate (100 ml) to give 960 mg of salt which was partitioned between aqueous $NaHCO_3$ and ethyl acetate, the latter washed with brine, dried over $Na_2SO_4$ and evaporated in vacuo. The residue was dissolved in ethanol (8 ml) treated with a slight excess of 6N ethanolic HCl then ether until cloudy then refrigerated overnight. The white crystals were filtered, rinsed with ether and dried to give 530 mg of (+) title compound which melts at 177°-9° C.

Analysis Calc'd for $C_{15}H_{26}N_2O_6S_3$.HCl C, 38.91, H, 5.88, N, 6.05 Found: C, 38.90, H, 5.96, N, 6.39

Step B: Preparation of the trans, (−) rotary enantiomer hydrochloride 62 (trans-isomer)
62 (trans-isomer) (−) rotary enantiomer The ethyl acetate filtrates from the salt were combined and washed with aqueous $NaHCO_3$ and brine, dried over $Na_2SO_4$ and evaporated in v providing 2.0 g of the (−) enriched free base which was dissolved in hot ethyl acetate along with di-p-toluoyl-L-tartaric acid (953 mg). After cooling the crystals were filtered then recrystallized from EtOAc (70 ml). The salt was partitioned between aqueous sodium bicarbonate and EtOAc, the latter washed with brine dried over sodium sulfate and evaporated in vacuo. The residue was dissolved in ethanol (5 ml), treated with a slight excess of 6N ethanolic HCl then with ether until cloudy then refrigerated. The white crystals were filtered, rinsed with ether and dried to give 380 mg of (−) title compound which melts at 177°-9° C.

Analysis Calc'd for $C_{15}H_{26}N_2O_6S_3$.HCl C, 38.91, H, 5.88, N, 6.05 Found: C, 38.83, H, 5.94, N, 5.93.

EXAMPLE 13

5,6-Dihydro-4-ethylamino-6-(2-hydroxyethoxy)methyl-4H-thieno[2,3-b]thiopyran-2-sulfonamide-7,7-dioxide hydrochloride, trans isomer

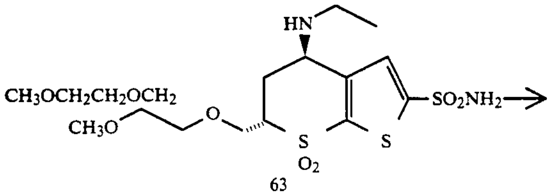

63
(trans-isomer)

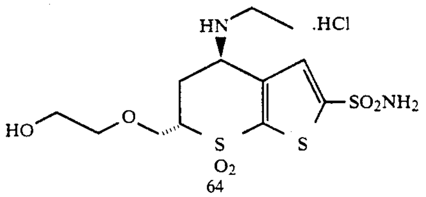

64
(trans-isomer)

Under $N_2$, 18-crown 6 (7.92 g, 0.03 mol) in $CH_2Cl_2$ (50 ml) and NaI (5 g, 0.033 mol) was stirred at room temperature. After 5 minutes, the reaction was cooled to 0°-4° C. and an ether solution of trans-5,6-dihydro-4-ethylamino-6-(2-methoxyethoxy) methyl-4H-thieno[2,3-b]thiopyran-2-sulfonamide-7,7-dioxide (2.1g, 0.005 mol) was added. After addition, the reaction was stirred at room temperature for 0.5 hours and then cooled to −78° C. and $BBr_3$ in $CH_2Cl_2$ (1M, 25 ml, 0.025 mol) was added. After the addition, the reaction was allowed to warm to 0° C. over 3 hours. The mixture was then concentrated to dryness and the residue was treated with 6N HCl (40 ml). After heating for 5 minutes in a steam bath, the reaction was cooled and neutralized to pH 8.5 with $NaHCO_3$. The resulting mixture was extracted with EtOAc(3×) and the organic extracts were dried, filtered and concentrated to dryness. The residue was chromatographed on a Still silica gel column and the product eluted with 25-50% methanol-chloroform with 2.5 to 5.0% aqueous $NH_3$ to yield crude product. The material was crystallized as the HCl salt from EtOH to yield 280 mg (13%) of the title compound; m.p. 157°-9° C.

Analysis Calc'd for $C_{12}H_{20}N_2O_6S_3$.HCl C, 34.24, H, 5.03, N, 6.66 Found: C, 34.57, H, 5.25, N, 6.49

EXAMPLE 14

(−)5,6-Dihydro-6-(3-hydroxypropyl)-4-propylamino-4H-thieno[2,3-b]thiopyran-2-sulfonamide-7,7-dioxide hydrochloride, trans isomer

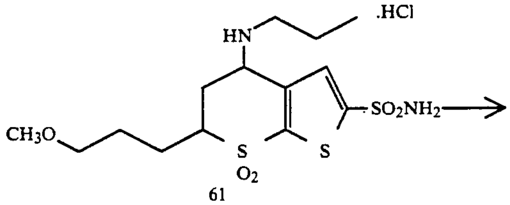

61
(trans-isomer)
(−) rotary enantiomer

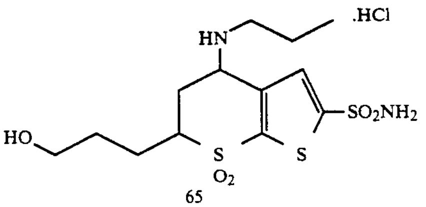

65
(trans-isomer)
(−) rotary enantiomer (−) 5,6-Dihydro-6-(3-methoxypropyl)-4-propylamino-4H-thieno[2,3-b]thiopyran-2-sulfonamide-7,7-dioxide hydrochloride, trans isomer (2.6 g 6.0 mM)(prepared as described in Example 11) was converted to the free base by partitioning between ethyl acetate and aqueous sodium bicarbonate. The ethyl acetate was washed with brine, dried over sodium sulfate and evaporated in vacuo. Under nitrogen, 18 crown 6 (11.7 g, 42 mM) was dissolved in methylene chloride (30 ml). Sodium iodide (7.05 g, 47 mM) was added with stirring followed by a solution of the free base in methylene chloride (60 ml). The reaction mixture was cooled to −50° C. then treated with 1M boron tribromide in methylene chloride (35 ml) during a 15 minute period. The reaction mixture was allowed to warm to +5° C. over a 3 hour period then the solvent was evaporated in vacuo. The residue was treated with 6N HCl (30 ml) then heated on a steam bath for 5 minutes. The reaction mixture was cooled in ice, treated with $H_2O$ (30 ml), neutralized with solid sodium bicarbonate then extracted with ethyl acetate (2×100 ml). The ethyl acetate was washed with brine, dried over $Na_2SO_4$ and evaporated in vacuo. The residue was chromatographed on silica ($CHCl_3$—$CH_3OH$—10:1). The pertinent fractions were evaporated in vacuo, the residue was dissolved in ethanol (20 ml), acidified with 6N ethanolic HCl, treated with ether until cloudy and then refrigerated overnight. The white solid was filtered, rinsed with ether and dried. There was thus obtained 800 mg, 33% of the title compound which melts at 257°-9° C.

Analysis Calc'd for $C_{13}H_{22}N_2O_5S_3$.HCl C, 37.26, H, 5.53, N, 6.69 Found: C, 37.03, H, 5.40, N, 6.63

EXAMPLE 15

(+)
5,6-Dihydro-6-(3-hydroxypropyl)-4-ethylamino-4H-thieno[2,3-b]thiopyran-2-sulfonamide-7,7-dioxide hydrochloride, trans isomer

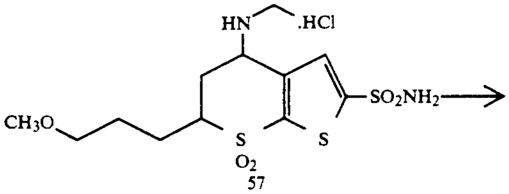

57
(trans-isomer)
(+) rotary enantiomer

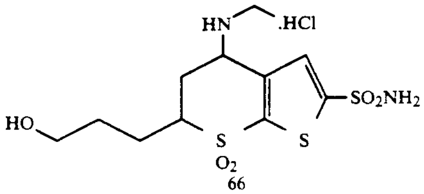

66
(trans-isomer)
(+) rotary enantiomer

The title compound was prepared using substantially the same procedure explained in Example 14, but substituting 0.56 g (1.3 mM) of trans (+)-5,6-dihydro-4-ethylamino-6-(3-methoxypropyl)-4H-thieno[2,3-b]thiopyran-2-sulfonamide-7,7-dioxide hydrochloride (prepared as described in Example 10) as the starting material. There was thus obtained 263 mg (48%) of the title compound which melts at 263°-4° C.

Analysis Calc'd for $C_{12}H_{20}N_2O_5S_3.HCl$ C, 35.59, H, 5.23, N, 6.92 Found: C, 35.56, H, 4.97, N, 6.83

EXAMPLE 16

(−)
5,6-Dihydro-6-(3-hydroxypropyl,)-4-ethylamino-4H-thieno[2,3-b]thiopyran-2-sulfonamide-7,7-dioxide hydrochloride, trans isomer The title compound was prepared using substantially the same procedure explained in Example 14, but substituting 0.85 g (2.0 mM) of trans (−)-5,6-dihydro-4-ethylamino-6-(3-methoxypropyl)-4H-thieno[2,3-b]thiopyran-2-sulfonamide-7,7-dioxide hydrochloride (prepared as described in Example 10) as the starting material. There was thus obtained 240 mg (29%) of the title compound which melts at 263° C.

Analysis Calc'd for $C_{12}H_{20}N_2O_5S_3.HCl.0.5\ H_2O$ C, 34.82, H, 5.36, N, 6.76 Found: C, 34.59, H, 5.36, N, 6.37

EXAMPLE 7

5,6-Dihydro-4-ethylamino-6-(2-furfurylthioethyl)-4H-thieno[2,3-b]thiopyran-2-sulfonamide-7,7-dioxide hydrochloride, trans isomer Step A: 6-Bromoethyl-5,6-dihydro-4-ethylamino-4H-thieno[2,3-b]thiopyran-2-sulfonamide-7,7-dioxide hydrobromide, trans isomer -continued

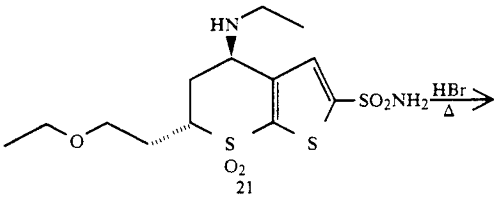

21
(trans-isomer)

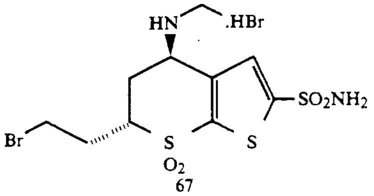

67
(trans-isomer)

The trans isomer of 5,6 dihydro-6-(2-ethoxyethyl)-4-ethylamino-4H-thieno[2,3-b]-thiopyran-2-sulfonamide-7,7-dioxide (5.9 g, 0.0154 mol) (prepared as in Example 2) was stirred at steam bath temperature with 48% hydrobromic acid (100 ml) until the intermediate 6-(2-hydroxyethyl) compound was completely converted to the 6-(2-bromoethyl) product as shown by thin layer chromatography (3 to 5 days). The reaction mixture was concentrated in vacuo at 60° C. bath temperature. A quantitative yield of the title compound was obtained as a pale tan solid (7.7 g).

Step B: 5,6-Dihydro-4-ethylamino-6-(2-furfurylthioethyl)-4H-thieno[2,3-b]thiopyran-2-sulfonamide-7,7-dioxide hydrochloride, trans isomer 67
(trans-isomer)

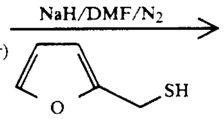

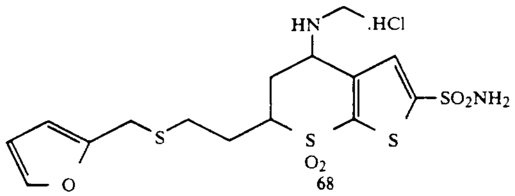

68
(trans-isomer)

The reaction was carried out under nitrogen atmosphere. Sodium hydride (0.48 g, 0.01 mol of a 50% dispersion in mineral oil) was washed with dry petroleum ether. Then dimethylformamide (10 ml) was added and the suspension was stirred at room temperature as furfuryl mercaptan (1.0 ml, 0.01 mol) was added. An immediate reaction occured giving a brown solution. The solution was stirred at room temperature for half an hour and 6-(2-bromoethyl)-5,6-dihydro-4-ethylamino-4H-thieno[2,3-b]thiopyran-2-sulfonamide-7,7-dioxide hydrobromide, trans isomer (1.0 g, 0.002 mol) was added and stirred at room temperature for three-quarters of an hour. Then, the reaction mixture was acidified with 6N HCl (2 ml) and was basified with excess sodium bicarbonate. The mixture was evaporated to dryness under high vaccuum at 50° C. bath temperature. The residual gum was shaken with ethyl acetate (25 ml). The mixture was filtered and the solids were washed with ethyl acetate. The combined ethyl acetate solutions were washed with water, dried, filtered and concentrated in vacuo to yield a viscous amber oil (1.0 g). Chromatography on silica gel gave pure product as an oil (700 mg). The hydrochloride salt was prepared using ethanolic hydrogen chloride to provide 570 mg of white solid. Recrystallization from methanol-ether gave 424 mg., m.p. 196°-198.5° C.

Analysis calc'd for: $C_{16}H_{22}N_2O_5S_4.HCl$; C, 39.45; H, 4.76; N, 5.75 Found: C, 39.45; H, 4.70; N, 5.77

EXAMPLE 18

5,6-Dihydro-4-ethylamino-6-(2-hydroxyethylthioethyl)-4H-thieno[2,3-b]thiopyran-2-sulfonamide-7,7-dioxide hydrochloride, trans isomer

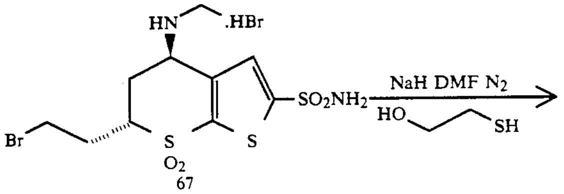

67
(trans-isomer)

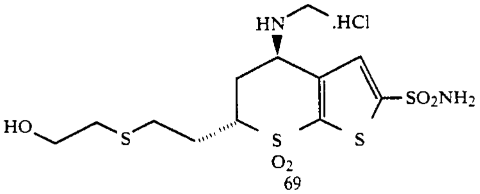

69
(trans-isomer)

The title compound was prepared using substantially the same procedure described in Step B of Example 17, except that mercaptoethanol (0.84 ml, 0.012 mol) was substituted in place of furfuryl mercaptan. Chromatography on silica gel gave 400 mg of pure product as an oil which solidified to a white solid with m.p.=140°-142° C. The hydrochloride salt was prepared using ethanolic hydrogen chloride and was recrystallized from methanol-ether, with m.p.=130°-140° C. with decomposition.

Analysis calc'd for $C_{13}H_{22}N_2O_5S_4.HCl$; C, 34.62; H, 5.14; N, 6.21 Found: C, 35.04; R, 5.44; N, 6.00

EXAMPLE 19

5,6-Dihydro-4-propylamino-6-(3-bromopropyl)-4H-thieno[2,3-b]thiopyran-2-sulfonamide-7,7-dioxide hydrobromide, trans isomer

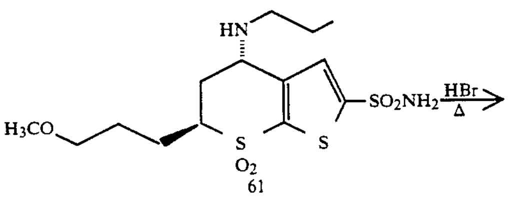

61
(trans-isomer)
(S,S) enantiomer

-continued

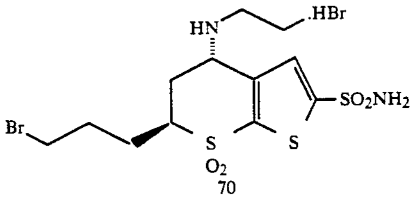

70
(trans-isomer)
(S,S) enantiomer

Employing the procedure substantially as described in Step A of Example 17, but substituting trans 5,6-dihydro-6-(3-methoxypropyl)-4-propylamino-4H-thieno[2,3-b]thiopyran-2-sulfonamide-7,7-dioxide as the starting material, the title compound was prepared in quantitative yield. Melting point=223°-225° C.

Analysis Calc'd for: $C_{13}H_{21}N_2BrO_4S_3.HBr$ C, 32.40, H, 4.60, N, 5.81 Found: C, 32.50, H, 3.73, N, 5.71

EXAMPLE 20

Employing the procedure substantially as described in Step B of Example 17, but substituting trans(S,S) 5,6-dihydro-4-propylamino-6-(3-bromopropyl)-4H-thieno[2,3-b]thiopyran-2-sulfonamide-7,7-dioxide hydrobromide (prepared as described in Example 19) for the 6-bromoethyl compound used therein, and substituting the furfuryl mercaptan used therein with the compounds described in Table II, there were produced the corresponding (S,S)6-(3-substituted-propyl) compounds also described in Table II:

TABLE II

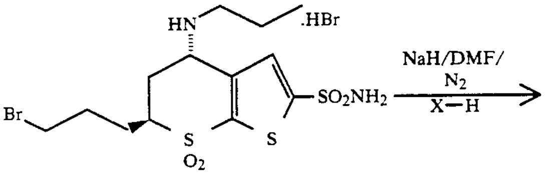

70
(trans-isomer)
(S,S) enantiomer

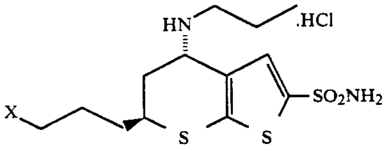

(trans-isomer)
(S,S) enantiomer

| X | Isomer | MP (°C.) |
|---|---|---|
| 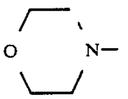 | trans (S,S) | 190* with decomposition |
| $CH_3S$— | trans (S,S) | 185–186 |
| $HOCH_2CH_2S$— | trans (S,S) | 154–156** |
| 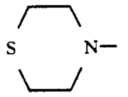 | trans (S,S) | 196*, with decomposition |
| NC— | trans (S,S) | 252–254 |

TABLE II-continued

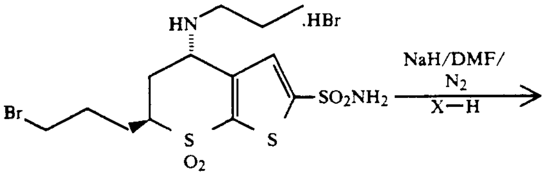

70
(trans-isomer)
(S,S) enantiomer

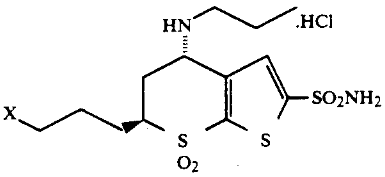

(trans-isomer)
(S,S) enantiomer

| X | Isomer | MP (°C.) |
| --- | --- | --- |
| 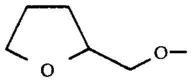 | trans (S,S) | 195-196 |
| $CH_3CH_2S$— | trans (S,S) | 128-135, with decomposition |
| $CH_2$=$CHCH_2O$— | trans (S,S) | 191 |

*= Di-hydrochloride salt
**= Free base

EXAMPLE 21

5,6-Dihydro-(S)-4-propylamino-(S)-6-(3-methanesulfinylpropyl)-4H-thieno[2,3-b]-thiopyran-2-sulfonamide-7,7-dioxide hydrochloride, trans isomer

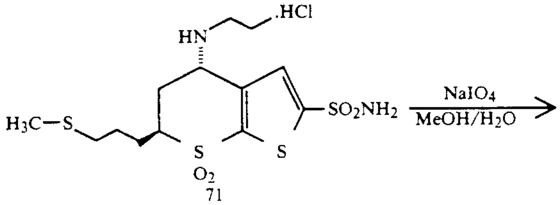

71
(trans-isomer)
(S,S) enantiomer

-continued

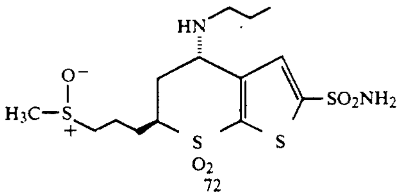

72
(trans-isomer)
(−) rotary enantiomer

A solution of 5,6-Dihydro-(S)-4-propylamino-(S)-6-(3-thiomethoxypropyl)-4H-thieno[2,3-b]thiopyran-2-sulfonamide-7,7-dioxide hydrochloride (1.19 g, 2.65 mmol) in 50 mL of methanol was treated dropwise with a solution of $NaIO_4$ (0.49 g., 2.32 mmol) in 50 mL of water. The solution was stirred for 5 minutes and was then concentrated in vacuo to remove methanol. The resulting aqueous solution was treated by bubbling in sulfur dioxide gas for 4 minutes. The volume of the solution was reduced in half by rotary evaporation in vacuo and the pH of the remaining mixture was adjusted to pH 8 with $NaHCO_3$. The mixture was extracted with a total of 125 mL of ethyl acetate and was washed with 20 mL of saturated aq. NaCl. The organic phase was dried ($MgSO_4$), filtered, and concentrated to dryness in vacuo. Thin layer analysis (silica, 15% methanol in chloroform) indicated a mixture which was then separated using flash chromatography (silica, 15% methanol in chloroform). The desired product was converted to the hydrochloride in ethanol and the solvent was removed in vacuo to give 0.55 g (48%) as a stable white foam, mp=110° C. (with decomposition), $[\alpha]_D^{25}=-13.7°$ ($CH_3OH$).

Analysis for $C_{14}H_{24}N_2O_5S_4.HCl.H_2O.C_2H_5OH$: Calc.: C, 36.39, H, 6.11, N, 5.30 Found: C, 36.17, H, 5.84, N, 5.31

EXAMPLE 22

5,6-Dihydro-(S)-4-propylamino-(S)-6-(3-methanesulfonylpropyl)-4H-thieno[2,3-b]thiopyran-2-sulfonamide-7,7-dioxide hydrochloride, trans isomer

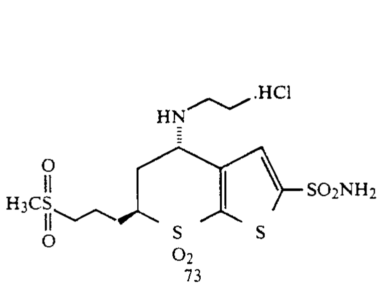

73
(trans-isomer)
(S,S) enantiomer

A solution of 5,6-dihydro-(S)-4-propylamino-(S)-6-(3-thiomethoxypropyl)-4H-thieno[2,3-b]thiopyran-2-sulfonamide-7,7-dioxide hydrochloride (1.17 g, 2.61 mmol) in 25 mL of methanol was treated with a solution of $Na_2WO_4$ (0.086 g, 0.26 mmol) in 1.0 mL of water, followed by adding 800 μL of 30% $H_2O_2$. The resulting mixture was stirred at 45° C. for 2.5 hours. The product mixture was cooled to 25° C. and was then treated with excess $NaHSO_3$ and was stirred 15 minutes. Sulfur dioxide gas was bubbled through the solution for 2 minutes and the pH of the solution was adjusted to pH 8 using $NaHCO_3$. The solution was extracted with a total of 75 mL of ethyl acetate. The organic phase was dried ($Na_2SO_4$), filtered, and concentrated to dryness in vacuo. Thin layer analysis (silica, 10% methanol in chloroform) indicated one component. The product was converted to the hydrochloride in ethanol and the solvent was removed in vacuo to give 0.70 g (56%) as a stable white foam, mp=140° C. (with decomposition)

$[\alpha]_D^{25} = -14.3°$ ($CH_3OH$).

Analysis for $C_{14}H_{24}N_2O_6S_4.HCl.2/3C_2H_5OH$: Calc.: C, 35.99, H, 5.71, N, 5.48 Found: C, 36.36, H, 5.56, N, 5.39

EXAMPLE 23

5-6-Dihydro-4propylamino-6-(3-(4-(1-oxo)-thiomorpholinyl)propyl)-4H-thieno[2,3-b]thiopyran-2-sulfonamide-7,7-dioxide dihydrochloride, trans(−) isomer

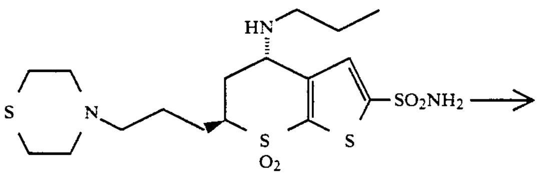

74

(trans-isomer)
(−) rotary enantioner

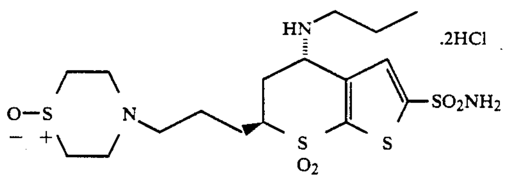

75

(trans-isomer)
(−) rotary enantioner

Using the procedure substantially as described in Example 21, but substituting trans (S,S) 5,6-dihydro-4-propylamino-6-(3-(4-thiomorpholinyl)propyl)-4H-thieno[2,3-b]thiopyran-2-sulfonamide-7,7-dioxide as the starting material, the title compound was obtained. M.P.=227° C.

EXAMPLE 24

5,6-Dihydro-4-propylamino-6-(3-4-(1-dioxo)thiomorpholinyl)propyl)-4H-thieno[2,3-b]thiopyran-2-sulfonamide-7,7-dioxide dihydrochloride

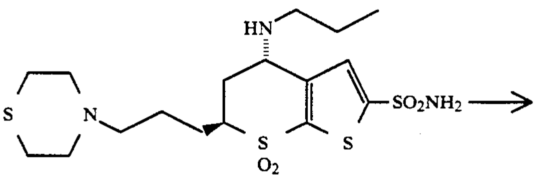

74

(trans-isomer)
(−) rotary enantioner

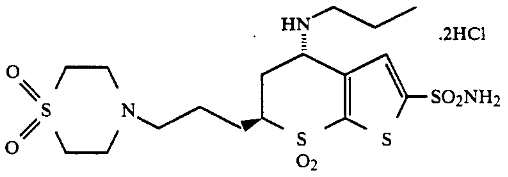

76

(trans-isomer)
(S, S) enantioner

Using the procedure substantially as described in Example 22, but substituting trans (S,S) 5,6-dihydro-4-propylamino-6-(3-(4-thiomorpholinyl)propyl)-4H-thieno[2,3-b]thiopyran-2-sulfonamide-7,7-dioxide as the starting material, the title compound was prepared. M.P.=200° C.

EXAMPLE 25

5,6-Dihydro-(S)-4-propylamino-(S)-6-(3-(2-hydroxyethylsulfinyl)propyl)-4H-thieno[2,3-b]thiopyran-2-sulfonamide-7,7-dioxide hydrochloride, trans isomer

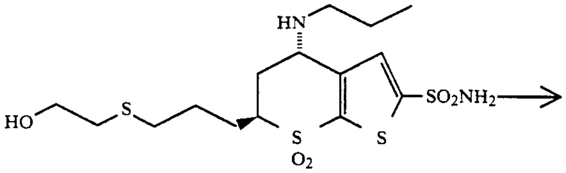

77

(t:ans-isomer)

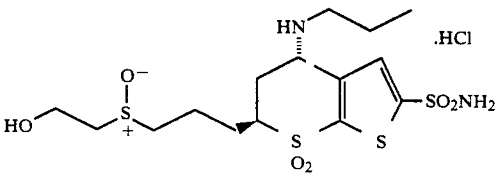

78

(trans-isomer)
(S,S) enantioner

Using the procedure substantially as described in Example 21, but substituting trans (S,S) 5,6-dihydro-4-propylamino-6-(3-(2-hydroxyethylthio)propyl)-4H-thieno[2,3-b]thiopyran-2-sulfonamide-7, 7-dioxide as the starting material, the title compound was prepared. M.P. 120° C.

EXAMPLE 26

5,6-Dihydro-(S)-4-propylamino-(S)-6-(4-butyramide)-4H-thieno[2,3-b]thiopyran-2-sulfonamide-7,7-dioxide hydrochloride, trans isomer

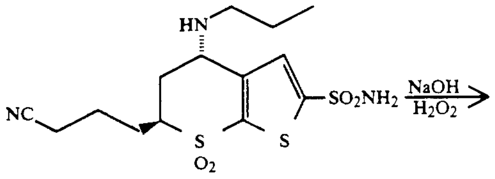

80
(trans-isomer)
(S, S) enantiomer

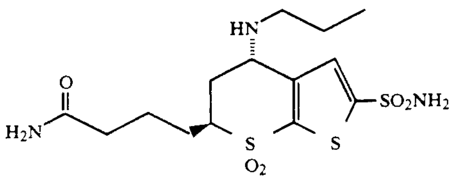

81
(trans-isomer)
(S, S) enantioner

A solution of trans(S,S) 5,6-dihydro-4-propylamino-6-(4-butyronitrile)-4H-thieno[2,3-b]thiopyran-2-sulfonamide-7,7-dioxide (1.4 g., 3.5 mmol) in 40 mL of 1:1 THF/MeOH was treated with 2 mL of 6N NaOH and 400 μL of 30% $H_2O_2$. After 1 hour at room temperature, another 2 mL of 6N NaOH was added in addition to another 400 μL 30% $H_2O_2$. The reaction was stirred overnight at room temperature. The reaction was poured into saturated sodium bicarbonate and extracted with ethyl acetate (3×100 mL). The ethyl acetate layers were combined, dried over $M_gSO_4$, filtered and concentrated in vacuo. The residue was chromatographed on silica gel using 10% MeOH/$CHCl_3$ as eluent to give 480 mg free base. The hydrochloride salt was generated in EtOH and the solid collected and dried in vacuo. M.P.=246°-50° C.

Analysis Calc'd for $C_{14}H_{23}N_2O_5S_3$.HCl: Calc'd: C, 37.70, H, 5.42, N, 9.43 Found: C, 37.66, H, 5.35, N, 9.09

EXAMPLE 27

1-(2-methoxyethyl)-spiropiperidine-4,6'-(6'H)-thieno-[2,3-b]thiopyran-4'-(5'H)-hydroxy-7',7'-dioxide-2'-sulfonamide Step A: Preparation of N-Benzoyl-4-carboxymethyl-4-(2-thienothio)piperidine -continued

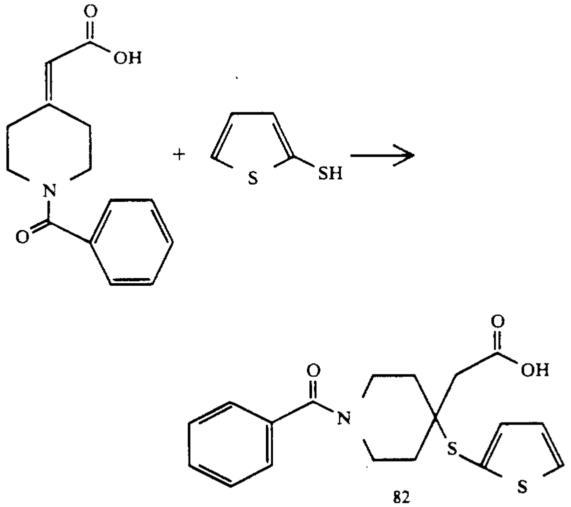

82

A solution of 21.2 g (182 mmol) of 2-mercaptothiophene and 40 g (163 mmol) of N-benzoyl-4-(carboxymethylidine)piperidine in THF (400 ml) was treated with 8.4 g (11.6 mL, 83 mmole) of triethylamine and heated to reflux for 5 hours. The reaction mixture was concentrated to dryness and partitioned between ethyl28 acetate and 0.5N HCl. The aqueous phase was then extracted with ethyl acetate and the combined organics were dried over $MgSO_4$, filtered and concentrated in vacuo. The residue was crystallized from ethyl acetate to give 55 g (93%) of the product, mp=185°-187° C.

$^1$H NMR ($CDCl_3$) δ7.4 (d, 1H), 7.38 (s, 5H), 7.25 (m, 1H), 7.05 (m, 1H), 4.45 (m, 1H), 3.6 (m, 3H), 2.6 (s, 2H), 1.8 (m, 4H).

Elemental analysis for $C_{18}H_{19}NO_3S_2$: Calculated: N, 3.87; C, 59.80; H, 5.29 Found: N, 3.84; C, 60.07; H, 5.17

Step B: Preparation of 1-(Benzoyl)-spiro(piperidine-4, 6'(6'H)-thieno[2, 3-b]thiopyran)-4'(5'H)-one

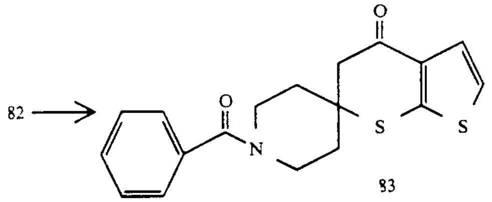

83

A stirring suspension of 42 g (110 mmol) of N-benzoyl-4-(acetic acid)-4-(2-mercaptothiophene) in 800 mL $CH_2Cl_2$ at 10° C. was treated with 2 mL dimethylfo m-amide and then 16.6 g (127 mmol) of oxalyl chloride. The resulting solution was then treated with 52.2 g (348 mmol) of trifluormethanesulfonic acid and warmed slowly to room temperature. The reaction became heterogeneous and was diluted with 700 mL $CH_2Cl_2$ to facilitate stirring. The reaction was stirred for 3 hours at room temperature and then poured into 2 L $H_2O$. The layers were separated and the aqueous phase was extracted with ethyl acetate. The combined organics were dried over $MgSO_4$, filtered and concentrated in vacuo. The residue was crystallized from ethyl acetate to obtain 38.4 g product. MP=145°-147° C.

$^1H$ NMR ($CDCl_3$) δ7.45 (d, 1H), 7.40 (s, 5H), 7.05 (d, 1H), 4.6–4.4 (m, 1H), 3.7–3.65 (m, 1H), 3.5–3.25 (m, 2H), 2.9–2.8 (m, 2H), 2.3–1.6 (m, 4H).

Step C: Preparation of 1-Benzoyl-spiro(piperidine-4, 6'4, 6'-(6'H)-thieno[2, 3-b]thiopyran)-4'(5'H)-one-7', 7'-dioxide 83
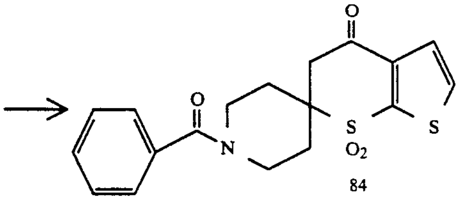
84

A solution of 4 g (11.7 mmole) of 1-benzoylspiro(-piperidine-4,6'-(6'H)-thieno[2,3-b]thiopyran)-4'-(5'H)-one in 50 mL THF at 10° C. was treated with a solution of OXONE ® in $H_2O$ (10.82 g, 17.6 mmol in 50 mL $H_2O$) and warmed slowly to room temperature. After hours at room temperature the reaction mixture was poured into 200 ml of saturated $NaHCO_3$ and extracted with ethyl acetate. The combined organics were dried over anhydrous $MgSO_4$, filtered and concentrated in vacuo. Chromatography of the residue on silica gel (1:1 ethyl acetate/hexane) gave 2.2 g of product, mp=170°–172° C.

$^1H$ NMR ($CDCl_3$) δ7.60 (d, J=5Hz, 1H), 7.50 (d, J=5Hz, 1H), 7.41 (m, 5H), 4.45–4.2 (m, 1H), 4.10–3.80 (m, 1H), 3.6–3.35 (m, 2H), 3.34 (s, 2H), 2.50–2.20 (m, 2H), 2.0–1.65 (m, 2H).

Step D: Preparation of Spiro(piperidine-4, 6'-(6'H)-thieno[2, 3-b]thiopyran)4'-(5'H)-one-7',7'-dioxide hydrochloride 84
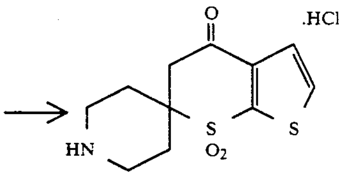
85

A solution of 1-benzoyl-spiro(piperidine-4, 6'-(6'H)-thieno[2,3-b]thiopyran)-4'(5H)-one-7',7'-dioxide (10 g, 26.6 mol) in ethanol (200 ml) was treated with 100 ml 6N HCl and heated to reflux for 24 hrs. The reaction was cooled to room temperature and the solid was collected to give 4.4 g of the title compound, m.p.=110° C.

$^1H$ NMR (DMSO) δ9.4 (m, 1H), 9.0 (m, 1H), 8.18 (d, J=5Hz, 1H), 7.55 (d, J=5Hz, 1H), 3.70–3.6 (m, 2H), 3.55 (s, 2H), 3.4–3.0 (m, 4H), 2.40–2.25 (m, 2H), 2.09–1.95 (m, 2H).

Step E: Preparation of 1-(2-methoxyethyl)-spiro-piperidine-4,6'-(6'H)-thieno[2,3-b]thiopyran-4'-(5'H)-one-7',7'-dioxide -continued 85
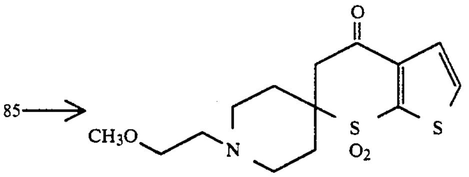
86

To a mixture of spiropiperidine-4,6'-(6'H)-thieno[2,3-b]thiopyran-4'-(5'H)-one-7',7'-dioxide hydrochloride (300 g, 9.75 mm) in acetonitrile (100 ml) was added sodium bicarbonate (1–0 9, 12 mmol) and 2-bromoethyl methyl ether (1.6 g, 15 mmol) and the resulting mixture was heated to 65° C. for 40 hours. The reaction mixture was diluted with water and dilute HCl until neutral. The aqueous was extracted with ethyl acetate (2×100 ml) and the combined extracts were washed with aqueous ammonium chloride and dried over $MgSO_4$/$NaHCO_3$. The solvent was removed by evaporation in vacuo to yield 2.2 g (68%) of the product as an orange oil.

$^1H$ NMR ($CDCl_3$) δ7.81 (d, J=5 Hz, 1H), 7.50 (d, J=5 Hz, 1H), 3.52 (t, J=6 Hz, 2H), 3.35 (s, 3H), 3.30 (s, 2H), 2.99–2.90 (m, 2H), 2.65 (t, J=6 Hz, 2H), 2.50–2.30 (m, 4H), 1.90–1.80 (m, 2H).

Step F: Preparation of 1-(2-methoxyethyl)-spiro-piperidine-4,6'-(6'H)-thieno[2,3-b]thiopyran-4'-(5'H)-hydroxy-7',7'-dioxide 86
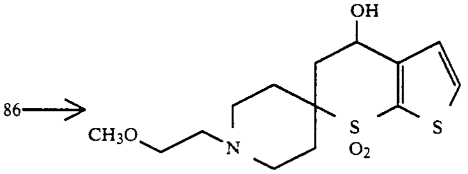
87

To a solution of 1-(2-methoxy)-spiropiperidine-4,6'-(6'H)-thieno[2,3-b]thiopyran-4'-(5'H)-one-7',7'-dioxide (2.2 g, 6.7 mmol) in absolute ethanol (50 ml) and tetrahydrofuran (30 ml) at room temperature was added very slowly sodium borohydride (0.42 g, 11 mmol) and the resulting solution was allowed to stir at room temperature for 1.5 hours. The reaction mixture was quenched with ice and dilute HCl. The aqueous was made neutral with 10N NaOH and aqueous $NaHCO_3$ and extracted with ethyl acetate (5×30 ml). The combined extracts were dried over $MgSO_4$/$NaHCO_3$. The solvent was removed by evaporation in vacuo to yield 2.0 g (90%) of the product as a yellow foam: mp=114°–117° C.

$^1H$ NMR (δ from TMS in DMSO): 7.98 (d, 1H, J=5.1H), 7.20 (d, 1H, J=5.1 Hz), 5.86 (d, 1H, J=6.6 Hz), 4.79–4.76 (m, 1H), 3.43 (t, 2H, J=5.6 Hz), 3.23 (s, 3H), 2.88–2.82 (bm, 2H), 2.68–2.50 (m, 4H), 2.36–2.28 (m, 4H), 1.98 (bt, 2H, J=13 Hz) 1.72 (bt, 2H, J=13 Hz).

Step G: Preparation for 1-(2-methoxyethyl)-spiro-piperidine-4,6'-(6'H)-thieno[2.3-b]thiopyran-4'-(5'H)-hydroxy-7',7'-dioxide-2'-sulfonamide -continued

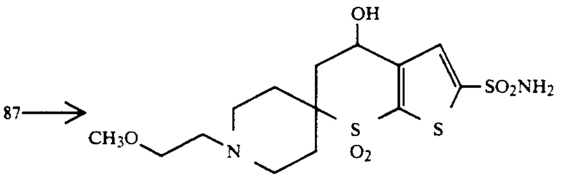

88

To a solution of 1-(2-methoxyethyl)-spiropiperidine-4,6'-(6'H)-thieno[2,3-b]thiopyran-4'-(5'H)-hydroxy-7',7'-dioxide (1.61 g, 4.85 mM) in tetrahydrofuran (50 ml) at −78° C. was added n-butyl lithium (7.0 ml, 10.0 mmol) as a 1.5M solution in hexanes and the resulting solution was stirred at −78° C. for 10 minutes. To this solution was added anhydrous $SO_2$ gas by blowing the gas over the surface of the liquid until the reaction mixture was at pH=1. The solution was then allowed to warm to room temperature and the solvent was removed by evaporation in vacuo to yield an orange semi-solid. The residue was dissolved in water and to this solution was added hydroxylamine-O-sulfonic acid (2.84 g, 25.1 mmol) and sodium acetate (3.60 g, 26.5 mmol) and the mixture was allowed to stir at room temperature for 3 hours. The reaction mixture was diluted with aqueous sat. $NaHCO_3$ and extracted with ethyl acetate (4×50 ml). The combined extracts were dried over $MgSO_4$ and the solvent was removed by evaporation in vacuo. The product was purified with silica gel (0.040-0.063 mm) and 10% methanol/methylene chloride as eluant to yield 1.42 g (88%) as an off-white solid with m.p.=181°-184° C. (with decomposition).

$^1$H NMR (δ from TMS in DMSO): 8.07 (s, 2H), 7.59 (s, 1H), 6.05 (d, 1H, J=6.6 Hz), 4.80 (m, 1H), 3.43 (t, 2H, J=5.7 Hz), 3.23 (s, 3H), 2.84-2.70 (m, 2H), 2.65 (m, 1H), 2.52 (t, 2H, J=5.6 Hz), 2.42-2.24 (m, 3H), 2.02-1.94 (m, 2H), 1.78-1.73 (m, 2H).

Anal. Calc. for $C_{14}H_{22}N_2S_3O_6$: C, 40.96; H, 5.40; N, 6.83. Found: C, 40.86; H, 5.30; N, 6.75.

EXAMPLE 28

1-Propyl-spiropiperidine-4,6'-(6'H)-thieno[2,3-b]thiopyran-4'-(5'H)-hydroxy-7',7'-dioxide-2'-sulfonamide Step A: Preparation of 1-Propyl-spiropiperidine-4,6'-(6'H)-thieno[2,3-b]thiopyran-4'-(5'H)-one-7',7'-dioxide

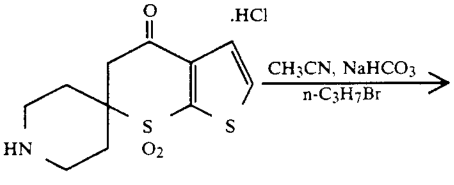

85

-continued

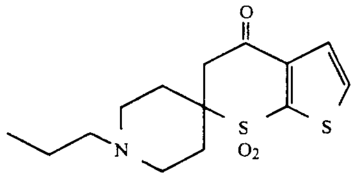

89

A suspension of spiropiperidine-4,6'-(6'H)-thieno[2,3-b]thiopyran-4'-(5'H)-one-7',7'-dioxide hydrochloride (3.00 g, 9.75 mmol) (prepared employing the procedures described in Example 27, Steps A-D), and $NaHCO_3$ (2.46 g, 29.2 mmol) in 125 mL of acetonitrile was blanketed with argon and then treated with 1-bromopropane (1.4 ml, 14.62 mmol). The mixture was heated at 50° C. and stirred 24 hours. The mixture was cooled to 25° C. and concentrated to dryness in vacuo. The residue was partitioned between a total of 200 mL of ethyl acetate and 100 mL of water. The organic phase was washed with 50 mL of saturated aq. NaCl. The organic phase was dried ($MgSO_4$), filtered, and concentrated in vacuo to give 2.43 g (79.5%) of the product as a yellow oil.

$^1$H NMR ($CDCl_3$) δ7.60 (1H, d, J=5.1 Hz), 7.48 (1H, d, J=5.1 Hz), 3.33 (2H, s), 2.86-2.93 (2H, m), 2.22-2.47 (6H, m), 1.85 (2H, d, J=13.5 Hz), 1.46-1-54 (2H, m), 0.90 (3H, t, J=7.32 Hz).

Step B: Preparation of 1-propyl-spiropiperidine-4,6'-(6'H)-thieno[2,3-b]thiopyran-4'-(5'H)-hydroxy-7',7'-dioxide-2'-sulfonamide 89 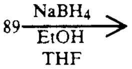

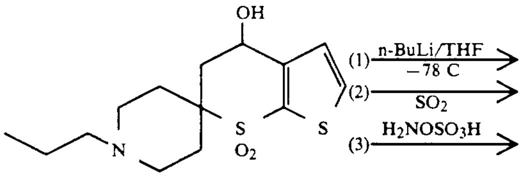

90

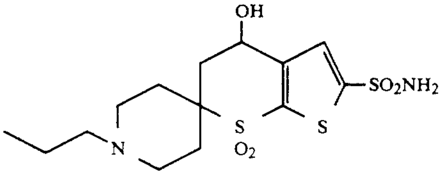

91

Employing substantially the same procedures described in Example 27, Steps F and G, but without isolating the intermediate compound 90, the title compound was obtained, with m.p.=184° C. (for HCl salt).

EXAMPLE 29

1-(2-Methoxyethyl)-spiropiperidine-4,6'-(6'H)-thieno-[2,3-b]thiopyran-4'-(5'H)-propylamino-7',7'-dioxide-2'-sulfonamide dihydrochloride Step A: Preparation of 1-(2-methoxyethyl)-spiro-piperidine-4,6'-(6'H)-thieno[2,3-b]thiopyran-4'-(5'H)-methanesulfonyloxy-7',7'-dioxide-2-sulfonamide

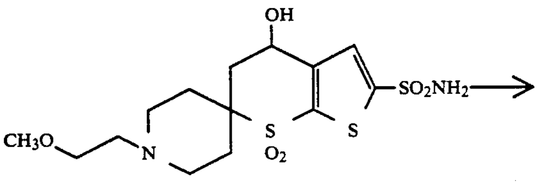

88

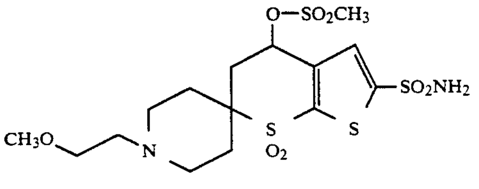

92

To a solution of 1-(2-methoxyethyl)-spiropiperidine-4,6'-(6'H)-thieno[2,3-b]thiopyran-4'-(5'H)-hydroxy-7',7'-dioxide-2'-sulfonamide (0.158 g, 0.385 mmol) in anhydrous tetrahydrofuran (3.5 ml) was added, in portions, triethylamine (0.12 ml, 0.087 g, 0.86 mmol) and methanesulfonic anhydride (0.14 g, 0.78 mmol) and the resulting solution was allowed to stir at room temperature for 24 hours. The reaction mixture was diluted with aq. saturated $NaHCO_3$ and extracted with ethyl acetate (4×25 ml). The combined extracts were dried over $MgSO_4/NaHCO_3$ and the solvent was removed by evaporation in vacuo. The product was purified by flash chromatography with silica gel (0.040-0.063 mM) and 4-20% methanol/methylene chloride as eluant to yield 80.3 mg (43%) of the product as a yellow solid:

$^1H$ NMR (δ from TMS in DMSO): 8.17 (s, 2H), 7.62 (s, 1H), 6.05 (t, 1H, J=5.7Hz), 3.47 (s, 3E), 3.43 (t, 2H, J=5.6Hz), 3.22 (s, 3H), 2.94-2.72 (m, 4H), 2.55 (bm, 2H), 2.36 (bm, 2H), 2.03 (bm, 2H), bm (2H).

Step B: Preparation of 1-(2-methoxyethyl)-spiro-piperidine-4,6'-(6'H)-thieno[2,3-b]thiopyran-4'-(5'H)-propylamino-7',7'-dioxide-2'-sulfonamide dihydrochloride

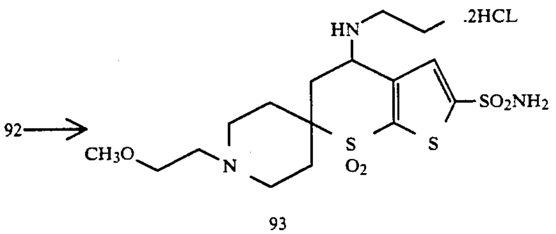

93

To a solution of 1-(2-methoxyethyl)-spiropiperidine-4,6'-(6'H)-thieno[2,3-b]thiopyran-4'-(5'H)-methanesulfonyloxy-7',7'-dioxide-2'-sulfonamide (0.213 g, 0.436 mmol) in acetonitrile (4.0 ml) was added propylamine (1.5 ml, 1.1 g, 18 mmol) and the resulting solution was heated to 65° C. for 24 hours. The reaction mixture was diluted with aq. saturated $NaHCO_3$ and extracted with ethyl acetate (4×30 ml). The combined extracts were dried over $MgSO_4/NaHCO_3$ and the solvent was removed by evaporation in vacuo to yield an orange oil. The product was purified by flash chroatography with silica gel (0.040-0.063 mM) and 8-10% methanol/methylene chloride as eluant to yield 0.101 g (0.223 mmol, 51%) of the product as an off-white foam. Crystallized the product from ethanol/ethyl ether as the HCl salt to provide 89 mg as a white solid: mp=265°-268° C. (with decomposition).

$^1H$ NMR (δ from TMS in DMSO): 10.56 (bs, 1H), 10.17 (bs, 1H), 9.80 (bs, 1H), 8.44 (s, 1H), 8.26 (s, 2H), 4.89 (bm, 1H), 3.76-3.73 (bm, 2H), 3.68 (m, 1H), 3.50-3.30 (m, 8H), 3.07-3.05 (m, 2H), 2.75-2.30 (m, 4H), 2.08-1.98 (m, 2H), 1.90-1.60 (m, 2H), 0.96 (t, 3H, J=7.4Hz).

Anal. Calc'd for: $C_{17}H_{29}N_3O_5S_3.2HCl.0.1\ C_2H_6O.0.6H_2O$; C, 38.26; H, 6.12; N, 7.78 Found: C, 38.28; H, 5.93; N, 7.77.

EXAMPLE 30

4-Ethylamino-6-(4-methoxybenzyl)thieno[2,3-b]thiopyran-2-sulfonamide-7,7-dioxide hydrochloride, trans isomer Step A: Preparation of thieno[2,3-b]thiopyran-4-one-7,7-dioxide-ethylene-ketal

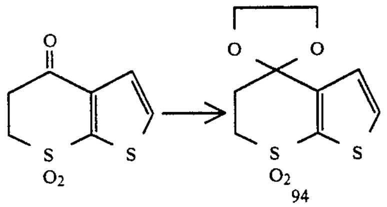

94

A mixture of thieno[2,3-b]thiopyran-4-one (50 g), ethylene glycol (100 mL), p-toluenesulfonic acid (1 g) and toluene (1.5 L) was refluxed under a Dean-Stark apparatus to provide constant removal of water for six hours. To the cooled reaction mixture was added saturated $NaHCO_3$ solution and the layers were separated. The organic phase was extracted twice with $NaHCO_3$ solution (500 mL) and the aqueous layers were back extracted with EtOAc (2×500 ml). The combined organic phases were washed with saturated NaCl solution (3×300 ml) and dried over anhydrous sodium sulfate. Filtration and removal of the solvent, followed by recrystallization of the residue from 1-chlorobutane gave 46 g of off-white solid. M.P.=134°-137° C.

Step B: Preparation of 6-(4-methoxybenzyl)thieno[2,3-b]thiopyran-4-one-7,7-dioxide-ethylene-ketal

94 +

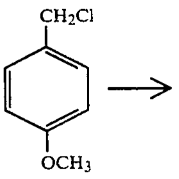

-continued

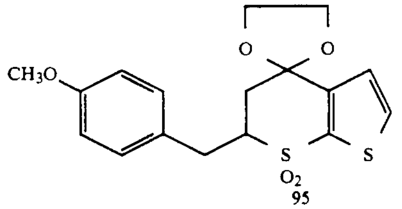

95

A solution of lithium bis(trimethylsilyl)amide in THF (1M, 220 mL, 0.22 mol) was added to a solution of the product from Step A (50 g, 0.20 mol) in THF (750 mL) cooled to −60° C. The solution was stirred for one hour at this temperature and a solution of 4-methoxybenzyl chloride (29.8 mL, 0.22 mol) in THF (250 ml) was added dropwise. The reaction mixture was stirred an additional two hours (−60° C.) and $H_2O$ (65 ml) was added as the temperature was allowed to come to 25° C. The THF was removed under reduced pressure, hexane was added to the residue and the resulting white solid collected by filtration and dried at 40° C. under vacuum, giving 62.7 g. A sample recrystallized from 1-chlorobutane gave mp 160° C.

Anal., Calc'd. for: $C_{17}H_{18}O_5S_2$ (366.44); C, 55.72; H, 4.95. Found: C, 55.83; H, 4.91.

Step C: Preparation of 6-(4-methoxybenzyl)-2-sulfamoyl-thieno[2,3-b]thiopyran-4-one-,7,7-dioxide-ethylene-ketal

95

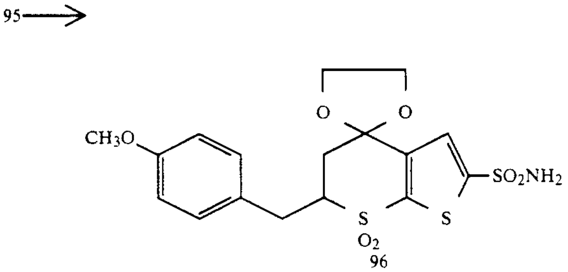

96

A solution of butyl lithium (69.2 mL, 2.5M in hexane, 0.173 mol) was added to a stirred solution of the product from Step B (62.7 g, 0.17 mol) in dry THF (1500 mL) maintained at −78° C. The resulting mixture was stirred at this temperature for an additional 1 hour, then gaseous sulfur dioxide was introduced over the surface of the mixture for 0.25 hour. After warming to ambient temperature the THF was removed in vacuo and the residue was dissolved in 10% aqueous sodium acetate solution (250 mL). Hydroxylamine-O-sulfonic acid (28.8 g) was added and the solution was stirred overnight. The solid that had separated was collected by filtration and triturated with 1-chlorobutane and air-dried to yield 19.2 g off-white solid. A sample purified by flash chromatograph (silica gel, EtOAc/Hexane, 1:1) followed by recrystallization from dichloroethane gave material of mp 220°-222° C.

Anal., Calc'd. for $C_{17}H_{19}NO_7S_3$ (445.528); C, 45.83; H, 4.30; N, 3.14 Found: C, 45.87; H, 4.19; N, 3.12

Step D: Preparation of 6-(4-methoxybenzyl)-4-oxo-thieno[2,3-b]thiopyran-2-sulfonamide-7,7-dioxide -continued

96

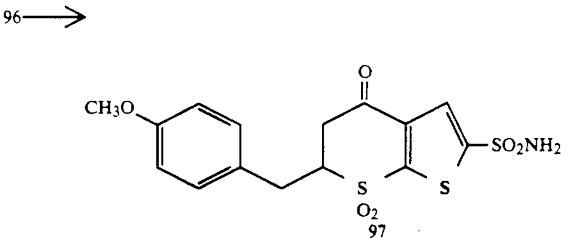

97

A mixture of the product from Step C (11.6 g, 0.026 mol); 200 mL of 6N hydrochloric acid and 200 mL of THF was refluxed for two hours. The THF was removed in vacuo and the residual aqueous mixture was diluted with $H_2O$ (200 mL) and extracted with EtOAc (3×300 mL). The combined organic phase was washed with $H_2O$, brine and dried over anhydrous $MgSO_4$. After filtration and removal of solvent the crude material was treated with 1-chlorobutane followed by trituration with dichloroethane to give 9.0 g of off-white solid. A sample recrystallized from 95% EtOH gave mp 216°-218° C.

Anal. Calc'd for $C_{15}H_{15}NO_6S_3$ (401.48): C, 44.87; H, 3.77; N, 3.49. Found: C, 44.81; H, 3.65; N, 3.47.

Step E: Preparation of cis-4-hydroxy-6-(4-methoxy-benzyl)-thieno[2,3-b]thiopyran-2-sulfonamide-7,7-dioxide

97

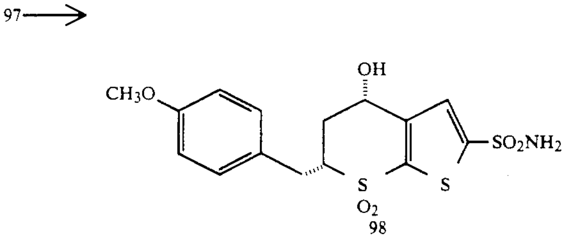

98
(cis-isomer)

Sodium borohydride (0.83 g, 0.022 mol) was added portionwise to a stirred suspension of the product from Step D (8.85 g, 0.022 mol) in $CH_3OH$ (500 mL). After complete addition, the reaction mixture was stirred an additional 0.75 hour and treated with 50 mL of $H_2O$. The $CH_3OH$ was removed in vacuo and the residue was treated with 3N hydrochloric acid (150 mL) and EtoAc (200 mL). The organic phase was washed with 3N hydrochloric acid and brine, then dried over anhydrous $MgSO_4$. Filtration and removal of the solvent in vacuo gave 9.2 g of beige solid. A sample recrystallized from dichloroethane gave mp 175°-177° C.

Anal., Calc'd. for $C_{15}H_{17}NO_6S_3$ (403.498): C, 44.65; H, 4.25; N, 3.47. Found: C, 44.51; H, 3.94; N, 3.44.

Step F: Preparation of N,N-dimethyl-N'-[cis-4-hydroxy-6-(4-methoxybenzyl)thieno[2,3-b]-thiopyran-2-sulfonyl]-formamidine

98

-continued

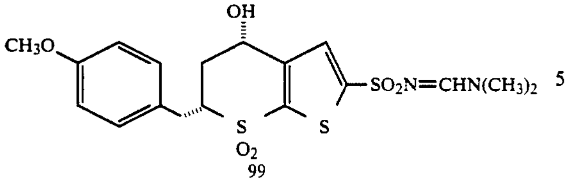

99
(cis-isomer)

A solution of the product from Step E (9.0 g, 0.022 mol) and dimethylformamide dimethylacetal (4.1 mL, 0.031 mol) in $CH_3CN$ (200 mL) was stirred for one hour at ambient temperature. The solvent was removed in vacuo and the residue was partitioned between 1N hydrochloric acid and EtOAc. The EtOAc layer was washed with $H_2O$ and brine and dried over anhydrous $MgSO_4$. Removal of the solvent after filtration gave a yellow foam that was triturated with 1-chlorobutane. The resulting pale yellow solid was dried at 50° C., to give 9.0 g, mp 170°-172° C.

Anal., Calc'd. for $C_{18}H_{22}N_2O_6S_3$ (458.58): C, 47.14; H, 4.84; N, 6.11. Found: C, 47.12; H, 4.82; N, 6.03.

Step G: Preparation of N,N-dimethyl-N'-[cis-4-methanesulfonyloxy-6-(4-methoxybenzoyl)-thieno-[2,3-b]thiopyran-2-sulfonyl]formamidine

98 →

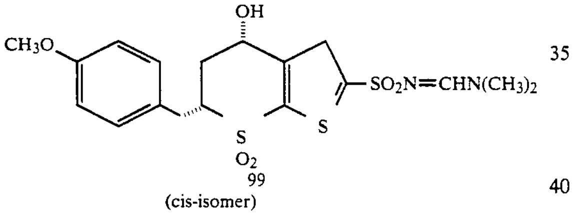

99
(cis-isomer)

Methanesulfonic anhydride (3.97 9, 0.023 mol) was added portionwise to a stirred solution of the product from Step F (8.6 g, 0.019 mol) and $Et_3N$ (3.3 mL, 0.024 mol) in THF (150 mL). After six hours, additional $Et_3N$ (1 mL) and methanesulfonic anhydride (2 g) were added and the mixture was stirred overnight. An additional quantity of $Et_3N$ (2 mL) was added and the reaction mixture was stirred for an additional 24 hours. The solvent was removed in vacuo and the residue was partitioned between $H_2O$ (350 mL) and EtOAc (350 mL). The EtOAc layer was washed with $H_2O$ and brine, and dried over anhydrous $MgSO_4$. Evaporation of the filtered solvent gave 10.7 g of beige foam. Recrystallization of a sample from 1-chlorobutane and dichloroethane gave pure material. M.P. = 155°-156° C.

Anal., Calc'd. for $C_{19}H_{24}N_2O_8S_4$: C, 42.52; H, 4.51; N, 5.22. Found: C, 42.51; H, 4.46; N, 5.14.

Step H: Preparation of N,N-dimethyl-N'-[trans-4-azido-6-(4-methoxybenzyl)thieno[2,3-b]thiopyran-2-sulfonyl]formamidine

100 →

-continued

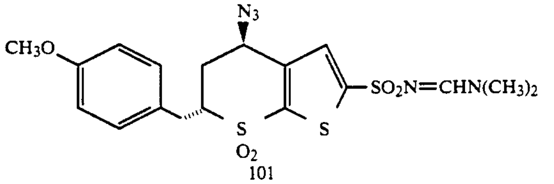

101
(trans-isomer)

A solution of the product from Step G (10.6 g, 0.019 mol) and sodium azide (1.72 g, 0.026 mol) in DMSO (250 mL) was stirred at ambient temperature for one hour. The reaction mixture was diluted with $H_2O$ (200 mL) and extracted with EtOAc (2×400 mL). The organic extracts were washed with $H_2O$ and brine and dried ($MgSO_4$). After filtration and evaporation of the dried solvent, 9.1 g of beige foam was obtained. M.P. 252° C.

Step I: Preparation of trans 4-ethylamino-6-(4-methoxybenzyl)thieno[2,3-b]thiopyran-2-sulfonyl]formamidine

100 →

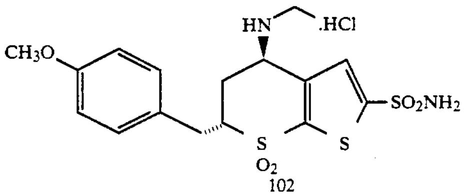

102
(trans-isomer)

Triphenylphosphine (4.8 g, 0.018 mol) was added in portions to a stirred solution of the product from Step H (8.9 g) 0.018 mol) in THF (650 mL). After complete addition the reaction mixture was stirred for four hours at ambient temperature. Acetaldehyde (20 mL, 0.36 mol) was added and stirring was continued overnight. The resulting solution was added to a stirred mixture of $NaBH_4$ (13.6 g, 0.36 mol) in EtOH (150 mL) and stirring was continued for an additional hour. Excess $NaBH_4$ was destroyed by the addition of 5 mL of 3N hydrochloric acid, the THF and EtOH were removed in vacuo. The resulting aqueous solution was extracted with EtOAc. The EtOAc extracts were washed with $H_2O$, brine and dried ($Na_2SO_4$). Removal of the filtered solvent in vacuo followed by flash chromatography (silica gel, $CHCl_3$/MeOH, 95:5) gave 1.03 g off-white solid. This material was converted to the hydrochloride salt with methanolic hydrogen chloride, mp 252° C.

Anal., Calc'd. for $C_{17}H_{22}N_2O_5S_3$+HCl (467.027); C, 43.72; H, 4.96; N, 5.99. Found: C, 43.37; H, 5.04; N, 5.85.

EXAMPLE 31

Resolution of trans-4-ethylamino-6-(4-methoxybenzyl)-thieno[2,3-b]thiopyran-2-sulfonamide-7,7-dioxide 102 →
(trans-isomer)
(free-base)

-continued

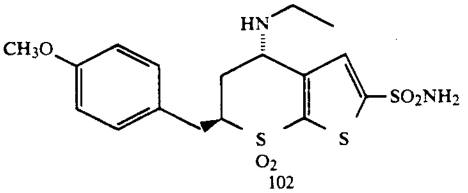

102
(trans-isomer)
(−) rotary enantiomer

A solution of the title compound (22.2 g, 0.051 mol) in acetone (400 mL) was added to a warm solution of di-p-toluoyl-D-(+)-tartaric acid (19.7 g, 0.051 mol) in acetone (400 mL). The resulting warm solution was filtered and allowed to cool gradually to ambient temperature. The resulting solid was collected and recrystallized twice from acetone to give 8.09 g white solid, with mp 199° C. HPLC analysis indicated one enantiomeric salt. The acetone filtrates were reworked to provide another 5.42 g of comparable enantiomeric purity. The combined solids were partitioned between $NaHCO_3$ solution and EtOAc. The EtOAc layer was washed with $H_2O$, brine and dried ($Na_2SO_4$). The filtered solution, after drying, was evaporated under reduced pressure to give 6.65 g, mp 161°-163°, [α]=−30.3°.

EXAMPLE 32

4-Ethylamino-6-(4-hydroxybenzyl)thieno[2,3-b]thiopyran-2-sulfonamide-7,7-dioxide hydrochloride, trans, (−) isomer

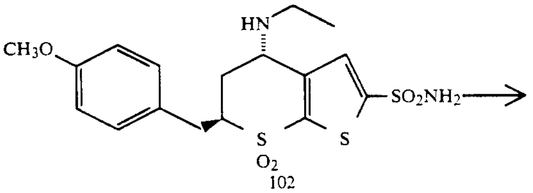

102
(trans-isomer)
(−) rotary enantiomer

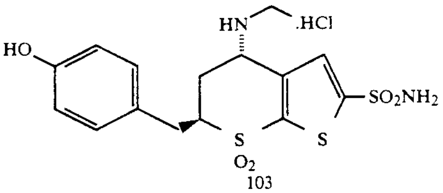

103
(trans-isomer)
(−)rotary enantiomer

A solution of $BBr_3$ in $CH_2Cl_2$ (45 mL, 1M, 0.045 mol) was added dropwise to a stirred solution of (−) trans-4-ethylamino-6-(4-methoxybenzyl)thieno[2,3-b]thiopyran-2-sulfonamide-7,7-dioxide (6.65 g, 0.015 mol) in $CH_2Cl_2$ (200 mL) at 0° C. After one hour at ambient temperature an additional 5 mL of 1M $BBr_3$ in $CH_2Cl_2$ was added and stirring was continued for an additional hour. Water (100 mL) was added dropwise and the pH of the aqueous layer was adjusted to 7.5 with 10% aqueous NaOH solution. The resulting mixture was extracted with EtOAc (3×400 mL) and the combined organic layers were washed with $H_2O$, brine and dried ($Na_2SO_4$). Evaporation in vacuo of the filtered dried solvent gave 6.6 g off-white solid. Treatment of this material with methanolic hydrogen chloride, followed by recrystallization from EtOH-ether gave the hydrochloride salt with mp 185°-190° C.

Anal., Calc'd. for $C_{16}H_{20}N_2O_5S_3$+HCl (453.001): C, 42.42; H, 4.67; N, 6.18. Found: C, 42.49; H, 4.90; N, 6.13. $[\alpha]_D^{25}=-11.7°$ (c=1.075, $CH_3OH$).

EXAMPLE 33

4-Ethylamino-6-(4-hydroxybenzyl)thieno[2,3-b]thiopyran-2-sulfonamide-7,7-dioxide hydrochloride, trans isomer

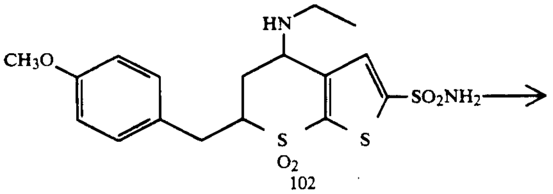

102
(trans-isomer)

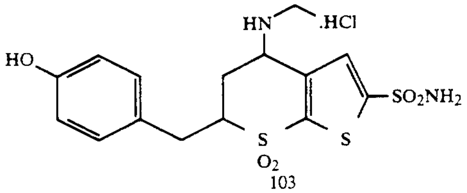

103
(trans-isomer)

Employing the procedure substantially as described in Example 32, but starting with the enantiomeric racemate of the trans isomer of the starting material instead of trans (−), the title compound was obtained, with melting point=>265° C.

Anal., calc'd. for $C_{16}H_{20}N_2O_5S_3$+HCl(453.001): C, 42.42; H, 4.67; N, 6.18 Found: C, 42.08; H, 4.59; N, 5.86

EXAMPLE 34

6-(3-Dimethylaminomethyl-4-hydroxybenzyl)-4-ethylamino-thieno[2,3-b]thiopyran-2-sulfonamide dihydrochloride, trans, (−) isomer

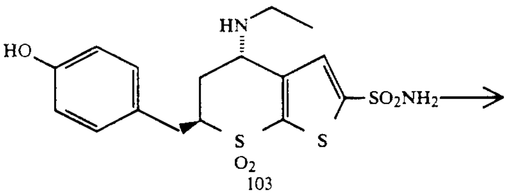

103
(trans-isomer)
(−) rotary enantiomer

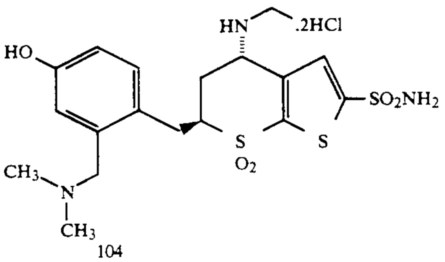

104
(trans-isomer)
(−) rotary enantiomer

A mixture of (−) trans 4-ethylamino-6-(4-hydroxybenzyl)thieno[2,3-b]thiopyran-2-sulfonamide-7,7-dioxide (6.63 g, 0.016 mol), formaldehyde (0.6 mL, 0.008 mol) and 40% aqueous dimethylamine (2.7 mL, 0.024 mol) in EtOH (50 mL) was heated under reflux overnight. The volatiles were removed in vacuo and the residue was diluted with $H_2O$ (200 mL). The resulting aqueous solution (pH 8) was extracted with EtOAc (5×200 mL). The combined extracts were washed with brine and dried ($Na_2SO_4$). Removal of the filtered, dried solvent in vacuo gave 6.9 g of residue. This material was subjected to flash chromatography (silica gel, $CHCl_3$/MeOH/$NH_4OH$; 90:9:1) and 3.69 g of the title compound as free base, $[\alpha]_D^{25}=-21.8°$ (C=0.84; MeOH) and 3.38 g of recovered starting material were obtained. Conversion of the title free base to dihydrochloride with methanolic hydrogen chloride followed by recyrstallization from EtOH gave material of mp 188°-193° C.

Anal. Calc'd. for $C_{19}H_{27}N_3O_5S_3+2HCl+H_2O$ (564.47): C, 40.42; H, 5.54; N, 7.44. Found: C, 40.13; H, 5.20; N, 7.46.

$[\alpha]_D^{25}=+1.32°$ (c=1.35, MeOH).

EXAMPLE 35

6-(3-Dimethylaminomethyl-4-hydroxybenzyl)-4-ethylamino-thieno[2,3b]thiopyran-2-sulfonamide dihydrochloride, trans isomer

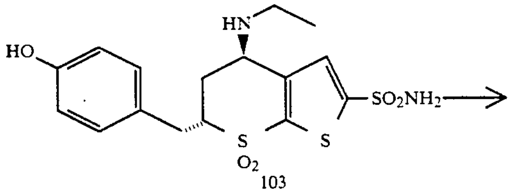

103
(trans-isomer)

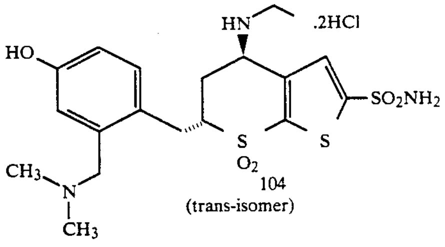

104
(trans-isomer)

Employing the procedure substantially as described in Example 34, but starting with the enantiomeric racemate of the trans isomer of the starting material instead of trans (−), the title compound was obtained with melting point =275° C.

Anal., Calc'd. for $C_{19}H_{27}N_3O_5S_3+2HCl$ (546.55): C, 41.75; H, 5.35; N, 7.69 Found: C, 41.73; H, 5.57; N, 7.31

EXAMPLE 36

4-Ethylamino-6-tetrahydrofurfuryl-thieno[2,3-b]thiopyran-2-sulfonamide-7,7-dioxide hydrogen maleate, trans isomer Employing the procedures substantially as described in Example 30, but substituting tetrahydrofurfuryl trifluoromethanesulfonate for the 4-methoxybenzyl chloride used in Step B, and converting the final product in Step H to the maleic acid salt instead of the HCl salt, the title compound was obtained with melting point=198°-199° C.

Anal Calc'd for: $C_{14}H_{22}N_2O_5S_3.C_4H_4O_4$; C, 42.34; H, 5.13; N, 5.49 Found: C, 42.32; H, 5.11; N, 5.34

EXAMPLE 37

5,6-Dihydro-4-ethylamino-6-[3-(imidazol-1-yl)propyl]-4H-thieno[2,3-b]thiopyran-2-sulfonamide-7,7-dioxide dihydrochloride, trans isomer Step A: 5,6-Dihydro-4-ethylamin0-6-(3-bromopropyl)-4H-thieno[2,3-b]thiopyran-2-sulfonamide 7,7-dioxide hydrobromide, trans isomer

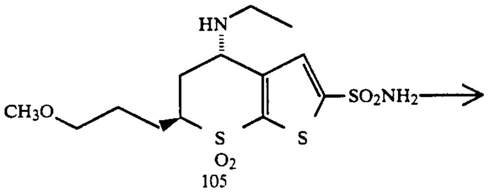

105
(trans-isomer)

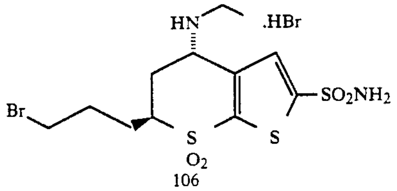

106
(trans-isomer)

Employing the procedure substantially as described in Step A of Example 17, but substituting trans 5,6-dihydro-6-methoxypropyl-4-ethylamino-4H-thieno-[2,3-b]thiopyran-2-sulfonamide-7,7-dioxide as the starting material, the title compound was obtained.

Step B: 5,6-Dihydro-4-ethylamino-6-[3-(imidazol-1-yl) propyl]-4H-thieno[2,3-b]thiopyran-2-sulfonamide-7,7-dioxide dihydrochloride, trans isomer 106
(trans-isomer)

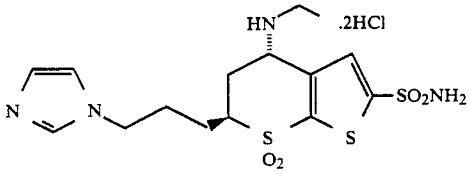

107
(trans-isomer)

Employing the procedure substantially as described in Step B of Example 17, but substituting the product of Step A above for the 6-bromoethyl compound therein, and substituting imidazole for the furfuryl mercaptan therein, the title compound was obtained with m.p.=>200° C. (with decomposition).

Anal Calc'd for: $C_{15}H_{22}N_4O_4S_3.2HCl.0.5H_2O$; C, 35.99; H, 5.03; N, 11.20 Found: C, 35.74; H, 4.81; N, 10.92

EXAMPLE 38

5,6-Dihydro-(S)-4-ethylamino-(S)-6-(3-cyanopropyl)-4H-thieno[2,3-b]thiopyran-2-sulfonamide-7,7-dioxide hydrochloride, trans isomer

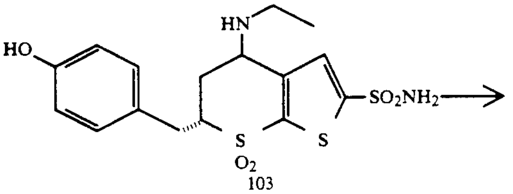

103
(trans-isomer)

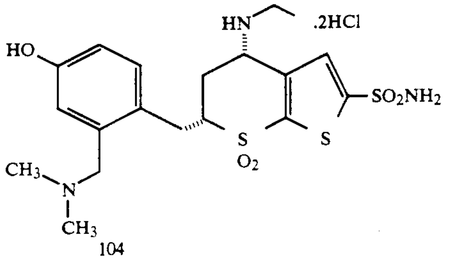

104
(trans-isomer)

Employing the procedure substantially as described in Step B of Example 37, but substituting the trans (S,S) isomer for the trans racemate of the 6-bromopropyl compound used therein, and substituting sodium cyanide for the imidazole used therein, the title compound was obtained. M.P.=213°-215° C.

Anal calc'd for: $C_{13}H_{19}N_3O_4S_3.HCl$; C, 37.72; H, 4.63; N, 10.15 Found: C, 37.45; H, 4.77; N, 9.92

EXAMPLE 39

5,6-Dihydro-6-allyloxymethyl-4-ethylamino-4H-thieno[2,3-b]thiopyran-2-sulfonamide-7,7-dioxide hydrochloride Step A: 5,6-Dihydro-6-allyloxymethyl-4-methoxyethoxy-4H-thieno[2,3-b]-thiopyran-2-sulfonamide-7,7-dioxide

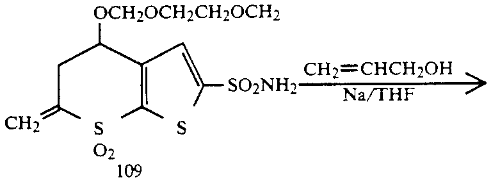

109

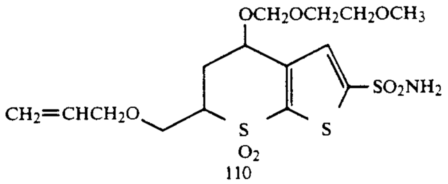

110

Sodium (4.6 g., 0.20 m) was added portionwise to allyl alcohol (110 ml.) with stirring under nitrogen. After solution was effected, it was added to 5,6-dihydro-4-methoxyethoxymethoxy-6-methylene-4H-thieno[2,3-b]thiopyran-2-sulfonamide-7,7-dioxide, (32.5 g, 0.085 m), dissolved in tetrahydrofuran (75 ml.). After stirring at ambient temperature for 21 hours, the reaction mixture was cooled in ice, acidified with 6N hydrochloric acid (90 ml., 0.24 m) and then basified with saturated sodium bicarbonate solution. The mixture was concentrated in vacuo and the residue distributed between ethyl acetate (600 ml) and $H_2O$ (250 ml.). The aqueous layer was separated and extracted with ethyl acetate (2×250 ml.), the combined ethyl acetate layers were washed twice with brine, dried over sodium sulfate, and concentrated in vacuo to yield 33.1 g. (88%) of viscous oily product.

Step B: 5,6-Dihydro-6-allyloxymethyl-4-hydroxy-4H-thieno[2,3-b]thiopyran-sulfonamide-7,7-dioxide

110

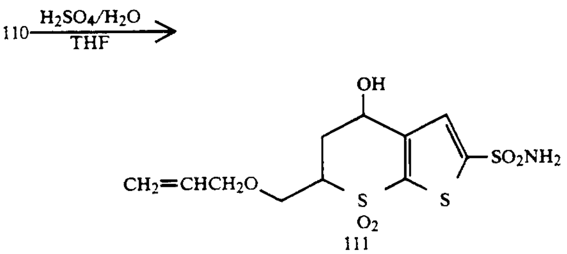

111

A solution of 5,6-dihydro-6-allyloxymethyl-4-methoxyethoxymethoxy-4H-thieno[2,3-b]thiopyran-2-sulfonamide-7,7-dioxide (33.0 g., 0.075 m) in tetrahydrofuran (230 ml.) was cooled to −5° C. and stirred while a solution of concentrated sulfuric acid (230 ml.) in water (230 ml.) was added dropwise over 45 min. while maintaining the temperature below 5° C. After stirring at −5° C. for 1 hour and at ambient temperature for 3 hours, the mixture was added slowly to a stirred suspension of sodium bicarbonate (750 g) in ethyl acetate (900 ml.) and ice. After 30 minutes with periodic additions of saturated sodium bicarbonate to render the mixture basic, it was filtered and the solids were washed with ethyl acetate. The combined filtrate and washings were washed twice with $H_2O$, dried over sodium sulfate and concentrated in vacuo to afford 25.9 g (98%) of an amorphous product.

Step C: 5,6-Dihydro-6-allyloxymethyl-4-ethylamino-4H-thieno[2,3-b]thiopyran-2-sulfonamide-7,7-dioxide

111

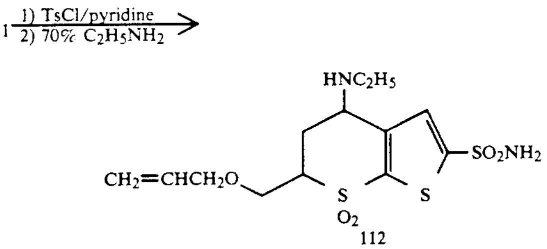

112

A stirred solution of 5,6-dyhydro-6-allyloxymethyl-4-hydroxy-4H-thieno[2,3-b]thiopyran-2-sulfonamide-7,7-dioxide (12.5 g, 0.035 m) in dry pyridine (65 ml.) was cooled to −10° C. under nitrogen while p-toluenesulfonyl chloride (14.7 g., 0.077 m) was added in one portion. After stirring at −10° C. for 5 hours, the mixture was further cooled to −20° C. and 70% aqueous ethylamine (150 ml.) was added over 45 minutes while maintaining the temperature between −20° C. and −10° C. The mixture was stirred at ambient temperature for 1.5 hours and then at 50° C. for 16.5 hours, after which it was concentrated in vacuo. The residue was distributed between ethyl acetate (600 ml) and saturated sodium bicarbonate solution (300 ml.), the aqueous layer was separated and extracted with ethyl acetate (2×300 ml.), the combined ethyl acetate extracts were washed twice with $H_2O$ and concentrated to approximately 250 ml. in vacuo. The solution was extracted with 3N hydrochloric acid (2×150 ml.) and washed with $H_2O$ (150 ml.), the combined acid extracts and $H_2O$ wash were basified with sodium bicarbonate and extracted with ethyl acetate (3×350 ml.). The combined extracts were washed twice with $H_2O$, dried over sodium sulfate and concentrated in vacuo to yield 6.3 g (47%) of product as an isomeric mixture.

The isomeric mixture of 5,6-dihydro-6-allyloxymethyl-4-ethylamino-4H-thieno[2,3-b]thiopyran-2-sulfonamide-7,7-dioxide (6.2 g.) was chromatographed on silica gel on a 100 mm. diameter Still column, eluting with chloroform/methane/ammonium hydroxide, 95:5:0.5. After re-chromatographing the fractions containing a mixture of isomers, a total of 1.2 g. of the pure α-isomer was obtained, along with 1.6 g of the pure β-isomer.

The α-isomer (1.2 g., 0.0032 m) was dissolved in absolute ethanol (10 ml.), 5.95N ethanolic hydrogen chloride (1.0 ml., 0.0060 m) was added and the solution was diluted to incipient turbidity with anhydrous ether. The resultant hydrochloride salt was recrystallized from absolute ethanol (10 ml.) - anhydrous ether (8 ml.) to yield 0.81 g of an analytical sample of the α-isomer melting at 148°-150° C.

Anal. Calc'd for $C_{13}H_{20}N_2O_5S_3$.HCl: C, 37.45; H, 5.08; N, 6.72 Found: C, 37.21; H, 5.04; N, 6.69

The β-isomer (1.6 g., 0.0042 m) was dissolved in absolute ethanol (10 ml.), 5.95N ethanolic hydrogen chloride (1.2 ml., 0.0071 m) was added and the solution diluted to incipient cloudiness with anhydrous ether. The product was recrystallized from absolute ethanol (10 ml.)- anhydrous ether (12 ml.) to yield 1.13 g of the analytically pure hydrochloride salt of the β-isomer, melting at 204°-205.5° C.

Anal. Calc'd for $C_{13}H_{20}N_2O_5S_3$.HCl: C, 37.45; H, 5.08; N, 6.72 Found: C, 37.75; H, 4.72; N, 6.89

EXAMPLE 49

5,6 Dihydro-4-ethylamino-6-(3-hydroxypropoxy)methyl-4H-thieno[2,3-b]thiopyran-2-sulfonamide-7,7-dioxide hydrochloride (α-isomer)

Step A: 5,6-Dihydro-6-allyloxymethyl-4-methoxyethoxymethoxy-4H-thieno[2,3-b]-thiopyran

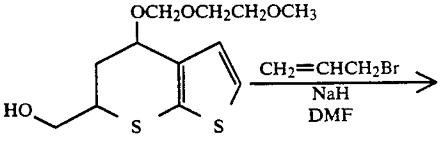

113

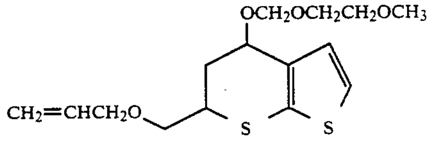

114

Sodium hydride, 50% suspension in mineral oil (7.2 g, 0.15 m), was washed with hexane to remove mineral oil. The washed solid was suspended in dry dimethylformamide, 100 ml., and stirred at ambient temperature in a nitrogen atmosphere while a solution of 5,6-dihydro-6-hydroxymethyl-4-methoxyethoxymethoxy-4H-thieno[2,3-b]thiopyran, 35.0 g. (0.12 m), in dry dimethylformamide, 100 ml, was added over 10 minutes. After stirring at ambient temperature for 1.5 hours, allyl bromide, 29.0 g. (0.24 m), was added over 15 minutes and the mixture was stirred at ambient temperature for 16 hours. The reaction mixture was concentrated in vacuo and the residue was suspended in 250 ml. $H_2O$ containing 30 ml. of 6N hydrochloric acid. The mixture was extracted with ethyl acetate (300 ml. and 2×250 ml.), the combined extracts were washed successively with brine, saturated sodium bicarbonate, 10% sodium bisulfite, brine, and then dried over sodium sulfate. After filtering, the filtrate was concentrated in vacuo to yield 36.94 g. (93%) of product as a brown, fluid oil.

Step B: 5,6-Dihydro-6-allyloxymethyl-4-methoxyethoxymethoxy-4H-thieno[2,3-b]thiopyran-2-sulfonamide

114

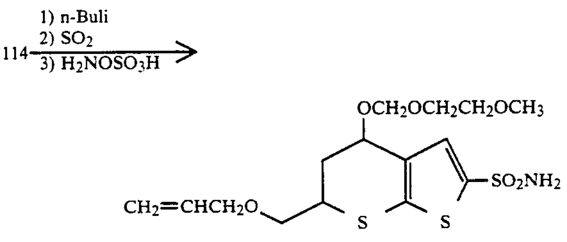

115

A solution of 5.6-dihydro-6-allyloxymethyl-4-methoxyethoxymethoxy-4H-thieno[2,3-b]thiopyran, 13.2 g (0.040 m), in dry tetrahydrofuran, 75 ml., was cooled to −78° C. with stirring under nitrogen and 1.6 M n-butyllithium, 30 ml. (0.048 m), was added over 30 minutes keeping the temperature below −60° C. After stirring at −78° C. for one hour, sulfur dioxide was passed over the surface of the reaction mixture intermittently over one hour while maintaining the temperature below −45°. The mixture was stirred at −78° C. for one hour and then allowed to warm to ambient temperature over 30 minutes. The mixture was concentrated in vacuo and the residue treated with $H_2O$ containing sodium acetate, 9.0 g. (0.11 m), and stirred with ice-bath cooling while hydroxylamine-O-sulfonic acid, 11.3 g. (0.10 m) was added over 10 minutes. An additional 3.1 g. (0.038 m) sodium acetate was added and the mixture was stirred at ambient temperature for 17 hours. Saturated sodium bicarbonate solution, 80 ml., was added and the mixture was extracted with chloroform (200 ml. and 2×150 ml.). The combined extracts were washed twice with brine, dried over sodium sulfate and concentrated in vacuo to yield 15.43 g. (94%) of viscous, brown oily product, which was used in the subsequent reaction without further purification.

Step C: 5,6-Dihydro-4-acetamido-6-allyloxymethyl-4H-thieno[2,3-b]thiopyran-2-sulfonamide

115

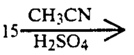

-continued

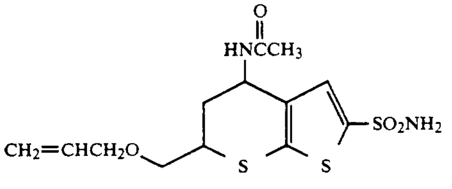

116

A solution of 5,6-dihydro-6-allyloxymethyl-4-methoxyethoxymethoxy-4H-thieno[2,3-b]thiopyran-2-sulfonamide, 12.6 g (0.031 m) in acetonitrile, 105 ml., was cooled to 0° C. with stirring under nitrogen while concentrated sulfuric acid, 30.4 g. (0.31 m) was added dropwise over 30 minutes. The mixture was stirred at 0° C. for 30 minutes and then at ambient temperature for 22 hours. The mixture was poured into ice and $H_2O$ (225 ml.), rendered basic by the slow addition of sodium bicarbonate, 135 g., and extracted with ethyl acetate (300 ml. and 2×150 ml.). The combined extracts were washed with brine, dried over sodium sulfate and concentrated in vacuo to yield tan solid product weighing 8.59 g. (70%).

Step D: 5,6-Dihydro-4-acetamido-6-)3-hydroxypropoxy)-methyl-4H-thieno[2,3-b]thiopyran-2-sulfonamide

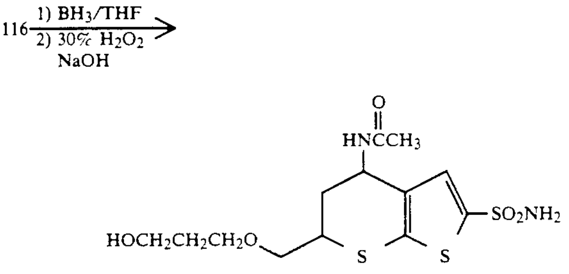

117

A solution of 5,6-dihydro-4-acetamido-6-allyloxymethyl-4H-thieno[2,3-b]thiopyran-2-sulfonamide, 2.5 g. (0.0069 m), in dry tetrahydrofuran, 125 ml., was cooled to −5° C. with stirring under nitrogen while 1.0M boranetetrahydrofuran complex, 30 ml. (0.030 m) was added over 5 minutes. After stirring at ambient temperature for 30 minutes, an additional 6 ml. of 1.0M borane-tetrahydrofuran complex was added in one portion and reaction at ambient temperature was continued for 30 minutes more. The reaction mixture was cooled to −5° C. and 5N sodium hydroxide, 14 ml. (0.07 m), was added dropwise, followed by the slow addition of 10% hydrogen peroxide, 3.97 g. (0.035 m). After stirring at ambient temperature for 16 hours, 10% sodium sulfite, (15 ml.), was added. The mixture was acidified with 6N hydrochloric acid, 12 ml., and then basified with saturated sodium bicarbonate. After concentration in vacuo to remove tetrahydrofuran below 30° C., the aqueous suspension was extracted with ethyl acetate (3×75 ml.), the combined extracts were washed twice with brine, dried over sodium sulfate and evaporated in vacuo to yield 1.74 g. (66%) of product.

Step E: 5,6-Dihydro-4-acetamido-6-(3-hydroxypropoxy)-methyl-4H-thieno[2,3-b[thiopyran-2-sulfonamide-7,7-dioxide -continued

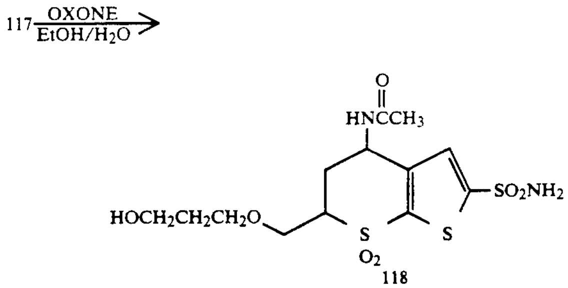

118

A solution of 5,6-dihydro-4-acetamido-6-(3-hydroxypropoxy)methyl-4H-thieno[2,3-b]thiopyran-2-sulfonamide, 1.60 g. (0.0042 m), in ethanol, 15 ml., and $H_2O$, 6 ml., was stirred with OXONE®, 3.07 g. (0.0050 m), at ambient temperture for 3 hours. An additional 0.65 g. of OXONE® was added and stirring was continued for 1.5 hours more. The mixture was rendered basic wih sodium bicarbonate and filtered. The filtrate was concentrated in vacuo to remove ethanol and leave an aqueous suspension. The filtered solid was washed with ethyl acetate, 100 ml, and the washings were used to extract the above aqueous suspension, the aqueous layer was separated and extracted with ethyl acetate (2×75 ml.), the combined extracts were washed with brine and dried over sodium sulfate. Evaporation i-n vacuo afforded 0.77 g. (45%) of product.

Step F: 5,6-Dihydro-4-ethylamino-6-(3-hydroxypropoxy)methyl-4H-thieno[2,3-b]thiopyran-2-sulfonamide-7,7-dioxide (α-Isomer)

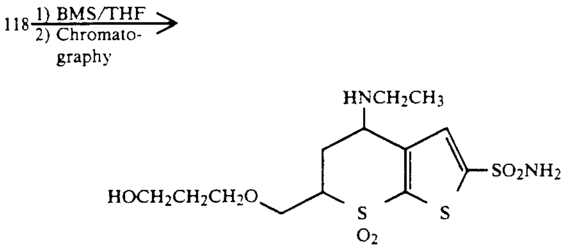

119

α-isomer

A solution of 5,6-dihydro-4-acetamido-6-(3-hydroxypropoxy)methyl-4H-thieno[2,3-b]thiopyran-2-sulfonamide-7,7-dioxide, 0.75 g. (0.0018 m) in dry tetrahydrofuran, 10 ml., was stirred at ambient temperature under nitrogen while 10M borane-methylsulfide complex, 1.8 ml. (0.018 m.), was added over 20 minutes. The mixture was refluxed over 2 hours, and then dimethylsulfide was distilled through a Vigreaux column with continual heating for 2 hours more. With cooling in an ice-acetone bath, excess borane-methylsulfide was decomposed by the dropwise addition of absolute methanol, 2 ml., followed by 6N hydrochloric acid, 9 ml. The mixture was heated on a steam bath with stirring for 30 minutes and then concentrated in vacuo to remove tetrahydrofuran and methanol. Ethyl acetate, 15 ml., was added to the aqueous suspension which was rendered basic with sodium bicarbonate. The aqueous layer was re-extracted with ethyl acetate (2×25 ml.), the combined extracts were washed successively with saturated sodium bicarbonate and with brine, dried over sodium sulfate and concentrated in vacuo to yield 0.56 g (78%) of oily product.

Chromotography on silica gel on a 40 mm. diameter Still column, eluting with chloroform/methanol/ammonium hydroxide, 90:10:1, afforded 0.18 g. of the α-isomer which was dissolved in absolute ethanol, 3 ml., treated with 5.95N ethanolic hydrogen chloride, 0.1 ml., and diluted to incipient turbidity with anhydrous ether. The resultant crystalline hydrochloride salt weighed 0.14 g. and melts at approximately 120° C. (with decomposition).

Anal. Calcd. for $C_{13}H_{22}N_2O_6S_3$.HCl: C, 35.89; H, 5.33; N,6.44 Found: C, 35.63; H, 5.40; N, 6.26

EXAMPLE 41

5,6-Dihydro-6-allyloxymethyl-4-ethylamino-4H-thieno[2,3-b]thiopyran-2-sulfonamide-7,7-dioxide ((−)α-Isomer: (+) α-Isomer; (−) β-Isomer; and (+) β-Isomer)

Step A: Preparation of 5,6-Dihydro-4-acetamido-6-allyloxymethyl-4H-thieno[2,3-b]thiopyran-2-sulfonamide-7,7-dioxide, A warm solution of 5,6-dihydro-4-acetamido-6-allyloxymethyl-4H-thieno[2,3-b)thiopyran-2-sulfonamide, 37.8 g. (0.10 m.), in ethanol, 285 ml., and water, 105 ml., was cooled to ambient temperature and OXONE ® 73.8 g. (0.12 m.), was added in one portion with stirring. After 3 h., an additional 15 g. of OXONE ® was added and stirring at ambient temperature was continued for 1.5 h. more. The mixture was basified by portionwise addition of sodium bicarbonate and filtered.

A second identical run was made and the filtrates were combined and concentrated in vacuo to remove ethanol, leaving an aqueous oily suspension.

The solid was stirred at ambient temperature with ethyl acetate, 1000 ml., overnight, the mixture was filtered and the filtrate was used to extract the above aqueous oily suspension. The water layer was separated and extracted with ethyl acetate (2×300 ml.), the combined extracts were washed twice with brine, dried over sodium sulfate and evaporated to dryness in vacuo. The tan foam residue weighed 57.85 g. (73%) and was used in the subsequent reaction without futher purification.

Step B: Preparation of 5,6-Dihydro-6-allyloxymethyl-4-amino-4H-thieno[2,3-b]thiopyran-2-sulfonamide-7,7-dioxide A solution of 5,6-dihydro-4-acetamide-6-allyloxymethyl-4H-thieno[2,3-b]thiopyran-2-sulfonamide-7,7-dioxide, 27.1 g. (0.069 m), in methanol, 290 ml., and 12N hydrochloric acid, 290 ml., was stirred and refluxed for 18 h. The mixture was concentrated in vacuo and the residue was distributed between ethyl acetate (300 ml.) and saturated sodium bicarbonate solution (150 ml.). The aqueous layer was separated and extracted with ethyl acetate (2×200 ml.), the combined extracts were washed twice with water, dried over sodium sulfate and concentrated in vacuo to yield 16.14 g. (66%) of product.

An analytical sample was crystallized as the hydrogen maleate salt from ethanol-ether to give product melting at 167°-168° C.

Anal. Calcd. for $C_{11}C_{16}N_2O_5S_3.C_4H_4O_4$: C, 38.45; H, 4.30; N, 5.98 Found: C, 37.87; H, 4.18; N, 5.75

Step C: Preparation of 5,6-Dihydro-6-allyloxymethyl-4-ethylamino-4H-thieno[2,3-b]thiopyran-2-sulfonamide-7,7-dioxide, α- and β-Isomer Acetaldehyde, 1.5 ml. (1.19 g, 0.027 m), was added to a solution of 5,6-dihydro-6-allyloxymethyl-4-amino-4H-thieno[2,3-b]thiopyran-2-sulfonamide-7,7-dioxide, 10.0 g. (0.028 m.), in dry tetrahydrofuran, 150 ml., and the mixture was stirred at ambient temperature for 0.75 h. under nitrogen. The solution was added over 15 min. to a stirred suspension of sodium borohydride, 5.3 g. (0.14 m.) in absolute ethanol, 150 ml., at 0° C. After stirring for an additional 15 min. at 0° C., the mixture was treated dropwise with 10% hydrochloric acid, 35 ml., until gas evolution ceased. After concentration in vacuo, the residue was distributed between 200 ml. of water containing 10 ml. of 3N hydrochloric acid and 75 ml. of ethyl acetate. The ethyl acetate layer was washed with 100 ml. of water, the combined aqueous wash and acidic water layer were basified with saturated sodium bicarbonate solution and extracted with ethyl acetate (300 ml. and 2×200 ml.). After washing twice with brine and drying over sodium sulfate, ethyl acetate was evaporated in vacuo to yield 6.6 g. (63%) of the mixture of isomers as a yellow foam.

An isomeric mixture, 3.48 g., was chromatographed on silica gel 60 (E. Merck, 230-400 mesh) eluting with chloroform/methanol/ammonium hydroxide 95:5:0.5 to yield 0.65 g of the α-isomer and 0.65 g. of the β-isomer.

The hydrochloride salt of the α-isomer melts at 150°-153° C. after crystallization from ethanol-ether.

Anal. Calcd. for $C_{13}H_{20}N_2O_5S_3$.HCl: C,37.45; H, 5.08; N, 6.72 Found: C, 37.21; H, 5.04; N, 6.69

The hydrochloride salt of the β-isomer melts at 205°-206° C. after crystallization for ethanol-ether.

Anal Calcd. for $C_{13}H_{20}N_2O_5S_3$.HCl: C, 37.45; H, 5.08; N, 6.72 Found: C, 37.75; H, 4.72; N, 6.89

Step D: Preparation of (−) 5,6-Dihydro-6-allyloxymethyl-4-ethylamino-4H-thieno[2,3-b]-thiopyran-2-sulfonamide-7,7-dioxide α-Isomer and (+) 5,6-Dihydro-6-allyloxymethyl-4-ethylamino-4H-thieno[2,3-b]thiopyran-2-sulfonamide-7,7-dioxide α-Isomer 5,6-Dihydro-6-allyloxymethyl-4-ethylamino-4H-thieno-[2,3-b]thiopyran-2-sulfonamide-7,7-dioxide α-isomer, 0.65 g (1.70 mmole), and di-p-toluoyl-L-tartaric acid monohydrate, 0.17 g (0.43 mmole) were dissolved in warm acetonitrile, 5 ml. The product was collected and crystallized twice more from 2.5 ml. and 2.0 ml. of acetonitrile, respectively, to yield 132 mg. of the (−)-isomer meltir ; at 119°-124° C. The material was distributed between saturated sodium bicarbonate solution, 10 ml., and ethyl acetate, 25 ml., the aqueous layer was separated and extracted with ethyl acetate (2×25 ml.) the combined extracts were washed twice with water, dried over sodium sulfate and concentrated in vacuo to yield 0.10 g. of the free fase. The hydrochloride salt was prepared with ethanolic hydrogen chloride to afford 84 mg. of product melting at 196°-199° C.

Anal. Calcd. for $C_{13}H_{20}N_2O_5S_3$.HCl.0.5$H_2O$: C, 36.65; H, 5.21; N, 6.58 Found: C, 36.36; H, 4.90; N, 6.39

The combined mother liquors from the three crystallizations of the (−)-enantiomer were concentrated in vacuo and the residue was distributed between saturated sodium bicarbonate solution, 25 ml., and ethyl acetate, 50 ml. The aqueous layer was separated and extracted with ethyl acetate (2×35 ml.), the combined extracts were washed twice with water, dried over sodium sulfate and evaporated in vacuo. The residue and di-p-toluoyl-D-tartaric acid monohydrate, 0.17 g. (0.43 mmole) were dissolved in acetonitrile, 4 ml., with warming. The product was collected and crystallized twice more from 3 ml. portions of acetonitrile to yield 99 mg. of the (+)-isomer melting at 115°-123° C. The material was distributed between saturated sodium bicarbonate solution, 10 ml., and ethyl acetate, 20 ml. The aqueous layer was separated and extracted with ethyl acetate (2×20 ml.), the combined extracts were washed twice with water, dried over sodium sulfate and concentrated in vacuo to afford 0.06 g. of the free base. The crystalline hydrochloride salt was prepared with ethanolic hydrogen chloride to yield 38 mg. of product melting at 198°-200° C.

Anal. Calcd. for $C_{13}H_{20}N_2O_5S_3.HCl.0.5H_2O$: C, 36.65; H, 5.21; N, 6.58 Found: C, 36.45; H, 5.07; N, 6.48

Step E: Preparation of (−) 5,6-Dihydro-6-allyloxymethyl-4-ethylamino-4H-thieno[2,3-b]-thiopyran-2-sulfonamide-7,7-dioxide β-Isomer and (+) 5,6-Dihydro-6-allyloxymethyl-4-ethylamino-4H-thieno-[2,3-b]thiopyran-2-sulfonamide-7,7-dioxide β-Isomer 5,6-Dihydro-6-allyloxymethyl-4-ethylamino-4H-thieno[2,3-b]-thiopyran-2-sulfonamide-7,7-dioxide β-isomer, 0.65 g (1.70 mole) and di-p-toluoyl-L-tartaric acid monohydrate, 0.17 g. (0.43 mmole), were dissolved in 5 ml. of warm acetonitrile. The product was collected and crystallized twice more from 15 ml. portions of acetonitrile to yield 131 mg. of the (−)-enantiomer melting at 198°-199° C. This material was distributed between saturated sodium bicarbonate solution, 15 ml., and ethyl acetate, 2.5 ml., the aqueous layer was separated and extracted with ethyl acetate (2×25 ml.), the combined extracts were washed twice with water, dried over sodium sulfate and evaporated in vacuo to yield 0.10 g, of the free base. The hydrochloride salt was prepared with ethanolic hydrogen chloride to afford 60 mg. of product with an indefinite melting point; $[\alpha]_D^{25} = -57.3°$ for the hydrochloride salt in methanol.

Anal. Calcd. for $C_{13}H_{20}N_2O_5S_3.HCl$: C, 37.45; H, 5.08; N, 6.72 Found: C, 36.91; H, 4.95; N, 6.72

The combined mother liquors from the three crystallization of the (−)-enantiomer were concentrated in vacuo and the residue was distributed between saturated sodium bicarbonate solution, 25 ml., and ethyl acetate, 50 ml. The aqueous layer was separated and extracted with ethyl acetate (2×50 ml.), the combined extracts were washed twice with water, dried over sodium sulfate and evaporated in vacuo to yield 0.50 g. of the free base. A portion of the base, 0.27 g (0.71 millimole), and di-p-toluoyl-D-tartaric acid, 0.15 g. (0.36 mmole), were dissolved in warm acetonitrile, 4 ml. The product, which crystallizes slowly, was colleted and crystallized twice more from 8 ml. and 4 ml. of acetonitrile, respectively, to give 33 mg. of product melting at 201°-202° C. The material was distributed between saturated sodium bicarbonate solution, 10 ml., and ethyl acetate, 20 ml., the aqueous layer was separated and extracted with ethyl acetate (2×20 ml.) and the combined extracts were washed twice with water. After drying over sodium sulfate, the solvent was evaporated in vacuo to yield 28 mg. of the free base of the (+)-enantiomer. The crystalline hydrochloride salt of indefinite melting point was prepared with ethanolic hydrogen chloride to afford 14 mg. of product.

Anal. Calcd. for $C_{13}H_{20}N_2O_5S_3.HCl.1.35H_2O$: C, 35.38; H, 5.14; N, 6.35 Found: C, 35.35; H, 4.90; N, 6.15

EXAMPLE 42

(−)-4-Amino-5,6-dihydro-6-(3-methoxypropyl)-4H-thieno[2,3-b]thiopyran-2-sulfonamide-7,7-dioxide hydrochloride, trans isomer

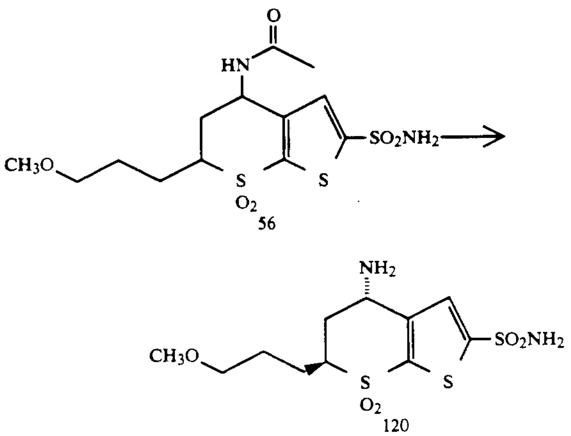

56

120

(trans-isomer)

(−) rotary enantiomer

A solution of 4-acetamido-5,6-dihydro-6-(3-methoxypropyl)-4H-thieno[2,3-b]thiopyran-2-sulfonamide-7,7-dioxide (7.3 g), (prepared employing substantially the same procedures as described in Example 10, Steps A through I), methanol (70 ml.) and 6N HCl (70 ml.) was heated at reflux for 18 hours then evaporated at reduced pressure to a volume of 20 ml. The reaction mixture was made basic with aqueous $NaHCO_3$ and extracted wth ethyl acetate (2×80 ml.). The organic phase was washed with brine, dried over $Na_2SO_4$ and evaporated in vacuo. The residue was crystallized from ethanol (20 ml.) to remove the cis isomer and the product thus obtained was redissolved in hot ethanol, treated with an excess of ethanolic HCl and ether to provide 1.0 g of the title compound which melts at 262° C.

Anal calc for: $C_{11}H_{18}N_2O_5S_3.HCl$, C, 33.79; H, 4.90; N, 7.17 Found: C, 34.11; H, 4.85; N, 7.06

EXAMPLE 43

(−)-4-Amino-5,6-dihydro-6-(3-hydroxypropyl)-4H-thieno [2,3-b]thiopyran-2-sulfonamide-7,7-dioxide, transisomer Step A: Preparation of (−)-5,6-Dihydro-6-(3-hydroxypropyl)-4-propionamido-4H-thieno[2,3-b]thiopyran-2-sulfonamide-7,7-dioxide, trans isomer To a solution of (−)-5,6-dihydro-6-(3-methoxypropyl-4-propionamido-4-thieno[2,3-b]thiopyran-2-sulfonamide-7,7-dioxide (600 mg, 1.5 mm) in sulfolane (14 ml) was added trimethylsilyl acetate (270 μl, 1.89 mM) and the mixture was heated at 40°-50° C. for 18 hours. The reaction mixture was poured into $H_2O$, extracted with ethyl acetate, washed with brine, dried over sodium sulfate, evaporated in vacuo and chromatographed on $SiO_2$ ($CHCl_3$—$CH_3OH$, 12:1) to give 160 mg. of TITLE, Step A and 130 mg. of mixed cis and trans isomers.

Step B: Preparation of
(−)-4-Amino-5,6-dihydro-6-(3-hydroxypropyl)-4H-thieno[2,3-b]thiopyran-2-sulfonamide-7,7-dioxide, trans-isomer A mixture of compound from Step A (100 mg., 0.42 mM) $CH_3OH$ (25 ml.) and 12N HCl (3 ml.) was heated at reflux for 24 hours. The $CH_3OH$ was evaporated in vacuo. The aqueous phase was made basic with saturated sodium carbonate, evaporated to dryness and extracted with hot ethyl acetate which was evaporated to dryness to give 5 mg of title compound.

Anal. for $C_{10}H_{16}N_2O_5S_3$ Calc: C, 35.3; H, 4.7; N, 8.2 Found: C, 35.7; H, 4.6; N 7.9

EXAMPLE 44

5,6-Dihydro-4-ethylamino-6-methoxymethyl-6-propyl-4H-thieno [2,3-b]thiopyran-2-sulfonamide-7,7-dioxide hydrochloride

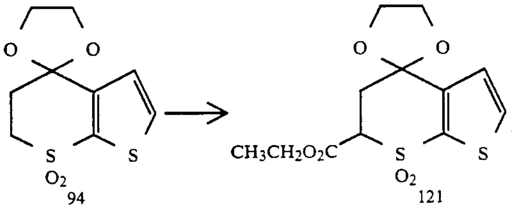

94 121

Step A:
5,6-Dihydro-7,7-dioxo-6-ethoxycarbonyl-4H-thieno[2,3-b]thiopyran-4-one, ethylene ketal To a stirred solution of 5,6-dihydro-7,7-dioxo-4H-thieno[2,3-b]thiopyran-4-one, ethylene ketal (12.3 g, 50 mmol) in dry THF (250 mL) under nitrogen at −30° C., was added a solution of lithium bis(trimethylsilyl)amide in hexane (1M, 110 mL, 110 mmols) over 5–10 minutes. After 0.5 hour at −30° C., a solution of diethyl carbonate (9.8 g, 83 mmols) in THF (25 mL) was added, and the reaction mixture was allowed to warm to 10° C. The reaction mixture was mixed with 10% $NH_4Cl$ solution (500 mL) and the THF was removed under reduced pressure. The resulting aqueous solution was extracted with EtOAc (3×300 mL), and the combined organic extracts were washed with $H_2O$ (2×100 mL), brine (2×150 mL) and dried ($Na_2SO_4$). Removal of the dried filtered solvent and recrystallization of the residue (11.3 g) from 1-chlorobutane gave pure title compound, mp 131° C.

Anal., Calcd. for $C_{12}H_{14}O_6S_2$: C, 45.27; R, 4.43 Found: C, 44.91; H, 4.32

Step B:
5,6-Dihydro-7,7-dioxo-6-ethoxycarbonyl-6-propyl-4H-thieno[2,3-b]thiopyran-4-one, ethylene ketal 121

-continued

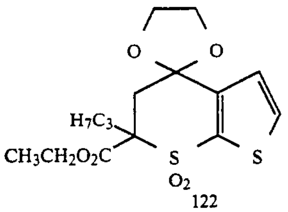

122

A solution of product from Step A (3.18 g, 10 mmols) in DMF (10 mL) was added to a stirred mixture of sodium hydride (0.50 g, 60% dispersion, 12.5 mmols) in DMF (30 mL). After complex addition, the reaction mixture was stirred for 0.5 hour and propyl bromide (1.35 g, 11 mmols) was added by pipette. After an additional two hours at ambient temperature, another charge of propyl bromide was added (1.35 g, 11 mmols). After stirring for an additional 18 hours, the reaction mixture was diluted with $H_2O$ (1.50 mL) and extracted with ether (3×75 mL). The combined ether extracts were washed with $H_2O$ (2×50 mL), brine (2×50 mL) and dried ($Na_2SO_4$). Removal of the filtered dried solvent under reduced pressure gave an opaque white gum. Trituration with hexane gave 2.6 g of the title compound as a white solid, used directly in the next step.

Step C: 5,6-Dihydro-7,7-dioxo-6-hydroxymethyl-6-propyl-4H-thieno[2,3-b]thiopyran-4-one, ethylene ketal 122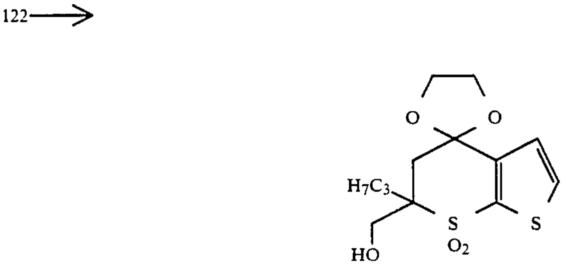

123

To a stirred, cooled suspension of lithium aluminum hydride (356 mg) in ether (15 mL) was added a solution of the product from step B (2.6 g) in THF (15 ml) over a ¾ hour period. The reaction mixture was stirred at 25° C. overnight, cooled in ice, then slowly treated with $H_2O$ (0.357 ml), 6N NaOH (0.446 ml), then more $H_2O$ (1.25 ml). The salts were filtered, the solution dried over $Na_2SO_4$ and evaporated in vacuo to leave 1.2 g of the title compound as a yellow oil.

Step D: 5,6-Dihydro-7,7-dioxo-6-methoxymethyl-6-propyl-4H-thieno[2,3-b]thiopyran-4-one, ethylene ketal 123

-continued

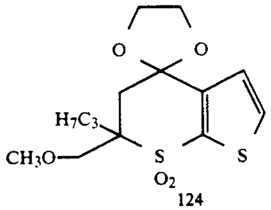

124

Under nitrogen, sodium hydride (50% in oil, 230 mg) was suspended with stirring in cold THF (8 ml). A solution of 5,6-dihydro-7,7-dioxo-6-hydroxymethyl-6-propyl-4H-thieno[2,3-b]thiopyran-4-one, ethylene ketal (1.3 g) in THF (5 ml) was added over a ½ hour period. The reaction mixture was stirred for ½ hour at 25° C. then methyl iodide (1.2 g) was added. After 1 hour the reaction mixture was cooled in ice, and methanol (1 ml) was added over 5 minutes. The solvents were evaporated, the residue dissolved in ethyl acetate, washed with $H_2O$ then brine, dried over $Na_2SO_4$ and evaporated in vacuo. Crystallization of the residue from ethyl acetate-hexane gave 1.2 g of the title compound which melts at 90°-92° C.

Step E: 5,6-Dihydro-7,7-dioxo-6-methoxymethyl-6-propyl-4H-thieno[2,3-b]thiopyran-2-sulfonamide-4-one, ethylene ketal

124

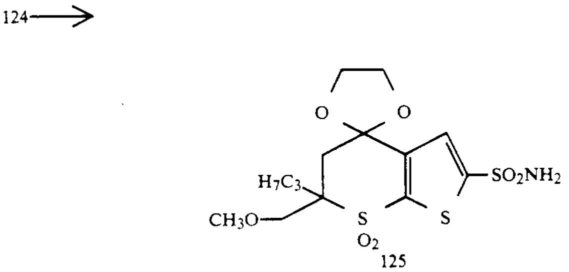

125

Under nitrogen a stirred solution of 5,6-dihydro-7,7-dioxo-6-methoxymethyl-6-propyl-4H-thieno[2,3-b]thiopyran-4-one, ethylene ketal (10.3 g) in THF (90 ml) was cooled to −78° C. A solution of 2.5N butyl lithium in THF (16.2 ml) was added over 20 minutes. Stirring was continued for 20 minutes then the nitrogen inlet was replaced with an $SO_2$ inlet and $SO_2$ was added at such a rate that the temperature rose to −57° then dropped back to −78° C. The cooling bath was removed and stirring was continued for 1 hour. The solvents were removed in vacuo, the residue stirred in an ice bath and treated with a solution of sodium acetate (7.9 g) in $H_2O$ (72 ml) then hydroxylamine-O-sulfonic acid (9.2 g). Stirring was continued for 45 minutes, the solution made basic with aqueous $NaHCO_3$, extracted with ethyl acetate which was washed with brine, dried over $Na_2SO_4$ and evaporated to give 11 g of the title compound which was used without purification in the next step.

Step F: 5,6-Dihydro-7,7-dioxo-6-methoxymethyl-6-propyl-4H-thieno[2,3-b]thiopyran-2-sulfonamide-4-one

125

-continued

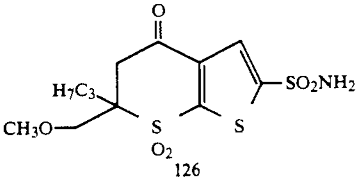

126

A solution of 5,6-dihydro-7,7-dioxo-6-methoxymethyl-6-propyl-4H-thieno[2,3-b]thiopyran-2-sulfonamide-4-one, ethylene ketal (11 g), THF (150 ml) and 6N HCl (150 ml) was heated at reflux for 45 minutes. The THF was evaporated in vacuo and the acid solution was extracted with ethyl acetate. The organic phase was washed with brine, dried over $Na_2SO_4$ and evaporated in vacuo. Trituration of the residue with butyl chloride gave 8 g of the title compound as a white solid which melts at 197° C.

Step G: 5,6-Dihydro-4-hydroxy-6-methoxymethyl-6-propyl-4H-thieno[2,3-b]thiopyran-2-sulfonamide-7,7-dioxide

126

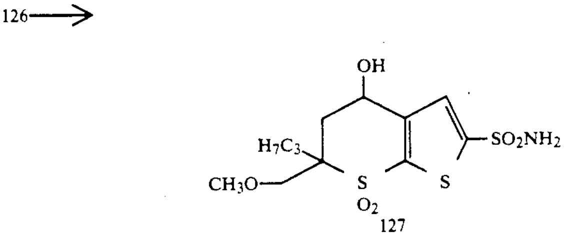

127

To a stirred suspension of 5,6-dihydro-7,7-dioxo-6-methoxymethyl-6-propyl-4H-thieno[2,3-b]thiopyran-2-sulfonamide-4-one (8 g) in methanol (400 ml) was added sodium borohydride (0.83 g) over a 5 minute period. After ½ hour the methanol was evaporated, the residue dissolved in ethyl acetate, washed with 2N HCl, $H_2O$, brine, dried over $Na_2SO_4$ and evaporated in vacuo to provide 8.6 g the title compound as a foam.

Step H: N'-(5,6-Dihydro-4-hydroxy-6-methoxymethyl-6-propyl-4H-thieno[2,3-b]thiopyran-2-sulfonyl)-N,N-dimethylformamidine-7,7-dioxide

127

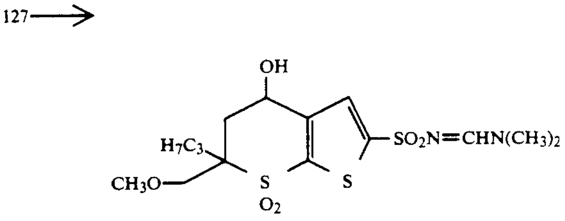

A solution of 5,6-dihydro-4-hydroxy-6-methoxymethyl-6-propyl-4H-thieno[2,3-b]thiopyran-2-sulfonamide-7,7-dioxide (8.6 g) and dimethylformamide dimethylacetal (4.3 ml) in acetonitrile (400 ml) was stirred for 1½ hours and evaporated in vacuo. The residue was dissolved in ethyl acetate, washed with 1N HCl, $H_2O$, and brine, then dried over $Na_2SO_4$ to give 9.6 g of the title compound as an oil.

Step I: N'-(5,6-Dihydro-4-methanesulfonyloxy-6-methoxymethyl-6-propyl-4H-thieno[2,3-b]thiopyran-2-sulfonyl)-N,N-dimethylformamidine-7,7-dioxide

128

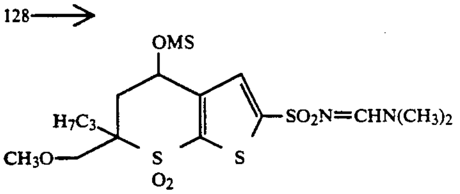

To a stirred solution of N'-(5,6-dihydro-4-hydroxy-6-methoxymethyl-6-propyl-4H-thieno[2,3-b]thiopyran-2-sulfonyl)-N,N-dimethylformamidine-7,7-dioxide (9.6 g) in THF (175 ml) was added triethylamine (3.9 m) and methanesulfonic anhydride. After 3 hours the THF was evaporated, the residue treated with $H_2O$ (100 ml) and extracted with ethyl acetate (2×100 ml). The organic phase was washed with brine, dried over $Na_2SO_4$, and evaporated in vacuo to give 9 g of the title compound as an oil.

Step J: N'—(4-Azido-5,6-dihydro-6-methoxymethyl-6-propyl-4H-thieno[2,3-b]thiopyran-2-sulfonyl)-N,N-dimethylformamidine-7,7-dioxide

129

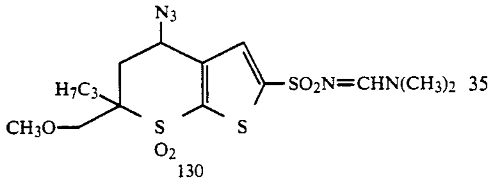

130

Under nitrogen a solution of N'-(5,6-dihydro-4-methanesulfonyloxy-6-methoxymethyl-6-propyl-4H-thieno[2,3-b]thiopyran-2-sulfonyl)-N,N-dimethylformamidine-7,7-dioxide (9 g) in DMSO (230 ml) was treated with sodium azide (1.62 g) and stirred at 25° C. for 3 hours. Additional sodium azide (0.6 g) was added and stirring continued for 2 hours. The reaction mixture was poured into ice $H_2O$ (300 ml) and extracted with ethyl acetate (2×150 ml), the extract was washed with $H_2O$ and brine, dried over $Na_2SO_4$ and evaporated in vacuo to give 7.7 g of the title compound as a foam.

Step K: N'-(4-Amino-5,6-dihydro-6-methoxymethyl-6-propyl-4H-thieno[2,3-b]thiopyran-2-sulfonyl)-N,N-dimethylformamidine-7,7-dioxide

130

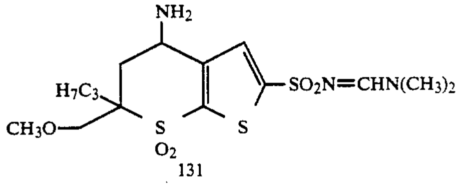

131

A solution of N'-(4-azido-5,6-dihydro-6-methoxymethyl-6-propyl-4H-thieno[2,3-b]thiopyran-2-sulfonyl)-N,N-dimethylformamidine-7,7-dioxide (7.7 g) and triphenylphosphine (4.7 g) in THF (230 ml) was stirred at 25° C. for 20 hours. Water (70 ml) was added and the reaction mixture was heated at reflux for 5 hours. The THF was evaporated in and the aqueous phase extracted with ethyl acetate which was washed with brine, dried over $Na_2SO_4$ and evaporated in vacuo to give 7.4 g of a mixture of α and β isomers. The isomers were separated by chromatography on silica eluting with $CHCl_3$—$CH_3OH$ 22:1.

Step L: 4-Amino-5,6-dihydro-6-methoxymethyl-6-propyl-4H-thieno[2,3-b]thiopyran-2-sulfonamide-7,7-dioxide hydrochloride

131

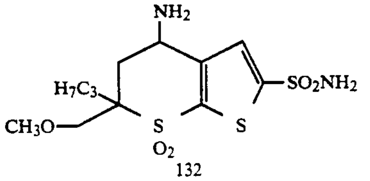

132

A solution of N'-(4-amino-5,6-dihydro-6-methoxymethyl-6-propyl-4H-thieno[2,3-b]thiopyran-2-sulfonyl)-N,N-dimethylformamidine-7,7-dioxide (300 mg) in THF (25 ml) and 6N HCl (10 ml) was heated at reflux for 5 hours. The THF was evaporated in vacuo and the residue made basic with $NaHCO_3$, extracted with ethyl acetate, washed with brine, dried over $Na_2SO_4$ and evaporated in vacuo. The residue was dissolved in ethanol (3 ml), treated with a slight excess of ethanolic HCl, then with ether and refrigerated overnight to give the title compound.

Analysis calc'd for $C_{12}H_{20}N_2O_5S_3.HCl.\frac{1}{4}C_2H_5OH$, C, 36.05; H, 5.44; N, 6.73; Found (α-isomer) C, 36.15, H, 5.10; N, 6.76

Analysis calc'd for $C_{12}H_{20}N_2O_5S_3.HCl$, C, 35.59; H, 5.23; N, 6.92; Found (β-isomer) C, 35.61; H, 5.12; N, 6.94

EXAMPLE 45

5,6-Dihydro-4-ethylamino-6-methoxymethyl-6-propyl-4H-thieno[2,3-b]thiopyran-2-sulfonamide-7,7-dioxide hydrochloride

131

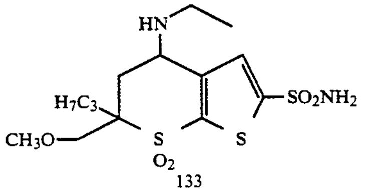

133

Acetaldehyde (0.42 ml) was added under nitrogen to a solution of N'-(4-amino-5,6-dihydro-6-methoxymethyl-6-propyl-4H-thieno[2,3-b]thiopyran-2-sulfonyl)-N,N-dimethylformamidine-7,7-dioxide (2.3 g) in THF (28 ml). After 45 minutes the reaction mixture was added dropwise to a stirred suspension of sodium borohydride (1.07 g) in ethanol (28 ml) which had been cooled to 0° C. After 30 minutes the reaction was quenched with 3N HCl and the THF and ethanol were evaporated in vacuo. The residue was made basic with $NaHCO_3$, and extracted with ethyl acetate which was washed with brine, dried over $Na_2SO_4$, evaporated in vacuo and purified by column chromatography on silica ($CHCl_3$—$CH_3OH$ 18:1). The pertinent fractions were evaporated, the residue was dissolved in ethanol (8 ml) and treated with a slight excess of ethanolic HCl then ether to give 1.2 g of the title compound.

Analysis calc. for $C_{14}H_{24}N_2O_5S_3.HCl.\frac{1}{2}C_2H_5OH$, C, 39.50; H, 6.18; N, 6.14; Found (α-isomer) C, 39.83; H, 5.81; N, 6.43 Found (β-isomer) C, 39.41; H, 5.80; N, 6.42

EXAMPLE 46

6-(3-(Di-2-methoxyethyl)aminomethyl-4-hydroxybenzyl)-4-ethylaminothieno[2,3-b]thiopyran-2-sulfonamide dihydrochloride, trans isomer Employing substantially the same procedure as described in Example 35, but substituting di-(2-methoxyethyl)amine for the dimethylamine used therein, the title compound was prepared, with m.p. 150°-165° C.

Analysis calc. for $C_{23}H_{35}N_3O_7S_3.2HCl.H_2O$ C, 43.35; H, 6.17; N, 6.60 Found: C, 43.09; N, 5.85; N, 6.53

EXAMPLE 47

(S,S)5,6-Dihydro-4-ethylamino-6-(4-butyramido)-4H-thieno[2,3-b]thiopyran-2-sulfonamide-7,7-dioxidehydrochloride The corresponding nitrile (see Table I) was hydrolyzed with concentrated sulfuric acid to yield product. The hydrochloride salt was prepared from ethanolic HCl; mp 90° dec., $[a]_D^{25°} = -7.2$ ($H_2O$)

Anal. calcd. for $C_{13}H_{21}N_3O_5S_3.HCl/\frac{1}{2}H_2O.\frac{1}{2}THF$ Calcd: C, 37.76; H, 5.71; N, 8.81 Found: C, 38.00; H, 5.46; N, 8.46

EXAMPLE 48

(S,S) 5,6-Dihydro-4-ethylamino-6-(3-carboxypropyl)-4H-thieno[2,3-b]thiopyran-2-sulfonamide-7,7-dioxide hydrochloride salt The corresponding nitrile (see Table I) was hydrolyzed to the acid using refluxing 6N HCl; mp>100° dec; $[\alpha]_D{}^{25} = -9.36$($CH_3OH$)

Analysis calcd. for $C_{13}H_{20}N_2O_6S_3.HCl.THF$-1.5 $H_2O$ Calcd: C, 38.37; H, 6.06; n, 5.26 Found: C, 38.39; H, 5.67; N, 5.01

EXAMPLE 49

| Pharmaceutical Formulations | | |
|---|---|---|
| Active compound | 1 mg | 15 mg |
| Monobasic sodium phosphate $2H_2O$ | 9.38 mg | 6.10 mg |
| Dibasic sodium phosphate $.12H_2O$ | 28.48 mg | 16.80 mg |
| Benzalkonium chloride | 0.10 mg | 0.10 mg |
| Water for injection q.s. and. | 1.0 mg | 1.0 mg |

The active compound, phosphate buffer salts, and benzalkonium chloride are added to and dissolved in water. The pH of the composition is adjusted to 6.8 and diluted to volume. The composition is rendered sterile by ionizing radiation.

| | |
|---|---|
| Active compound | 5 mg |
| petrolatium q.s. and. | 1 gram |

The compound and the petrolatum are aseptically combined.

| | |
|---|---|
| Active compound | 1 mg |
| Hydroxypropylcellulose q.s. | 12 mg |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

What is claimed is:

1. A compound of structural formula:

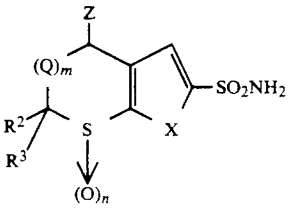

or a pharmaceutically acceptable salt thereof

X is —S—, m is 1 or 2;

n is 0, 1 or 2;

Z is 1) hydrogen,
2) —$OR^4$ wherein $R^4$ is
   a) hydrogen, or
   b) $C_{1-5}$ alkyl, either unsubstituted or substituted with
      i) —OH, or
      ii) —$NR^6R^7$ wherein $R^6$ and $R^7$ are independently hydrogen, $C_{1-3}$alkyl, —CO—$C_{1-3}$alkyl,
3) =O, or
4) —$NRR^1$;

R is hydrogen or $R^1$;

$R^1$ is

1) $C_{2-7}$alkenyl,
2) $C_{2-7}$alkynyl, or
3) $C_{1-6}$alkyl, straight, branched or cyclic, either unsubstituted or substituted with 1, 2 or 3 substituents wherein the substituents are independently:
   a) halogen;
   b) hydroxy;
   c) $C_{1-3}$alkoxy;
   d) —$NR^6R^7$;

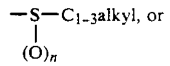 e)

f) —CN;

$R^2$ is hydrogen or $C_{1-5}$alkyl;

$R^3$ is

1) —$C_{1-5}$ alkyl substituted with one or more of a) hydroxy,
b) $-NR^8R^9$, wherein $R^8$ is
i) hydrogen, or
ii) $C_{1-3}$alkyl; and
$R^9$ is
i) $C_{1-3}$alkoxy-$C_{1-3}$alkyl,
ii) hydroxy-$C_{1-3}$alkyl,
iii) benzyl either unsubstituted or substituted on the phenyl group with up to three of halo, hydroxy, $C_{1-3}$alkyl, $C_{1-3}$alkoxy, $-CH_2NR^{10}R^{11}$ or $-NR^{10}R^{11}$ wherein $R^{10}$ and $R^{11}$ are independently hydrogen, $C_{1-3}$alkyl, or $C_{1-3}$alkoxy-$C_{1-3}$alkyl, or
iv) $-CO-C_{1-6}$alkyl;
c) $C_{1-5}$alkoxy, either unsubstituted or substituted with one or more of:
i) hydroxy,
ii) $C_{1-3}$ alkoxy,
iii) $NR^{10}R^{11}$,
iv) $-CN$,
v) phenyl, either unsubstituted or substituted with one or more of
A) hydroxy,
B) $C_{1-3}$alkoxy,
C) $C_{1-5}$alkyl-$NR^{10}R^{11}$, or
D) halo,
d) $-SH$,
e) $-CN$,

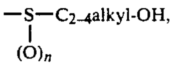
f)

g) phenyl, either unsubstituted or substituted with up to three of
i) hydroxy,
ii) $C_{1-3}$ alkoxy, or
iii) $C_{1-5}$alkyl-$NR^{10}R^{11}$,
h) $COR^{14}$ wherein $R^{14}$ is
i) hydroxy,
ii) $-NH_2$, or
iii) $C_{1-5}$ alkoxy, or
iv) $-NR^{12}R^{13}$ or
i) $C_{2-5}$alkenyloxy; and Q is 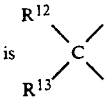 wherein $R^{12}$ and $R^{13}$ independently are hydrogen or $C_{1-4}$alkyl.

2. The compound of claim 1 wherein Z is $-NRR^1$; and Q is $-CH_2-$.

3. The compound of claim 2 wherein m is 1.

4. The compound of claim 3 wherein n is 2.

5. The compound of claim 4 wherein R is hydrogen and $R^1$ is $C_{1-6}$alkyl.

6. The compound of claim 5 wherein $R^2$ is hydrogen or $C_{1-3}$alkyl and $R^3$ is $C_{1-5}$alkoxy-$C_{1-5}$alkyl, or hydroxy-$C_{0-5}$alkoxy-$C_{1-5}$alkyl, $C_{1-5}$alkoxy-$C_{1-5}$alkoxy-$C_{1-5}$alkyl, hydroxy-$C_{1-5}$alkylamino-$C_{1-5}$alkyl, hydroxy-$C_{1-5}$alkylthio-$C_{1-5}$alkyl, or $C_{2-5}$alkenyloxy-$C_{1-5}$alkyl.

7. The compound of claim 6 which is
a) 5,6-dihydro-6-(2-ethoxyethyl)-4-ethylamino-4H-thieno[2,3-b]thiopyran-2-sulfonamide-7,7-dioxide;
b) 5,6-dihydro-6-ethoxymethyl-4-ethylamino-4H-thieno[thieno[2,3-b]thiopyran-2-sulfonamide-7,7-dioxide;
c) 5,6-dihydro-6-methoxymethyl-4-(n-propylamino)-4H-thieno[2,3-b]thiopyran-2-sulfonamide-7,7-dioxide;
d) 5,6-dihydro-6-(3-methoxypropyl)-4-(methylamino)-4H-thieno[2,3-b]thiopyran-2-sulfonamide-7,7-dioxide;
e) 5,6-dihydro-6-(3-methoxypropyl)-4-(n-propylamino)-4H-thieno[2,3-b]thiopyran-2-sulfonamide-7,7-dioxide;
f) 5,6-dihydro-4H-4-ethylamino-6-(3-methoxypropyl)-thieno[2,3-b]thiopyran-2-sulfonamide-7,7-dioxide;
g ) 5,6-dihydro-6-(3-methoxypropyl)-4-propylamino-4H-thieno[2,3-b]thiopyran-2-sulfonamide-7,7-dioxide;
h) 5,6-dihydro-4-ethylamino-4H-6-(2-hydroxyethylamino)methylthieno[2,3-b]thiopyran-2-sulfonamide-7,7- dioxide;
i) 5,6-dihydro-6-allyloxymethyl-4-ethylamino-4H-thieno[2,3-b]thiopyran-2-sulfonamide-7,7-dioxide;
j) 5,6-dihydro-6-(3-allyloxy)propyl-4-propylamino-4H-thieno[2,3-b]thiopyran-2-sulfonamide-7,7-dioxide;
k) 5,6-dihydro-6-[3-(2-methoxy)ethoxy]propyl-4-propylamino-4H-thieno[2,3-b]thiopyran-2-sulfonamide-7,7-dioxide;
l) 5,6-dihydro-4-ethylamino-6-[3-(2-methoxy)ethoxy]propyl-4H-thieno[2,3-b]thiopyran-2-sulfonamide-7,7-dioxide;
m) 5,6-dihydro-6-[3-(2-ethoxy)ethoxy]propyl-4-propylamino-4H-thieno(2,3-b]thiopyran-2-sulfonamide-7,7-dioxide;
n) 5,6-dihydro-4-ethylamino-6-[2-(2-hydroxyethylthio)ethyl]-4H-thieno[2,3-b]thiopyran-2-sulfonamide-7,7-dioxide;
o) 5,6-dihydro-4-propylamino-6-(2-methoxyethoxy)-methyl-4H-thieno[2,3-b]thiopyran-2-sulfonamide-7,7-dioxide;
p) 5,6-dihydro-4-ethylamino-4H-6-(2-hydroxyethyl-)aminomethylthieno[2,3-b]thiopyran-2-sulfonamide-7,7-dioxide;
q) 5,6-dihydro-6-(3-hydroxypropyl)-4-propylamino-4H-thieno[2,3-b]thiopyran-2-sulfonamide-7,7-dioxide;
r) 4-amino-5,6-dihydro-6-(3-methoxypropyl)-4H-thieno[2,3-b]thiopyran-2-sulfonamide-7,7-dioxide;
s) 5,6-dihydro-6-[2-(2-methoxy)ethoxylethyl-4-ethylamino-4H-thieno[2,3-b]thiopyran-2-sulfonamide-7,7-dioxide;
t) 5,6-dihydro-6-[3-(3-methoxy)propoxylpropyl-4-propylamino-4H-thieno[2,3-b]thiopyran-2-sulfonamide-7,7-dioxide; or
u) 5,6-dihydro-4-propylamino-6-[3-(2-hydroxyethylthio)propyl]-4H-thieno[2,3-b]thiopyran-2-sulfonamide-7,7-dioxide;
or a pharmaceutically acceptable salt thereof.

8. The compound of claim 7 which is the trans diastereomer of 5,6-dihydro-6-(2-ethoxyethyl)-4-ethylamino-4H-thieno[2,3-b]thiopyran-2-sulfonamide-7,7-dioxide; 5,6-dihydro-4H-4-ethylamino-6-(3-methoxypropyl)-thieno[2,3-b]thiopyran-2-sulfonamide-7,7-dioxide; 5,6-dihydro-6-(3-methoxypropyl)-4-propylamino-4H-thieno[2,3-b]thiopyran-2-sulfonamide-7,7-dioxide; 5,6-dihydro-4-ethylamino-4H-6-(2-hydroxyethyl)aminomethylthieno[2,3-b]thiopyran-2-sulfonamide-7,7-dioxide; 5,6-dihydro-6-allyloxymethyl-4-ethylamino-4H-thieno[2,3-b]thiopyran-2-sulfonamide-7,7-dioxide; 5,6-dihydro-6-(3-allyloxy)propyl-4-propylamino-4H- thieno[2,3-b]thiopyran-2-sulfonamide-7,7-dioxide; 5,6-dihydro-6-[3-(2-methoxy)ethoxylpropyl-4-propylamino-4H-thieno[2,3-b]thiopyran-2-sulfonamide-7,7-dioxide; 5,6-dihydro-4-ethylamino-6-[3-(2-methoxy)ethoxylpropyl-4H-thieno[2,3-b]thiopyran-2-sulfonamide-7,7-dioxide; 5,6-dihydro-6-[3-(2-ethoxy)ethoxylpropyl-4-propylamino-4H-thieno[2,3-b]thiopyran-2-sulfonamide-7,7-dioxide; 5,6-dihydro-4-ethylamino-6-[2-(2-hydroxyethylthio)ethyl]-4H-thieno[2,3-b]thiopyran-2-sulfonamide-7,7-dioxide; or 5,6-dihydro-4-propylamino-6-(2-methoxyethoxy)methyl-4H-thieno[2,3-b]thiopyran-2-sulfonamide-7,7-dioxide.

9. The compound of claim 7 which is the trans-(S,S)-enantiomer of 5,6-dihydro-6-(2-ethoxyethyl)-4-ethylamino-4H-thieno[2,3-b]thiopyran-2-sulfonamide-7,7-dioxide; 5,6-dihydro-4H-4-ethylamino-6-(3-methoxypropyl)thieno[2,3-b]thiopyran-2-sulfonamide-7,7-dioxide; 5,6-dihydro-6-(3-methoxypropyl)-4-propylamino-4H-thieno[2,3-b]thiopyran-2-sulfonamide-7,7-dioxide; 5,6-dihydro-4-ethylamino-4H-6-(2-hydroxyethylamino)methylthieno-[2,3-b]thiopyran-2-sulfonamide-7,7-dioxide; 5,6-dihydro-6-(3-allyloxy)propyl-4-propylamino-4R-thieno[2,3-b]-thiopyran-2-sulfonamide -7,7-dioxide; 5,6-dihydro-6-[3-(2-methoxy)ethoxylpropyl-4-propylamino-4H-thieno[2,3-b]thiopyran-2-sulfonamide-7,7-dioxide; 5,6-dihydro-6-[3-(2-ethoxy)ethoxy]propyl-4-propylamino-4H-thieno[2,3-b]thiopyran-2-sulfonamide-7,7-dioxide; 5,6-dihydro-6-(3-hydroxypropyl)-4-propylamino-4H-thieno[2,3-b]thiopyran-2-sulfonamide-7,7-dioxide; 4-amino-5,6-dihydro-6-(3-methoxypropyl)-4H-thieno[2,3-b]thiopyran-2-sulfonamide-7,7-dioxide; 5,6-dihydro-6-[2-(2-methoxy)ethoxy]ethyl-4-ethylamino-4H-thieno[2,3-b]thiopyran-2-sulfonamide-7,7-dioxide; 5,6-dihydro-6-[3-(2-methoxy)ethoxylpropyl-4-ethylamino-4H-thieno[2,3-b]thiopyran-2-sulfonamide-7,7-dioxide; 5,6-dihydro-6-[3-(3-methoxy)propoxylpropyl-4-propylamino-4H-thieno[2,3-b]thiopyran-2-sulfonamide-7,7-dioxide; or 5,6-dihydro-4-propylamino-6-[3-(2-hydroxyethylthio)-propyl]-4H-thieno[2,3-b]thiopyran-2-sulfonamide-7,7-dioxide.

10. The compound of claim 7 which is the cis-diasteriomer of 5,6-dihydro-6-(2-ethoxyethyl)-4-ethylamino-4H-thieno[2,3-b]thiopyran -2-sulfonamide-7,7-dioxide; 5,6-dihydro-4H-4-ethylamino-6-(3-methoxypropyl)-thieno[2,3-b]thiopyran-2-sulfonamide-7,7-dioxide; 5,6-dihydro-6-(3-methoxypropyl)-4-propylamino-4H-thieno[2,3-b]thiopyran-2-sulfonamide-7,7-dioxide; 5,6-dihydro-4-ethylamino-4H-6-(2-hydroxyethylamino)methylthieno-[2,3-b]thiopyran-2-sulfonamide-7,7-dioxide; 5,6-dihydro-6-allyloxymethyl-4-ethylamino-4H-thieno[2,3-b]thiopyran-2-sulfonamide-7,7-dioxide; or 5,6-dihydro-4-propylamino-6-(2-methoxyethoxy)methyl-4H-thieno[2,3-b]thiopyran-2-sulfonamide-7,7-dioxide.

11. The compound of claim 9 which is 5,6-dihydro-6-(3-methoxypropyl)-4-propylamino-4H-thieno[2,3-b]thiopyran-2-sulfonamide-7,7-dioxide.

12. An ophthalmological formulation for the treatment of ocular hypertension comprising an ophthalmological carrier and an effective ocular antihypertensive amount of the compound of claim 1.

13. A method of lowering ocular hypertension which comprises the topical ocular administration of an effective ocular antihypertensive amount of the compound of claim 1 to a patient in need of such treatment.

14. A method of treating psoriasis which comprises the topical administration of an effective amount of the compound of claim 1 to a patient in need of such treatment.

15. A method of treating psoriasis which comprises the oral administration of an effective amount of the compound of claim 1 to a patient in need of such treatment.

* * * * *